(12) United States Patent
Hermann et al.

(10) Patent No.: US 9,334,278 B2
(45) Date of Patent: May 10, 2016

(54) PYRROLO[2,3-B]PYRAZINES AS SYK INHIBITORS

(71) Applicant: Hoffmann-La Roche Inc., Nutley, NJ (US)

(72) Inventors: Johannes Cornelius Hermann, Jersey City, NJ (US); Joshua Kennedy-Smith, New York, NY (US); Matthew C. Lucas, Lexington, MA (US); Fernando Padilla, Verona, NJ (US); Ryan Craig Schoenfeld, Basking Ridge, NJ (US); Peter Michael Wovkulich, Apalachin, NY (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 14/421,084

(22) PCT Filed: Aug. 19, 2013

(86) PCT No.: PCT/EP2013/067233
§ 371 (c)(1),
(2) Date: Feb. 11, 2015

(87) PCT Pub. No.: WO2014/029732
PCT Pub. Date: Feb. 27, 2014

(65) Prior Publication Data
US 2015/0218170 A1 Aug. 6, 2015

Related U.S. Application Data

(60) Provisional application No. 61/691,384, filed on Aug. 21, 2012.

(51) Int. Cl.
| | |
|---|---|
| *C07D 487/04* | (2006.01) |
| *A61K 31/4985* | (2006.01) |
| *C07D 519/00* | (2006.01) |
| *A61K 31/506* | (2006.01) |
| *A61K 45/06* | (2006.01) |
| *C07D 471/04* | (2006.01) |

(52) U.S. Cl.
CPC .......... *C07D 487/04* (2013.01); *A61K 31/4985* (2013.01); *A61K 31/506* (2013.01); *A61K 45/06* (2013.01); *C07D 471/04* (2013.01); *C07D 519/00* (2013.01)

(58) Field of Classification Search
CPC ........................ C07D 487/04; A61K 31/4985
USPC ........................................... 544/350; 514/249
See application file for complete search history.

(56) References Cited

U.S. PATENT DOCUMENTS

2011/0288067 A1* 11/2011 Hendricks et al. ....... 514/210.16

FOREIGN PATENT DOCUMENTS

| WO | 2009106442 | 9/2009 |
|---|---|---|
| WO | 2009106443 | 9/2009 |

(Continued)

OTHER PUBLICATIONS

Pearce et al., Failure modes in anticancer drug discovery and development, Cancer Drug Design and Discovery Edited by Stephen Neidle, Chapter 18, pp. 424-435 (2008).*

(Continued)

*Primary Examiner* — Deepak Rao

(57) ABSTRACT

The present invention relates to the use of novel pyrrolo[2,3-b]]pyrazines wherein all variable substituents are defined as described herein, which are SYK inhibitors and are useful for the treatment of auto-immune and inflammatory diseases.

I

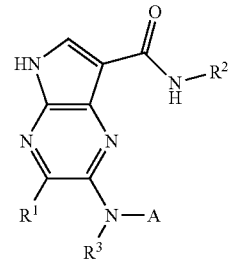

II

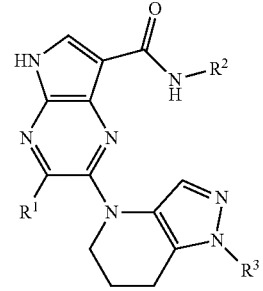

III

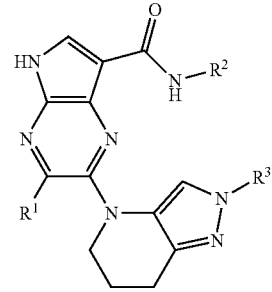

16 Claims, No Drawings

(56) References Cited

FOREIGN PATENT DOCUMENTS

WO     2009106444     9/2009
WO     2011144585     11/2011

OTHER PUBLICATIONS

Johnson et al., Relationships between drug activity in NCI preclinical in vitro and in vivo models and early clinical trials, British Journal of Cancer (2001) 64(10): 1424-1431.*

Simone, Oncology: Introduction, Cecil Textbook of Medicine, 20th Edition, vol. 1, pp. 1004-1010, 1996.*

Gura, Systems for identifying New Drugs Are Often Faulty, Cancer Models, Science, vol. 278, No. 5340, pp. 1041-1042, Nov. 1997.*

Pamuk et al., Spleen tyrosine kinase inhibition in the treatment of autoimmune, allergic and autoinflammatory diseases, Arthritis Research & Therapy, (2010), 12:222, pp. 1-11.*

The International Search Report and Written Opinion, mailed on Mar. 12, 2013, in the corresponding PCT Appl. No. PCT/EP2013/067233.

* cited by examiner

PYRROLO[2,3-B]PYRAZINES AS SYK INHIBITORS

This application is a National Stage Application of PCT/EP2013/067233 filed Aug. 19, 2013, which claims priority from U.S. Provisional Patent Application No. 61/691,384, filed on Aug. 21, 2012. The priority of both said PCT and U.S. Provisional Patent Application are claimed. Each of the prior mentioned applications is hereby incorporated by reference herein in its entirety.

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

SYK (Spleen Tyrosine Kinase) is a non-receptor tyrosine kinase that is essential for B-cell activation through BCR signaling. SYK becomes activated upon binding to phosphorylated BCR and thus initiates the early signaling events following BCR activation. Mice deficient in SYK exhibit an early block in B-cell development. Therefore inhibition of SYK enzymatic activity in cells is proposed as a treatment for autoimmune disease through its effects on autoantibody production.

In addition to the role of SYK in BCR signaling and B-cell activation, it also plays a key role in FcεRI mediated mast cell degranulation and eosinophil activation. Thus, SYK is implicated in allergic disorders including asthma. SYK binds to the phosphorylated gamma chain of FcγRI via its SH2 domains and is essential for downstream signaling. SYK deficient mast cells demonstrate defective degranulation, arachidonic acid and cytokine secretion. This also has been shown for pharmacologic agents that inhibit SYK activity in mast cells. Treatment with SYK antisense oligonucleotides inhibits antigen-induced infiltration of eosinophils and neutrophils in an animal model of asthma. SYK deficient eosinophils also show impaired activation in response to FcεR stimulation. Therefore, small molecule inhibitors of SYK will be useful for treatment of allergy-induced inflammatory diseases including asthma.

In view of the numerous conditions that are contemplated to benefit by treatment involving modulation of the SYK pathway it is immediately apparent that new compounds that modulate the SYK pathway and methods of using these compounds should provide substantial therapeutic benefits to a wide variety of patients. Provided herein are novel compounds for use in the therapeutic treatment of auto-immune and inflammatory diseases by targeting the SYK pathway or by inhibition of SYK kinase.

The application provides a compound of Formula I, II or III

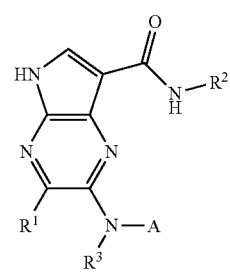

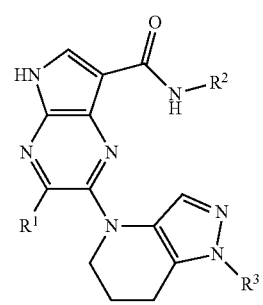

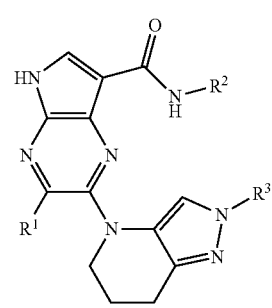

wherein:
$R^1$ is H, halo, or lower alkyl;
$R^2$ is lower alkyl or lower hydroxyalkyl;
$R^3$ is H or lower alkyl;
A is monocyclic or bicyclic heteroaryl (preferably pyridinyl, pyrimidyl, pyrazolyl, isoxazolyl, thiadiazolyl, thiazolyl or pyrazinyl) or phenyl, optionally substituted with one or more A'; and
  each A' is independently lower alkyl, halo, lower alkyl sulfonyl, lower alkyl amide, amido, lower hydroxyalkyl, lower alkoxy, amino lower alkyl, or deuterium;
or a pharmaceutically acceptable salt thereof.

The application provides a method for treating an inflammatory or autoimmune condition comprising administering to a patient in need thereof a therapeutically effective amount of the compound of Formula I.

The application provides a pharmaceutical composition comprising the compound of Formula I, admixed with at least one pharmaceutically acceptable carrier, excipient or diluent.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)"

and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "-----" drawn through a bond each refer to the point of attachment of a functional group or other chemical moiety to the rest of the molecule of which it is a part. Thus, for example:

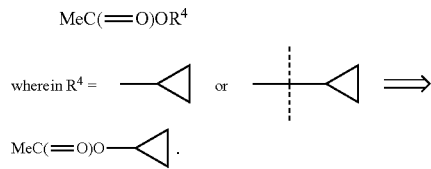

A bond drawn into ring system (as opposed to connected at a distinct vertex) indicates that the bond may be attached to any of the suitable ring atoms The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— $\leftrightarrows$ —C(—OH)=CH—), amide/imidic acid (—C(=O)—NH— $\leftrightarrows$ —C(—OH)=N—) and amidine (—C(=NR)—NH— $\leftrightarrows$ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, $10^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group.

Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below.

The term -(ar)alkyl refers to either an unsubstituted alkyl or an aralkyl group. The term (hetero)aryl or (het)aryl refers to either an aryl or a heteroaryl group.

The term "spirocycloalkyl", as used herein, means a spirocyclic cycloalkyl group, such as, for example, spiro[3.3]heptane. The term spiroheterocycloalkyl, as used herein, means a spirocyclic heterocycloalkyl, such as, for example, 2,6-diaza spiro[3.3]heptane.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R containing 6 carbon atoms. The term "arylcarbonyl" as used herein means a group of formula C(=O)R wherein R is an aryl group; the term "benzoyl" as used herein an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —$CH_2CH(i-Pr)CH_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The terms "haloalkoxy" or "halo-lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The term "lower alkyl amide" as used herein refers to a group of formula CONR$_a$R$_b$ wherein R$_a$ and R$_b$ are independently H and lower alkyl as herein defined.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term "carboxy-alkyl" as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a —CO$_2$H moiety.

The term "heteroaryl" or "heteroaromatic" as used herein means a monocyclic or bicyclic radical of 5 to 12 ring atoms having at least one aromatic or partially unsaturated ring containing four to eight atoms per ring, incorporating one or more N, O, or S heteroatoms, the remaining ring atoms being carbon, with the understanding that the attachment point of the heteroaryl radical will be on an aromatic or partially unsaturated ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, oxazinyl, pyrrolyl, pyrazolyl, imidazolyl, oxazolyl, 4,5-dihydro-oxazolyl, 5,6-Dihydro-4H-[1,3]oxazolyl, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole, naphthyridinyl, 5,6,7,8-Tetrahydro-[1,6]naphthyridinyl, and benzisothiazole. Bicyclic moieties can be optionally substituted on either ring, however the point of attachment is on a ring containing a heteroatom.

The term "heterocyclyl", "heterocycloalkyl" or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N, O or S(O)$_{0-2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof. Examples may also be bicyclic, such as, for example, 3,8-diaza-bicyclo[3.2.1]octane, 2,5-diaza-bicyclo[2.2.2]octane, or octahydro-pyrazino[2,1-c][1,4]oxazine.

Inhibitors of SYK
The application provides a compound of Formula I, II or III

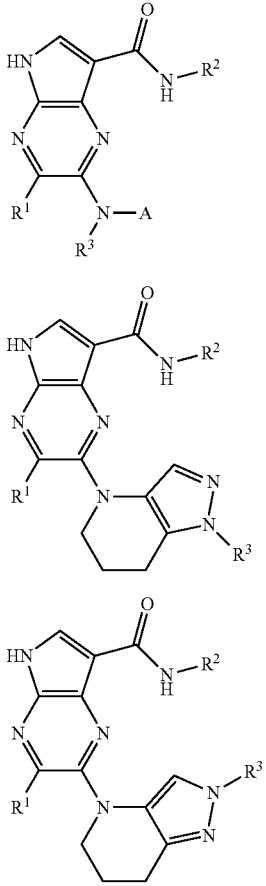

wherein:
R¹ is H, halo, or lower alkyl;
R² is lower alkyl or lower hydroxyalkyl;
R³ is H or lower alkyl;
A is monocyclic or bicyclic heteroaryl (preferably pyridinyl, pyrimidyl, pyrazolyl, isoxazolyl, thiadiazolyl, thiazolyl or pyrazinyl) or phenyl, optionally substituted with one or more A'; and
each A' is independently lower alkyl, halo, lower alkyl sulfonyl, lower alkyl amide, amido, lower hydroxyalkyl, lower alkoxy, amino lower alkyl, or deuterium;
or a pharmaceutically acceptable salt thereof.

In particular, the application provides a compound of Formula I

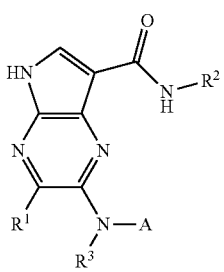

wherein:
R¹ is H, halo, or lower alkyl;
R² is lower alkyl or lower hydroxyalkyl;
R³ is H or lower alkyl;
A is monocyclic or bicyclic heteroaryl (preferably pyridinyl, pyrimidyl, pyrazolyl, isoxazolyl, thiadiazolyl, thiazolyl or pyrazinyl) or phenyl, optionally substituted with one or more A'; and
each A' is independently lower alkyl, halo, lower alkyl sulfonyl, amido, lower hydroxyalkyl, lower alkoxy, amino lower alkyl, or deuterium;
or a pharmaceutically acceptable salt thereof.

The application provides a compound of Formula I, II or III, wherein R³ is lower alkyl.

The application provides a compound of Formula I, II or III, wherein R³ is H.

The application provides a compound of Formula I, II or III, wherein R² is lower alkyl.

The application provides a compound of Formula I, II or III, wherein R³ is H and R² is lower alkyl.

The application provides a compound of Formula I, II or III, wherein R¹ is H.

The application provides a compound of Formula I, II or III, wherein R¹ is H and R³ is H.

The application provides a compound of Formula I, II or III, wherein R¹ is H and R² is lower alkyl.

The application provides a compound of Formula I, II or III, wherein R¹ is H, R³ is H, and R² is lower alkyl.

The application provides a compound of Formula I, wherein A is monocyclic heteroaryl optionally substituted with one or more A'.

The application provides a compound of Formula I, wherein A is monocyclic heteroaryl optionally substituted with one or more A', R¹ is H, R³ is H, and R² is lower alkyl.

The application provides a compound of Formula I, wherein A' is lower alkyl.

The application provides a compound of Formula I, wherein A' is deuterium.

The application provides a compound of Formula I, wherein A is monocyclic heteroaryl optionally substituted with one or more A', R¹ is H, R³ is H, R² is lower alkyl, and A' is lower alkyl.

The application provides a compound of Formula I, wherein A' is lower alkyl sulfonyl.

The application provides a compound of Formula I, wherein A is monocyclic heteroaryl optionally substituted with one or more A', R¹ is H, R³ is H, R² is lower alkyl, and A' is lower alkyl sulfonyl.

The application provides a compound of Formula I, wherein A is phenyl optionally substituted with one or more A'.

The application provides a compound of Formula I, wherein A is phenyl optionally substituted with one or more A', R¹ is H, R³ is H, and R² is lower alkyl.

The application provides a compound of Formula I, wherein A' is lower alkyl or lower alkyl sulfonyl.

The application provides a compound of Formula I, wherein A' is lower alkyl or lower alkyl sulfonyl, A is phenyl optionally substituted with one or more A', R¹ is H, R³ is H, and R² is lower alkyl.

The application provides a compound of Formula I, wherein A is bicyclic heteroaryl optionally substituted with one or more A'.

The application provides a compound of Formula I, wherein A is bicyclic heteroaryl optionally substituted with one or more A', $R^1$ is H, $R^3$ is H, and $R^2$ is lower alkyl.

In a preferred embodiment, the application provides a compound of Formula I, wherein $R^1$ is H; $R^2$ is lower alkyl or lower hydroxyalkyl; $R^3$ is H; A is pyridinyl, pyrimidyl, pyrazolyl, isoxazolyl, thiadiazolyl, thiazolyl, pyrazinyl or phenyl, optionally substituted with one or more A'; and each A' is independently lower alkyl, halo, lower alkyl sulfonyl, lower hydroxyalkyl, lower alkoxy, amino lower alkyl, or deuterium;

or a pharmaceutically acceptable salt thereof.

The application provides a compound selected from the group consisting of:

N-tert-butyl-2-(5-methylpyridin-2-ylamino)-5H-pyrrolo[2,3-b]pyrazine-7-carboxamide;
N-(1-hydroxy-2-methylpropan-2-yl)-2-(5-methylpyridin-2-ylamino)-5H-pyrrolo[2,3-b]pyrazine-7-carboxamide;
N-tert-butyl-2-(1-methyl-1H-pyrazol-3-ylamino)-5H-pyrrolo[2,3-b]pyrazine-7-carboxamide;
N-isopropyl-2-(5-methylpyridin-2-ylamino)-5H-pyrrolo[2,3-b]pyrazine-7-carboxamide;
N-tert-butyl-2-(1-methyl-1H-pyrazol-4-ylamino)-5H-pyrrolo[2,3-b]pyrazine-7-carboxamide;
N-tert-butyl-2-(6-methylpyridin-3-ylamino)-5H-pyrrolo[2,3-b]pyrazine-7-carboxamide;
N-tert-butyl-2-(2-methylpyrimidin-5-ylamino)-5H-pyrrolo[2,3-b]pyrazine-7-carboxamide;
N-tert-butyl-2-(5-methylpyrazin-2-ylamino)-5H-pyrrolo[2,3-b]pyrazine-7-carboxamide;
N-tert-butyl-2-(3-methyl-1H-pyrazol-5-ylamino)-5H-pyrrolo[2,3-b]pyrazine-7-carboxamide;
N-tert-butyl-2-(pyridin-3-ylamino)-5H-pyrrolo[2,3-b]pyrazine-7-carboxamide;
N-tert-butyl-2-(2-fluoro-4-methylphenylamino)-5H-pyrrolo[2,3-b]pyrazine-7-carboxamide;
N-tert-butyl-2-(p-tolylamino)-5H-pyrrolo[2,3-b]pyrazine-7-carboxamide;
N-tert-butyl-2-(3-(methylsulfonyl)phenylamino)-5H-pyrrolo[2,3-b]pyrazine-7-carboxamide;
N-tert-butyl-2-(1-ethyl-1H-pyrazol-4-ylamino)-5H-pyrrolo[2,3-b]pyrazine-7-carboxamide;
N-tert-butyl-2-(2-(dimethylcarbamoyl)phenylamino)-5H-pyrrolo[2,3-b]pyrazine-7-carboxamide;
N-tert-butyl-2-(1,5-dimethyl-1H-pyrazol-4-ylamino)-5H-pyrrolo[2,3-b]pyrazine-7-carboxamide;
N-(1-hydroxy-2-methylpropan-2-yl)-2-(1-methyl-1H-pyrazol-4-ylamino)-5H-pyrrolo[2,3-b]pyrazine-7-carboxamide;
N-tert-butyl-2-(3-methylisothiazol-5-ylamino)-5H-pyrrolo[2,3-b]pyrazine-7-carboxamide;
N-tert-butyl-2-(2,4-dimethylphenylamino)-5H-pyrrolo[2,3-b]pyrazine-7-carboxamide;
N-tert-butyl-2-(4-(methylsulfonyl)phenylamino)-5H-pyrrolo[2,3-b]pyrazine-7-carboxamide;
N-tert-butyl-2-(methyl(pyridin-3-yl)amino)-5H-pyrrolo[2,3-b]pyrazine-7-carboxamide;
N-tert-butyl-2-(3-methylisoxazol-5-ylamino)-5H-pyrrolo[2,3-b]pyrazine-7-carboxamide;
N-tert-butyl-2-(6-(methylsulfonyl)pyridin-3-ylamino)-5H-pyrrolo[2,3-b]pyrazine-7-carboxamide;
N-tert-butyl-2-(3-(1-hydroxyethyl)phenylamino)-5H-pyrrolo[2,3-b]pyrazine-7-carboxamide;
N-tert-butyl-2-(2-methoxypyrimidin-5-ylamino)-5H-pyrrolo[2,3-b]pyrazine-7-carboxamide;
N-(1-hydroxy-2-methylpropan-2-yl)-2-(pyridin-3-ylamino)-5H-pyrrolo[2,3-b]pyrazine-7-carboxamide;
2-(3-(1-aminoethyl)phenylamino)-N-tert-butyl-5H-pyrrolo[2,3-b]pyrazine-7-carboxamide;
N-tert-butyl-2-(2-(methylsulfonyl)pyridin-4-ylamino)-5H-pyrrolo[2,3-b]pyrazine-7-carboxamide;
N-tert-butyl-2-(5-(methylsulfonyl)pyridin-3-ylamino)-5H-pyrrolo[2,3-b]pyrazine-7-carboxamide;
N-tert-butyl-2-(1,3-dimethyl-1H-pyrazol-4-ylamino)-5H-pyrrolo[2,3-b]pyrazine-7-carboxamide;
N-tert-butyl-2-(3-methyl-1,2,4-thiadiazol-5-ylamino)-5H-pyrrolo[2,3-b]pyrazine-7-carboxamide;
N-tert-butyl-2-(2-methyl-6,7-dihydro-2H-pyrazolo[4,3-b]pyridin-4(5H)-yl)-5H-pyrrolo[2,3-b]pyrazine-7-carboxamide;
N-tert-butyl-2-(1-methyl-6,7-dihydro-1H-pyrazolo[4,3-b]pyridin-4(5H)-yl)-5H-pyrrolo[2,3-b]pyrazine-7-carboxamide;
3-Methyl-2-(1-methyl-1H-pyrazol-4-ylamino)-5H-pyrrolo[2,3-b]pyrazine-7-carboxylic acid tert-butylamide;
2-(3-Methanesulfonyl-phenylamino)-3-methyl-5H-pyrrolo[2,3-b]pyrazine-7-carboxylic acid tert-butylamide;
3-Methyl-2-(3-methyl-isothiazol-5-ylamino)-5H-pyrrolo[2,3-b]pyrazine-7-carboxylic acid tert-butylamide;
2-Phenylamino(D5)-5H-pyrrolo[2,3-b]pyrazine-7-carboxylic acid tert-butylamide; and
N-tert-butyl-3-chloro-2-(3-methylisothiazol-5-ylamino)-5H-pyrrolo[2,3-b]pyrazine-7-carboxamide.

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for treating an inflammatory condition comprising co-administering to a patient in need thereof a therapeutically effective amount of an anti-inflammatory compound in combination with the compound of Formula I.

The application provides a method for treating an immune disorder comprising co-administering to a patient in need thereof a therapeutically effective amount of an immunosuppressant compound in combination with the compound of Formula I.

The application provides a pharmaceutical composition comprising the compound of Formula I, admixed with at least one pharmaceutically acceptable carrier, excipient or diluent.

The application provides the above pharmaceutical composition, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

The application provides the use of the compound of formula I for the manufacture of a medicament useful for the treatment of disorders associated with Syk.

The application provides the use of the compound of formula I for the manufacture of a medicament useful for the treatment of rheumatoid arthritis.

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this application is based on AUTONOM™ v.4.0, a Beilstein Institute computerized system or Struct=Name, a CambridgeSoft® application, for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of compounds according to generic Formula I.

TABLE I

| Compound | Nomenclature | Structure |
|---|---|---|
| I-1 | N-tert-butyl-2-(5-methylpyridin-2-ylamino)-5H-pyrrolo[2,3-b]pyrazine-7-carboxamide | 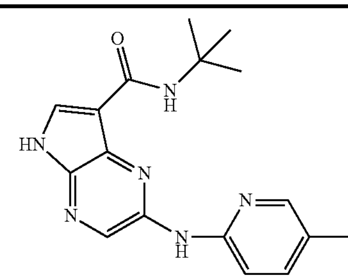 |
| I-2 | N-(1-hydroxy-2-methylpropan-2-yl)-2-(5-methylpyridin-2-ylamino)-5H-pyrrolo[2,3-b]pyrazine-7-carboxamide | 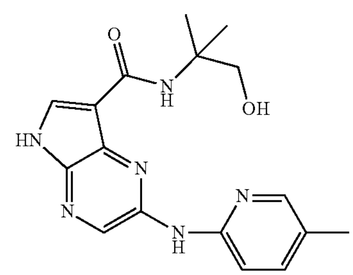 [SMILES: Cc1ccc(Nc2cnc3[nH]cc(C(=O)NC(C)(C)CO)c3n2)nc1] |
| I-3 | N-tert-butyl-2-(1-methyl-1H-pyrazol-3-ylamino)-5H-pyrrolo[2,3-b]pyrazine-7-carboxamide | 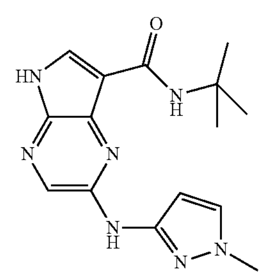 [SMILES: Cn1ccc(Nc2cnc3[nH]cc(C(=O)NC(C)(C)C)c3n2)n1] |
| I-4 | N-isopropyl-2-(5-methylpyridin-2-ylamino)-5H-pyrrolo[2,3-b]pyrazine-7-carboxamide | 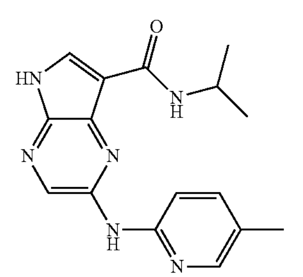 [SMILES: Cc1ccc(Nc2cnc3[nH]cc(C(=O)NC(C)C)c3n2)nc1] |

TABLE I-continued

| Compound | Nomenclature | Structure |
|---|---|---|
| I-5 | N-tert-butyl-2-(1-methyl-1H-pyrazol-4-ylamino)-5H-pyrrolo[2,3-b]pyrazine-7-carboxamide | 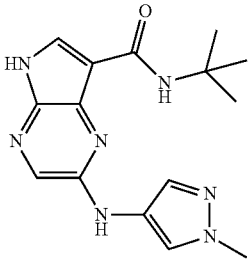 [SMILES: Cn1cc(Nc2cnc3[nH]cc(C(=O)NC(C)(C)C)c3n2)cn1] |
| I-6 | N-tert-butyl-2-(6-methylpyridin-3-ylamino)-5H-pyrrolo[2,3-b]pyrazine-7-carboxamide | 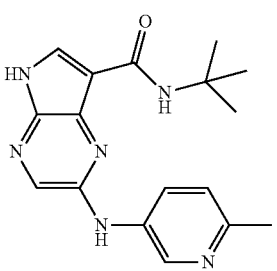 [SMILES: Cc1ccc(Nc2cnc3[nH]cc(C(=O)NC(C)(C)C)c3n2)cn1] |
| I-7 | N-tert-butyl-2-(2-methylpyrimidin-5-ylamino)-5H-pyrrolo[2,3-b]pyrazine-7-carboxamide | 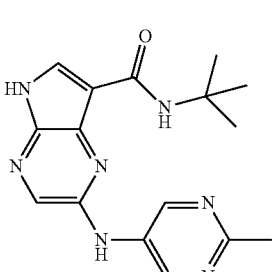 |
| I-8 | N-tert-butyl-2-(5-methylpyrazin-2-ylamino)-5H-pyrrolo[2,3-b]pyrazine-7-carboxamide | 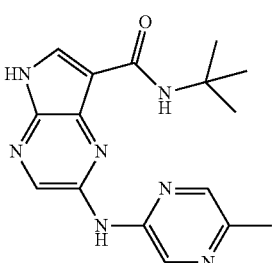 |
| I-9 | N-tert-butyl-2-(3-methyl-1H-pyrazol-5-ylamino)-5H-pyrrolo[2,3-b]pyrazine-7-carboxamide | 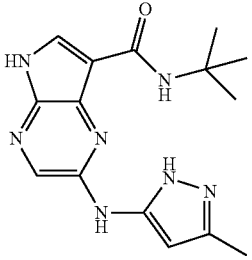 [SMILES: Cc1cc(Nc2cnc3[nH]cc(C(=O)NC(C)(C)C)c3n2)[nH]n1] |

TABLE I-continued

| Compound | Nomenclature | Structure |
|---|---|---|
| I-10 | N-tert-butyl-2-(pyridin-3-ylamino)-5H-pyrrolo[2,3-b]pyrazine-7-carboxamide | 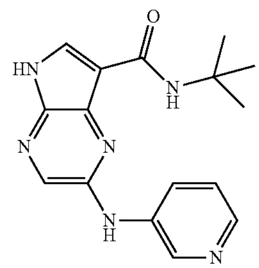 [SMILES: CC(C)(C)NC(=O)c1c[nH]c2ncc(Nc3cccnc3)nc12] |
| I-11 | N-tert-butyl-2-(2-fluoro-4-methylphenylamino)-5H-pyrrolo[2,3-b]pyrazine-7-carboxamide | 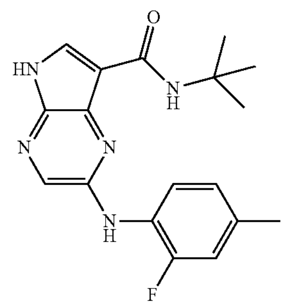 [SMILES: Cc1ccc(Nc2cnc3[nH]cc(C(=O)NC(C)(C)C)c3n2)c(F)c1] |
| I-12 | N-tert-butyl-2-(p-tolylamino)-5H-pyrrolo[2,3-b]pyrazine-7-carboxamide | 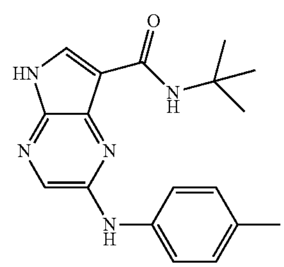 [SMILES: Cc1ccc(Nc2cnc3[nH]cc(C(=O)NC(C)(C)C)c3n2)cc1] |
| I-13 | N-tert-butyl-2-(3-(methylsulfonyl)phenylamino)-5H-pyrrolo[2,3-b]pyrazine-7-carboxamide | 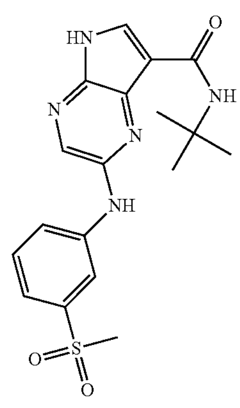 [SMILES: CC(C)(C)NC(=O)c1c[nH]c2ncc(Nc3cccc(S(C)(=O)=O)c3)nc12] |
| I-14 | N-tert-butyl-2-(1-ethyl-1H-pyrazol-4-ylamino)-5H-pyrrolo[2,3-b]pyrazine-7-carboxamide | 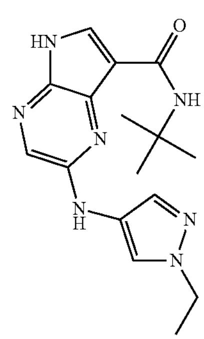 [SMILES: CCn1cc(Nc2cnc3[nH]cc(C(=O)NC(C)(C)C)c3n2)cn1] |

TABLE I-continued

| Compound | Nomenclature |
|---|---|
| I-15 | N-tert-butyl-2-(2-(dimethylcarbamoyl)phenylamino)-5H-pyrrolo[2,3-b]pyrazine-7-carboxamide |
| I-16 | N-tert-butyl-2-(1,5-dimethyl-1H-pyrazol-4-ylamino)-5H-pyrrolo[2,3-b]pyrazine-7-carboxamide |
| I-17 | N-(1-hydroxy-2-methylpropan-2-yl)-2-(1-methyl-1H-pyrazol-4-ylamino)-5H-pyrrolo[2,3-b]pyrazine-7-carboxamide |
| I-18 | N-tert-butyl-2-(3-methylisothiazol-5-ylamino)-5H-pyrrolo[2,3-b]pyrazine-7-carboxamide |
| I-19 | N-tert-butyl-2-(2,4-dimethylphenylamino)-5H-pyrrolo[2,3-b]pyrazine-7-carboxamide |

TABLE I-continued

| Compound | Nomenclature | Structure |
|---|---|---|
| I-20 | N-tert-butyl-2-(4-(methylsulfonyl)phenylamino)-5H-pyrrolo[2,3-b]pyrazine-7-carboxamide | 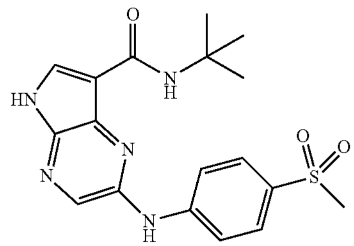 [SMILES: CC(C)(C)NC(=O)c1c[nH]c2ncc(Nc3ccc(S(C)(=O)=O)cc3)nc12] |
| I-21 | N-tert-butyl-2-(methyl(pyridin-3-yl)amino)-5H-pyrrolo[2,3-b]pyrazine-7-carboxamide | 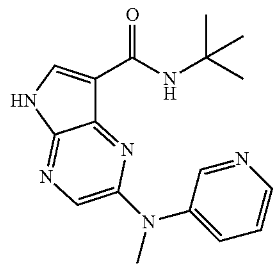 [SMILES: CN(c1cccnc1)c1cnc2[nH]cc(C(=O)NC(C)(C)C)c2n1] |
| I-22 | N-tert-butyl-2-(3-methylisoxazol-5-ylamino)-5H-pyrrolo[2,3-b]pyrazine-7-carboxamide | 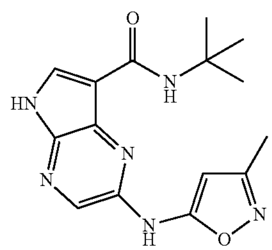 [SMILES: Cc1cc(Nc2cnc3[nH]cc(C(=O)NC(C)(C)C)c3n2)on1] |
| I-23 | N-tert-butyl-2-(6-(methylsulfonyl)pyridin-3-ylamino)-5H-pyrrolo[2,3-b]pyrazine-7-carboxamide | 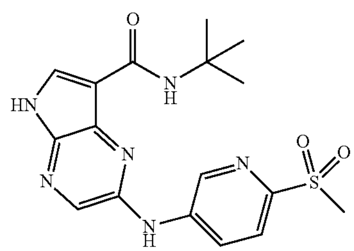 [SMILES: CC(C)(C)NC(=O)c1c[nH]c2ncc(Nc3ccc(S(C)(=O)=O)nc3)nc12] |
| I-24 | N-tert-butyl-2-(3-(1-hydroxyethyl)phenylamino)-5H-pyrrolo[2,3-b]pyrazine-7-carboxamide | 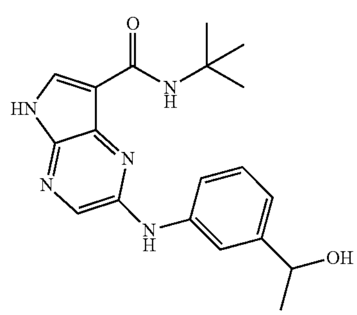 [SMILES: CC(O)c1cccc(Nc2cnc3[nH]cc(C(=O)NC(C)(C)C)c3n2)c1] |
| I-25 | N-tert-butyl-2-(2-methoxypyrimidin-5-ylamino)-5H-pyrrolo[2,3-b]pyrazine-7-carboxamide | 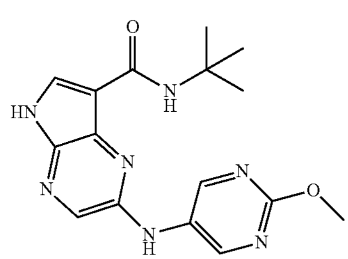 [SMILES: COc1ncc(Nc2cnc3[nH]cc(C(=O)NC(C)(C)C)c3n2)cn1] |

TABLE I-continued

| Compound | Nomenclature | Structure |
|---|---|---|
| I-26 | N-(1-hydroxy-2-methylpropan-2-yl)-2-(pyridin-3-ylamino)-5H-pyrrolo[2,3-b]pyrazine-7-carboxamide | 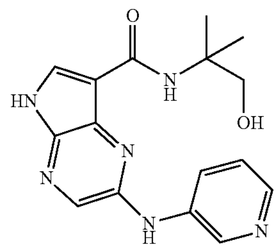 [SMILES: CC(C)(CO)NC(=O)c1c[nH]c2ncc(Nc3cccnc3)nc12] |
| I-27 | 2-(3-(1-aminoethyl)phenylamino)-N-tert-butyl-5H-pyrrolo[2,3-b]pyrazine-7-carboxamide | 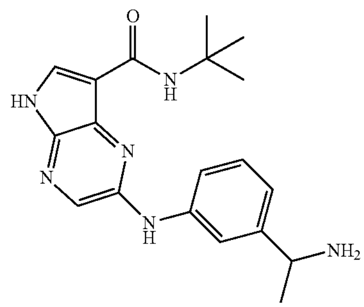 [SMILES: CC(N)c1cccc(Nc2cnc3[nH]cc(C(=O)NC(C)(C)C)c3n2)c1] |
| I-28 | N-tert-butyl-2-(2-(methylsulfonyl)pyridin-4-ylamino)-5H-pyrrolo[2,3-b]pyrazine-7-carboxamide | 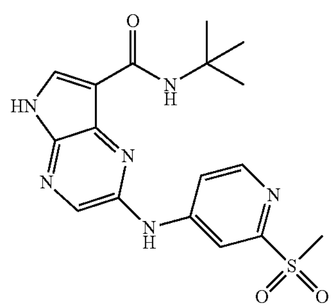 [SMILES: CC(C)(C)NC(=O)c1c[nH]c2ncc(Nc3ccnc(S(C)(=O)=O)c3)nc12] |
| I-29 | N-tert-butyl-2-(5-(methylsulfonyl)pyridin-3-ylamino)-5H-pyrrolo[2,3-b]pyrazine-7-carboxamide | 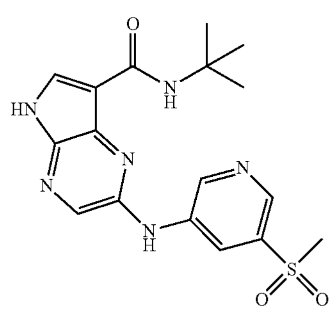 [SMILES: CC(C)(C)NC(=O)c1c[nH]c2ncc(Nc3cncc(S(C)(=O)=O)c3)nc12] |
| I-30 | N-tert-butyl-2-(1,3-dimethyl-1H-pyrazol-4-ylamino)-5H-pyrrolo[2,3-b]pyrazine-7-carboxamide | 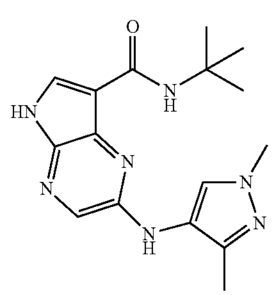 [SMILES: Cc1nn(C)cc1Nc1cnc2[nH]cc(C(=O)NC(C)(C)C)c2n1] |

TABLE I-continued

| Compound | Nomenclature | Structure |
|---|---|---|
| I-31 | N-tert-butyl-2-(3-methyl-1,2,4-thiadiazol-5-ylamino)-5H-pyrrolo[2,3-b]pyrazine-7-carboxamide | 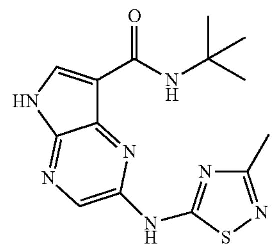 [SMILES: Cc1nsc(Nc2cnc3[nH]cc(C(=O)NC(C)(C)C)c3n2)n1] |
| I-32 | N-tert-butyl-2-(2-methyl-6,7-dihydro-2H-pyrazolo[4,3-b]pyridin-4(5H)-yl)-5H-pyrrolo[2,3-b]pyrazine-7-carboxamide | 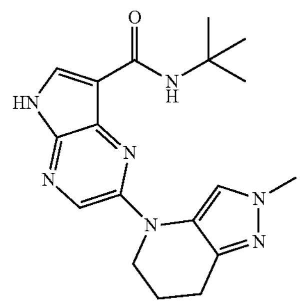 [SMILES: Cn1cc2c(n1)CCCN2c1cnc2[nH]cc(C(=O)NC(C)(C)C)c2n1] |
| I-33 | N-tert-butyl-2-(1-methyl-6,7-dihydro-1H-pyrazolo[4,3-b]pyridin-4(5H)-yl)-5H-pyrrolo[2,3-b]pyrazine-7-carboxamide | 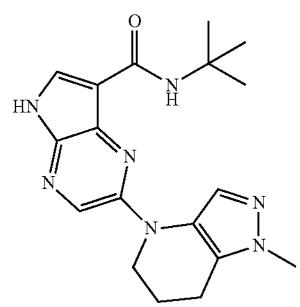 [SMILES: Cn1ncc2c1CCCN2c1cnc2[nH]cc(C(=O)NC(C)(C)C)c2n1] |
| I-34 | 3-Methyl-2-(1-methyl-1H-pyrazol-4-ylamino)-5H-pyrrolo[2,3-b]pyrazine-7-carboxylic acid tert-butylamide | 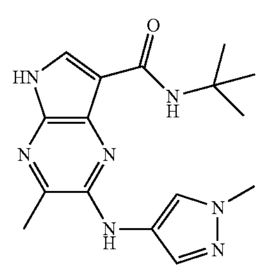 [SMILES: Cc1nc2[nH]cc(C(=O)NC(C)(C)C)c2nc1Nc1cnn(C)c1] |
| I-35 | 2-(3-Methanesulfonyl-phenylamino)-3-methyl-5H-pyrrolo[2,3-b]pyrazine-7-carboxylic acid tert-butylamide | 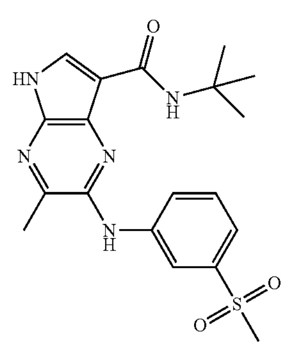 [SMILES: Cc1nc2[nH]cc(C(=O)NC(C)(C)C)c2nc1Nc1cccc(S(C)(=O)=O)c1] |

TABLE I-continued

| Compound | Nomenclature | Structure |
|---|---|---|
| I-36 | 3-Methyl-2-(3-methyl-isothiazol-5-ylamino)-5H-pyrrolo[2,3-b]pyrazine-7-carboxylic acid tert-butylamide | 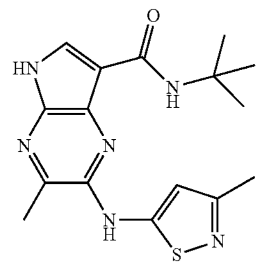 [SMILES: Cc1cc(Nc2nc3c(C(=O)NC(C)(C)C)c[nH]c3nc2C)sn1] |
| I-37 | 2-Phenylamino(D5)-5H-pyrrolo[2,3-b]pyrazine-7-carboxylic acid tert-butylamide | 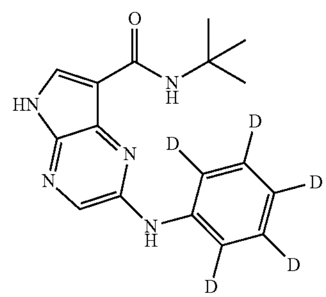 [SMILES: [2H]c1c([2H])c([2H])c(Nc2cnc3[nH]cc(C(=O)NC(C)(C)C)c3n2)c([2H])c1[2H]] |
| I-38 | N-tert-butyl-3-chloro-2-(3-methylisothiazol-5-ylamino)-5H-pyrrolo[2,3-b]pyrazine-7-carboxamide | 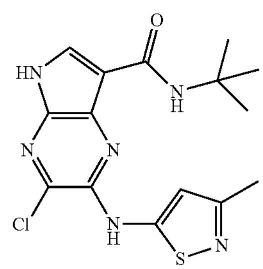 [SMILES: Cc1cc(Nc2nc3c(C(=O)NC(C)(C)C)c[nH]c3nc2Cl)sn1] |

Synthesis

General Schemes

In the General Schemes below, $R^2$ can be lower alkyl or lower hydroxyalkyl; A can be monocyclic or bicyclic heteroaryl or phenyl, optionally substituted with one or more A'; and each A' can be independently lower alkyl, halo, lower alkyl sulfonyl, amido, lower hydroxyalkyl, lower alkoxy, amino lower alkyl, or deuterium.

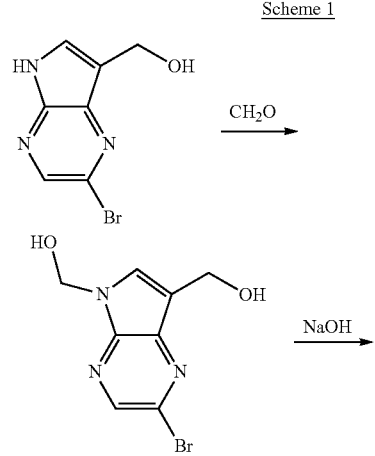

Scheme 1

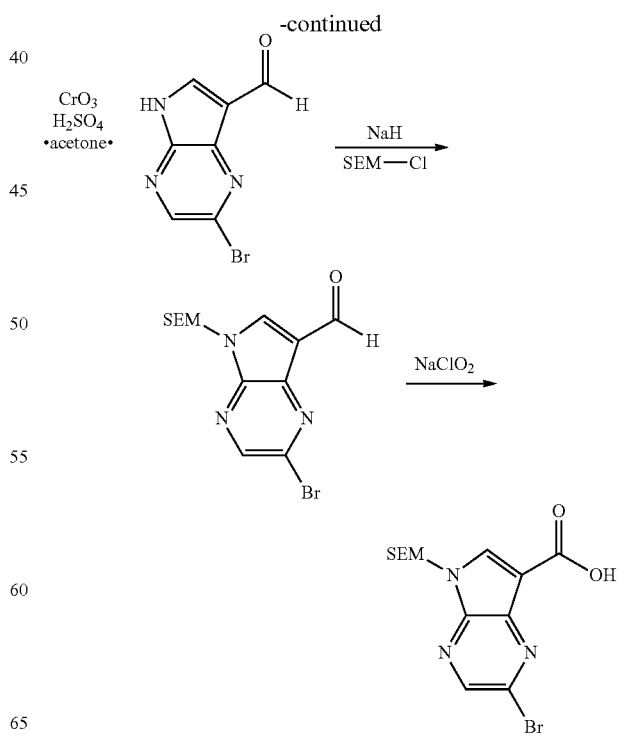

Scheme 2

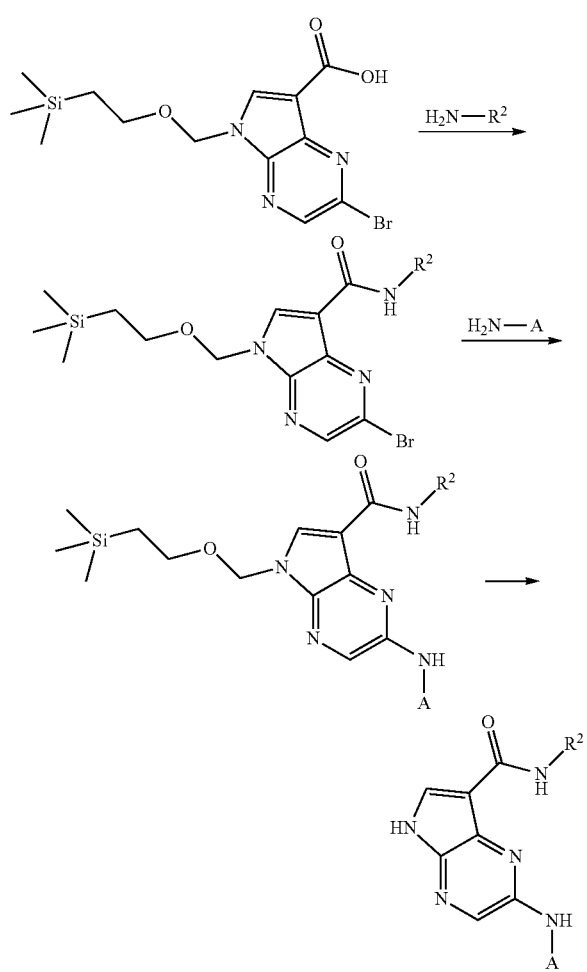

Pharmaceutical Compositions and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
|---|---|
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | Grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 h.

Indications and Methods of Treatment

The compounds described herein are kinase inhibitors, in particular SYK inhibitors. These inhibitors can be useful for treating one or more diseases responsive to kinase inhibition, including diseases responsive to SYK inhibition and/or inhibition of B-cell proliferation, in mammals. Without wishing to be bound to any particular theory, it is believed that the interaction of the compounds of the invention with SYK results in the inhibition of SYK activity and thus in the pharmaceutical utility of these compounds. Accordingly, the invention includes a method of treating a mammal, for instance a human, having a disease responsive to inhibition of SYK activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to SYK include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for treating an inflammatory condition comprising co-administering to a patient in need thereof a therapeutically effective amount of an anti-inflammatory compound in combination with the compound of Formula I.

The application provides a method for treating an immune disorder comprising co-administering to a patient in need thereof a therapeutically effective amount of an immunosuppressant compound in combination with the compound of Formula I.

EXAMPLES

Abbreviations

Commonly used abbreviations include: acetyl (Ac), azo-bis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether (Et₂O), ethyl isopropyl ether (EtOiPr), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), MeSO₂— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl) palladium(II) (Pd(dppf)Cl₂), palladium(II) acetate (Pd(OAc)₂), tris(dibenzylideneacetone)dipalladium(0) (Pd₂(dba)₃), pyridinium dichromate (PDC), phenyl (Ph), propyl (Pr), iso-propyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-BuMe₂Si (TBDMS), tetra-n-butylammonium fluoride (TBAF), triethylamine (TEA or Et₃N), 2,2,6,6-tetramethylpiperidine 1-oxyl (TEMPO), triflate or CF₃SO₂— (TO, trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me₃Si (TMS), p-toluenesulfonic acid monohydrate (TsOH or pTsOH), 4-Me-C₆H₄SO₂— or tosyl (Ts), and N-urethane-N-carboxyanhydride (UNCA). Conventional nomenclature including the prefixes normal (n), iso (i-), secondary (sec-), tertiary (ten-) and neo have their customary meaning when used with an alkyl moiety. (J. Rigaudy and D. P. Klesney, Nomenclature in Organic Chemistry, IUPAC 1979 Pergamon Press, Oxford.).

General Conditions.

Unless otherwise stated, all temperatures including melting points (i.e., MP) are in degrees Celsius (° C.). It should be appreciated that the reaction which produces the indicated and/or desired product may not necessarily result directly from the combination of two reagents which were initially added, i.e., there may be one or more intermediates which are produced in the mixture which ultimately leads to the formation of the indicated and/or the desired product. The preceding abbreviations may be used in the Preparations and Examples. All names were generated using Autonom or ChemDraw.

The following preparations and examples are given to enable those skilled in the art to more clearly understand and to practice the present invention. They should not be considered as limiting the scope of the invention, but merely as being illustrative and representative thereof.

Preparative Examples

Example 1

Procedure 1

2-Bromo-5-(2-trimethylsilanyl-ethoxymethyl)-5H-pyrrolo[2,3-b]pyrazine-7-carbaldehyde

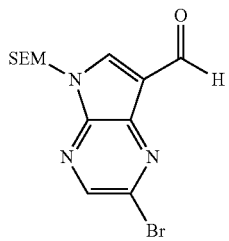 [SMILES: C[Si](C)(C)CCOCn1cc(C=O)c2nc(Br)cnc21]

Method A
Step 1

(2-Bromo-7-hydroxymethyl-pyrrolo[2,3-b]pyrazin-5-yl)-methanol

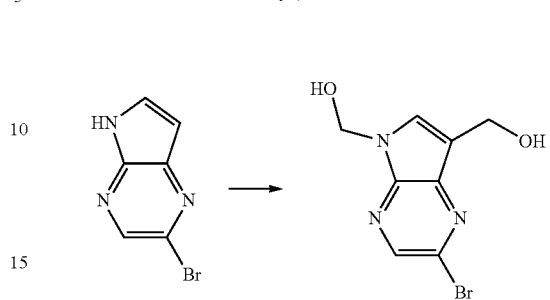

To a partial suspension of 2-bromo-5H-pyrrolo[2,3-b]pyrazine (5.0 g, 25.2 mmol) in 1,4-dioxane (100 mL) was added 2.0 M aqueous NaOH (25 mL, 50.0 mmol) and 37% aqueous formaldehyde (19 mL, 252 mmol). The dark homogenous reaction mixture was stirred at room temperature overnight. The organics were evaporated under reduced pressure. The aqueous layer was neutralized with 1.0 M HCl and extracted with EtOAc (2×). The combined organics were concentrated to afford 2.6 g of an orange solid. Upon standing, a thick brown precipitate formed in the aqueous layer. The precipitate was collected by filtration and dried. The brown solid was extracted with hot 10% MeOH/EtOAc (3×200 mL). The extracts were combined and evaporated to provide an additional 3.05 g of orange solid. Overall yield was 5.65 g (87%) of (2-bromo-7-hydroxymethyl-pyrrolo[2,3-b]pyrazin-5-yl)-methanol. ¹H NMR (DMSO-d₆, 400 MHz): δ (ppm) 8.43 (s, 1H), 7.96 (s, 1H), 6.71 (t, J=7.3 Hz, 1H), 5.59 (d, J=7.6 Hz, 2H), 5.10 (t, J=5.3 Hz, 1H), 4.66 (d, J=5.6 Hz, 2H).

Step 2

(2-Bromo-5H-pyrrolo[2,3-b]pyrazin-7-yl)-methanol

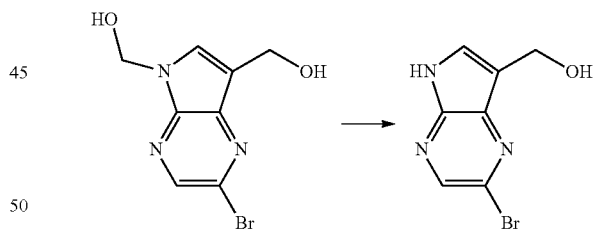

To a suspension of (2-bromo-7-hydroxymethyl-pyrrolo[2,3-b]pyrazin-5-yl)-methanol (5.65 g, 21.9 mmol) in THF (150 mL) was added a solution of 2.0 M aqueous NaOH (33 mL, 66 mmol). The homogeneous reaction mixture was stirred overnight then the organics were removed under reduced pressure. The aqueous residue was brought to pH 4 with 1.0 M aqueous HCl. The resulting precipitate was collected via filtration and rinsed with H₂O to afford 3.68 g of a yellow solid. The filtrate was extracted with EtOAc (2×) and the organics were concentrated under reduced pressure to provide an additional 0.92 g of yellow solid. Overall yield was 4.60 g (92%) of (2-bromo-5H-pyrrolo[2,3-b]pyrazin-7-yl)-methanol. ¹H NMR (DMSO-d₆, 300 MHz): δ (ppm) 12.19 (br. s., 1H), 8.33 (s, 1H), 7.85 (s, 1H), 4.96 (t, J=5.3 Hz, 1H), 4.62 (d, J=4.9 Hz, 2H).

Step 3

2-Bromo-5-(2-trimethylsilanyl-ethoxymethyl)-5H-pyrrolo[2,3-b]pyrazine-7-carbaldehyde

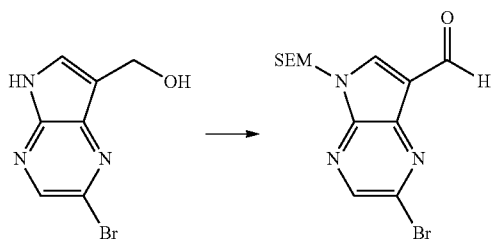 [SMILES: OCc1c[nH]c2ncc(Br)nc12 ; C[Si](C)(C)CCOCn1cc(C=O)c2nc(Br)cnc21]

A stock solution of Jones reagent (2.67 M) was prepared by carefully adding concentrated H$_2$SO$_4$ (2.3 mL) to CrO$_3$ (2.67 g) then diluting to 10 mL with H$_2$O. To a partial suspension of (2-bromo-5H-pyrrolo[2,3-b]pyrazin-7-yl)-methanol (4.6 g, 20.1 mmol) in acetone (300 mL) was slowly added Jones reagent (9 mL, 24.0 mmol). During the addition the starting material gradually dissolved and a thick green precipitate was formed. The reaction mixture was stirred for 15 min then quenched with i-PrOH (2 mL) and filtered over Celite, rinsing with acetone. The filtrate was concentrated to provide 4.76 g of 2-bromo-5H-pyrrolo[2,3-b]pyrazine-7-carbaldehyde as a yellow-orange solid that was used without further purification. To a solution of this solid in DMF (50 mL) at 0° C. was added NaH (60% in mineral oil, 1.2 g, 30.1 mmol). The reaction mixture was stirred at room temperature for 30 min then cooled back to 0° C. and 2-(trimethylsilyl)ethoxymethyl chloride (4.3 mL, 24.1 mmol) was slowly added. The reaction mixture was warmed to room temperature and stirred for 1 h then quenched with H$_2$O and extracted with EtOAc (3×). The combined organics were washed with H$_2$O (3×) and brine then dried over MgSO$_4$ and concentrated. The residue was purified by SiO$_2$ chromatography (20% to 30% EtOAc/hexanes) to isolate 3.82 g (53%) of 2-bromo-5-(2-trimethylsilanyl-ethoxymethyl)-5H-pyrrolo[2,3-b]pyrazine-7-carbaldehyde as a yellow solid. $^1$H NMR (CDCl$_3$, 300 MHz): δ (ppm) 10.37 (s, 1H), 8.50 (s, 1H), 8.33 (s, 1H), 5.73 (s, 2H), 3.53-3.70 (m, 2H), 0.90-1.05 (m, 2H), 0.00 (s, 9H).

Method B
Step 1

2-Bromo-5-(2-trimethylsilanyl-ethoxymethyl)-5H-pyrrolo[2,3-b]pyrazine

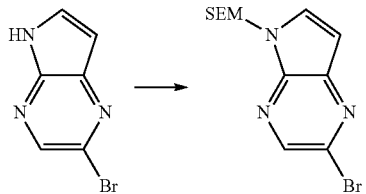 [SMILES: Brc1cnc2[nH]ccc2n1 ; C[Si](C)(C)CCOCn1ccc2nc(Br)cnc21]

In a dry round-bottomed flask, 2-bromo-5H-pyrrolo[2,3-b]pyrazine (5.0 g, 25.2 mmol) was dissolved in DMF (50 mL). The reaction mixture was cooled to 0° C. and sodium hydride (60% dispersion in mineral oil, 1.22 g, 30.6 mmol). The reaction mixture was warmed to room temperature and stirred for 15 min then cooled back to 0° C. and SEM-Cl (5.4 mL, 30.4 mmol) was slowly added. After the addition was complete, the ice bath was removed and the reaction mixture was stirred at room temperature for 1.5 h. The reaction mixture was quenched with 50 mL water and extracted with 150 mL diethyl ether (2×). The combined organic layers were washed twice with 30 mL water and once with 30 mL brine then dried over sodium sulfate, filtered and concentrated. The residue was absorbed on ~20 g SiO$_2$ and chromatographed over 200 g SiO$_2$ with EtOAc/Hexanes (gradient: 0-15% EtOAc). All fractions containing product were combined and concentrated to afford 2-bromo-5-(2-trimethylsilanyl-ethoxymethyl)-5H-pyrrolo[2,3-b]pyrazine (6.61 g, 80%) as a pale yellow oil which gradually solidified. $^1$H NMR (CDCl$_3$, 300 MHz): δ (ppm) 8.38 (s, 1H), 7.70 (d, J=3.8 Hz, 1H), 6.76 (d, J=3.8 Hz, 1H), 5.68 (s, 2H), 3.50-3.65 (m, 2H), 0.88-1.03 (m, 2H), 0.00 (s, 9H).

Step 2

2-Bromo-5-(2-trimethylsilanyl-ethoxymethyl)-5H-pyrrolo[2,3-b]pyrazine-7-carbaldehyde

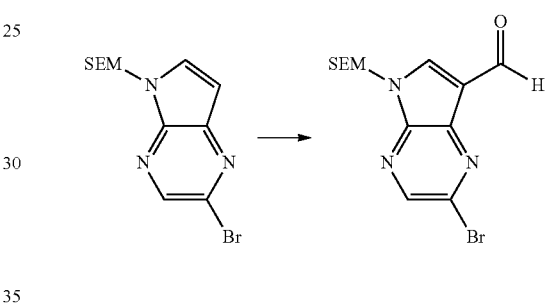

In a round-bottomed flask, 2-bromo-5-(2-trimethylsilanyl-ethoxymethyl)-5H-pyrrolo[2,3-b]pyrazine (6.58 g, 20.0 mmol) was dissolved in chloroform (pentene stabilized, 120 mL) and chloromethylenedimethyliminium chloride (10.3 g, 80.2 mmol) was added. The reaction mixture was stirred at reflux for 8 h as a steady stream of nitrogen gas was bubbled through the reaction mixture. The dark brown solution was cooled to room temperature and stirred overnight. The reaction mixture was carefully quenched with ~100 mL saturated NaHCO$_3$-solution (caution: exothermic) and then extracted twice with 200 mL diethyl ether. The organic layers were combined, dried over sodium sulfate, filtered and concentrated. The residue was absorbed on ~20 g SiO$_2$ and chromatographed over 200 g SiO$_2$ with EtOAc/Hexanes (gradient: 0-25% EtOAc). All fractions containing product were combined and concentrated to afford 5.92 g (83%) of an approx. 3:1 mixture of 2-bromo-5-(2-trimethylsilanyl-ethoxymethyl)-5H-pyrrolo[2,3-b]pyrazine-7-carbaldehyde and 2-chloro-5-(2-trimethylsilanyl-ethoxymethyl)-5H-pyrrolo[2,3-b]pyrazine-7-carbaldehyde as a yellow solid. Bromide: $^1$H NMR (CDCl$_3$, 300 MHz): δ (ppm) 10.37 (s, 1H), 8.50 (s, 1H), 8.33 (s, 1H), 5.73 (s, 2H), 3.56-3.67 (m, 2H), 0.91-1.02 (m, 2H), 0.00 (s, 9H); Chloride: $^1$H NMR (CDCl$_3$, 300 MHz): δ (ppm) 10.36 (s, 1H), 8.41 (s, 1H), 8.35 (s, 1H), 5.74 (s, 2H), 3.56-3.67 (m, 2H), 0.91-1.02 (m, 2H), 0.00 (s, 9H).

Procedure 2

2-Bromo-5-(2-trimethylsilanylethoxymethyl)-5H-pyrrolo[2,3-b]pyrazine-7-carboxylic acid

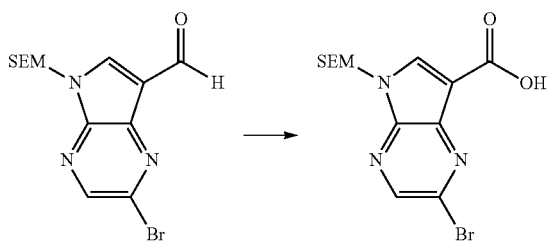 [SMILES: C[Si](C)(C)CCOCn1cc(C=O)c2nc(Br)cnc21 ; C[Si](C)(C)CCOCn1cc(C(=O)O)c2nc(Br)cnc21]

In a flask 2-bromo-5-(2-trimethylsilanylethoxymethyl)-5H-pyrrolo[2,3-b]pyrazine-7-carbaldehyde (3.11 g, 8.74 mmol) was dissolved in dioxane (120 mL) and H$_2$O (30 mL) and the mixture cooled at 0° C. Sulfamic acid (5.09 g, 52.4 mmol) was added, followed by a solution of sodium chlorite (1.28 g, 11.4 mmol) and potassium dihydrogen phosphate (14.3 g, 104.9 mmol) in H$_2$O (75 mL) via an addition funnel over 15 min. The mixture was allowed to warm to room temperature over 2 h. The resulting yellow solid was filtered off, washed with H$_2$O and hexane and dried. The filtrate was then extracted with EtOAc, and the combined organics washed with brine, dried over MgSO$_4$ and concentrated to give additional product. In total 3.71 g of 2-bromo-5-(2-trimethylsilanylethoxymethyl)-5H-pyrrolo[2,3-b]pyrazine-7-carboxylic acid was obtained as a yellow solid. $^1$H NMR (CDCl$_3$, 400 MHz): δ (ppm) 8.52 (s, 1H), 8.42 (s, 1H), 5.73 (s, 2H), 3.56-3.65 (m, 2H), 0.90-1.02 (m, 2H), 0.00 (s, 9H).

Procedure 3

2-Bromo-N-tert-butyl-5-((2-(trimethylsilyl)ethoxy)methyl)-5H-pyrrolo[2,3-b]pyrazine-7-carboxamide

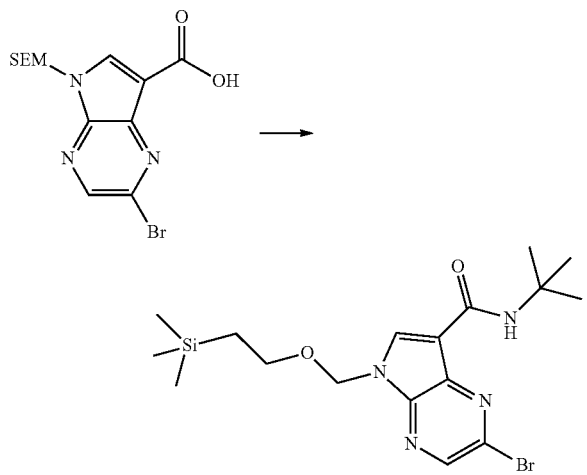

In a 100 ml round-bottomed flask, 2-bromo-5-(2-trimethylsilanyl-ethoxymethyl)-5H-pyrrolo[2,3-b]pyrazine-7-carboxylic acid (1.00 g, 2.69 mmol) was dissolved in DMF (6 ml). tert-Butylamine (1.7 ml, 16.2 mmol) was added followed by HATU (1.12 g, 2.95 mmol). The yellow suspension was stirred at room temperature for 72 h then quenched with water and extracted with a mixture of diethyl ether and EtOAc. The organic layers were washed twice with water and once with brine then combined, dried over sodium sulfate, filtered and concentrated. The residue was triturated with petroleum ether to afford 989 mg (86%) of 2-bromo-N-tert-butyl-5-((2-(trimethylsilyl)ethoxy)methyl)-5H-pyrrolo[2,3-b]pyrazine-7-carboxamide as an off-white powder. $^1$H NMR (CDCl$_3$, 300 MHz): δ (ppm) 8.40 (s, 1H), 8.31 (s, 1H), 7.86 (s, 1H), 5.65 (s, 2H), 3.46-3.58 (m, 2H), 1.54 (s, 9H), 0.84-0.98 (m, 2H), −0.04 (s, 9H).

Procedure 4

2-Bromo-N-(1-hydroxy-2-methylpropan-2-yl)-5-((2-(trimethylsilyl)ethoxy)methyl)-5H-pyrrolo[2,3-b]pyrazine-7-carboxamide

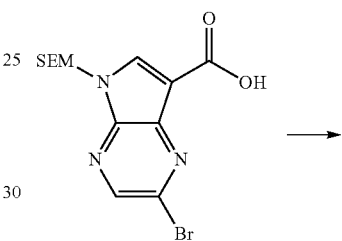

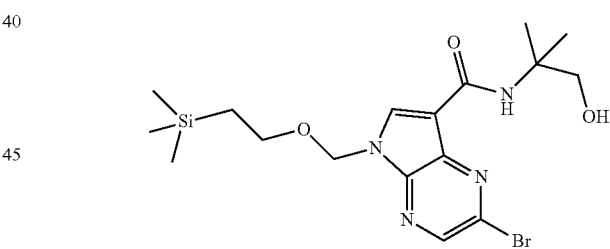

To a mixture of 2-bromo-5-((2-(trimethylsilyl)ethoxy)methyl)-5H-pyrrolo[2,3-b]pyrazine-7-carboxylic acid (2 g, 5.37 mmol), 2-amino-2-methylpropan-1-ol (575 mg, 6.45 mmol) and HATU (2.25 g, 5.91 mmol) was added DIPEA (2.08 g, 2.81 mL, 16.1 mmol) and DMF (18 mL). The mixture was stirred at room temperature for 16 h then was diluted with EtOAc and 10% citric acid. The phases were separated and the organic phase was then washed successively with 10% citric acid, NaHCO$_3$ and brine. The organic phase was dried (MgSO$_4$), filtered and purified by chromatography (silica, 20-60% ethyl acetate in hexanes) to give 2-bromo-N-(1-hydroxy-2-methylpropan-2-yl)-5-((2-(trimethylsilyl)ethoxy)methyl)-5H-pyrrolo[2,3-b]pyrazine-7-carboxamide (1.95 g, 4.4 mmol, 82%) as a white solid. $^1$H NMR (400 MHz, CHLOROFORM-d) δ ppm: 8.47 (s, 1H), 8.34 (s, 1H), 8.13 (s, 1H), 5.69 (s, 2H), 3.78 (s, 2H), 3.57 (t, J=8.4 Hz, 3H), 1.52 (s, 60.96 (t, J=8.4 Hz, 3H), 0.00 (s, 9H).

Example 1

N-tert-Butyl-2-(5-methylpyridin-2-ylamino)-5H-pyrrolo[2,3-b]pyrazine-7-carboxamide

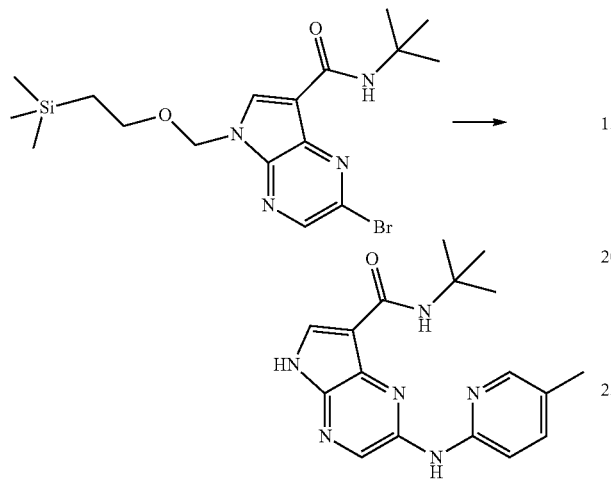

Step 1

To a mixture of 5-methylpyridin-2-amine (38.0 mg, 351 μmol), 2-bromo-N-tert-butyl-5-((2-(trimethylsilyl)ethoxy)methyl)-5H-pyrrolo[2,3-b]pyrazine-7-carboxamide (100 mg, 234 μmol) (R)-(+)-2,2'-bis(diphenylphosphino)-1,1'-binaphthyl (7.28 mg, 11.7 μmol), palladium(II) acetate (13.1 mg, 58.5 μmol) and sodium tert-butoxide (56.2 mg, 585 μmol) was added DMF (1 mL) and toluene (500 μL) and the mixture heated in a microwave at 140° C. for 20 min. The dark mixture generated was poured into water and extracted with ethyl acetate. The organic layers were combined, washed with brine, dried (magnesium sulfate), filtered and purified by chromatography (silica, 30-70% ethyl acetate in hexanes) to give N-tert-butyl-2-(5-methylpyridin-2-ylamino)-5-((2-(trimethylsilyl)ethoxy)methyl)-5H-pyrrolo[2,3-b]pyrazine-7-carboxamide (62 mg, 136 μmol, 58%) as an off white solid. MS (EI/CI) m/z: 455.3 [M+H].

Step 2

To a solution of N-tert-butyl-2-(5-methylpyridin-2-ylamino)-5-((2-(trimethylsilyl)ethoxy)methyl)-5H-pyrrolo[2,3-b]pyrazine-7-carboxamide (162 mg, 356 μmol) in dichloromethane (3 mL) was added trifluoroacetic acid (813 mg, 549 μL, 7.13 mmol) and the mixture stirred at room temperature for 16 h. The mixture was then concentrated in vacuo and the residue obtained was dissolved in dichloromethane (3 mL), methanol (1 mL) and ammonium hydroxide (0.6 mL) and the mixture stirred at room temperature for 30 min. The yellow precipitate formed was collected by filtration and dried. The mother liquor was purified by chromatography (silica, 5-25% of a 1:4 methanol:dichloromethane solution in dichloromethane) and combined with the solid to give N-tert-butyl-2-(5-methylpyridin-2-ylamino)-5H-pyrrolo[2,3-b]pyrazine-7-carboxamide (77 mg, 237 μmol, 67%) as an off-white solid. $^1$H NMR (400 MHz, DMSO-d) δ ppm: 12.37 (s, 1H), 9.88 (s, 1H), 8.38 (s, 1H), 8.13 (d, J=2.5 Hz, 1H), 8.04 (d, J=3.2 Hz, 1H), 7.88 (d, J=8.5 Hz, 1H), 7.74 (s, 1H), 7.51 (dd, J=8.2, 2.3 Hz, 1H), 2.25 (s, 3H), 1.47 (s, 9H); MS (EI/CI) m/z: 325.1 [M+H].

Example 2

N-(1-Hydroxy-2-methylpropan-2-yl)-2-(5-methylpyridin-2-ylamino)-5H-pyrrolo[2,3-b]pyrazine-7-carboxamide

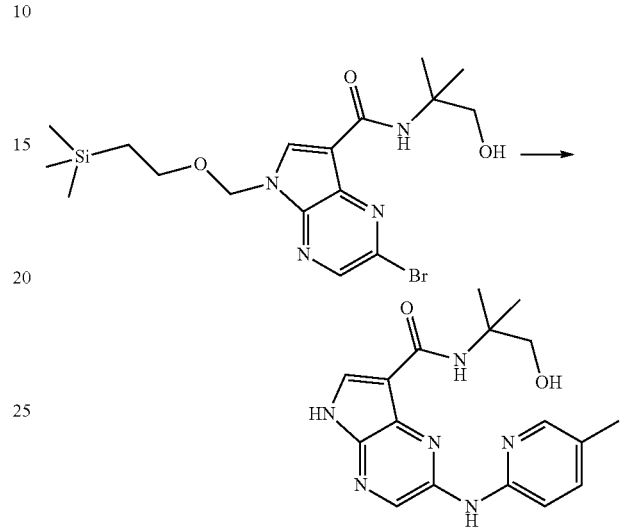

Step 1

To a mixture of 5-methylpyridin-2-amine (72.1 mg, 666 μmol), 2-bromo-N-(1-hydroxy-2-methylpropan-2-yl)-5-((2-(trimethylsilyl)ethoxy)methyl)-5H-pyrrolo[2,3-b]pyrazine-7-carboxamide (197 mg, 444 μmol), (R)-(+)-2,2'-bis(diphenylphosphino)-1,1'-binaphthyl (13.8 mg, 22.2 μmol), palladium(II) acetate (24.9 mg, 111 μmol) and sodium tert-butoxide (107 mg, 1.11 mmol) was added DMF (2 mL) and toluene (1 mL) then heated in a microwave at 140° C. for 20 min. The dark mixture generated was poured into water and extracted with ethyl acetate (3x). The organic layers were combined, washed with brine (2x), dried over magnesium sulfate and purified by chromatography (silica, 65-100% ethyl acetate in hexanes) to give N-(1-hydroxy-2-methylpropan-2-yl)-2-(5-methylpyridin-2-ylamino)-5-((2-(trimethylsilyl)ethoxy)methyl)-5H-pyrrolo[2,3-b]pyrazine-7-carboxamide (66 mg, 140 μmol, 32%) as a light yellow solid. MS (EI/CI) m/z: 471.4.

Step 2

To a solution of N-(1-hydroxy-2-methylpropan-2-yl)-2-(5-methylpyridin-2-ylamino)-5-((2-(trimethylsilyl)ethoxy)methyl)-5H-pyrrolo[2,3-b]pyrazine-7-carboxamide (66 mg, 140 μmol) in dichloromethane (1.5 mL) was added trifluoroacetic acid (320 mg, 216 μL, 2.8 mmol) and the mixture stirred at room temperature for 16 h. The reaction mixture was concentrated in vacuo then the residue was dissolved in dichloromethane (2 mL), methanol (0.5 mL) and ammonium hydroxide (0.3 mL). After stirring at room temperature for 30 min, the mixture was concentrated in vacuo and triturated with ether and water. The yellow precipitate was collected by filtration and washed with water then ether to give N-(1-hydroxy-2-methylpropan-2-yl)-2-(5-methylpyridin-2-ylamino)-5H-pyrrolo[2,3-b]pyrazine-7-carboxamide (31 mg, 91.1 μmol, 65%) as a yellow solid. $^1$H NMR (400 MHz, DMSO-d) δ ppm: 12.38 (s, 1H), 9.86 (s, 1H), 8.39 (s, 1H), 8.12 (d, J=2.5 Hz, 1H), 8.04 (d, J=3.3 Hz, 1H), 7.95 (d, J=8.4

Hz, 1H), 7.74 (s, 1H), 7.54 (dd, J=8.6, 2.3 Hz, 1H), 5.06 (s, 1H), 3.58 (s, 2H), 2.25 (s, 3H), 1.39 (s, 6H); MS (EI/CI) m/z: 341.1 [M+H].

Example 3

N-tert-Butyl-2-(1-methyl-1H-pyrazol-3-ylamino)-5H-pyrrolo[2,3-b]pyrazine-7-carboxamide 1H), 7.81 (s, 1H), 7.35 (d, J=2.2 Hz, 1H), 6.32 (d, J=2.2 Hz, 1H), 3.67 (s, 3H), 1.35 (s, 9H); MS (EI/CI) m/z: 314.1 [M+H].

Example 4

N-Isopropyl-2-(5-methylpyridin-2-ylamino)-5H-pyrrolo[2,3-b]pyrazine-7-carboxamide

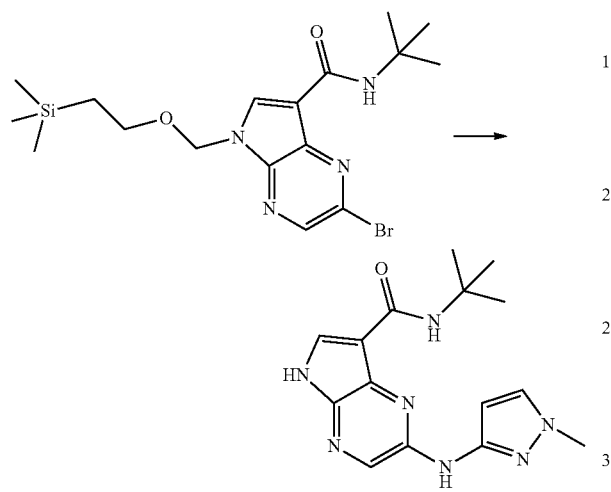

Step 1

A mixture of 2-bromo-N-tert-butyl-5-((2-(trimethylsilyl)ethoxy)methyl)-5H-pyrrolo[2,3-b]pyrazine-7-carboxamide (200 mg, 468 µmol), 1-methyl-1H-pyrazol-3-amine (68.2 mg, 702 µmol), BINAP (14.6 mg, 23.4 µmol), palladium (II) acetate (26.3 mg, 117 µmol) and sodium tert-butoxide (112 mg, 1.17 mmol) was added DMF (1.01 mL) and toluene (503 µL) was heated in a microwave at 140° C. for 20 min. The reaction mixture was cooled then diluted with water and extracted into ethyl acetate. The organic layers were combined and washed with brine and then dried over magnesium sulfate. Purification by chromatography (silica, 20-100% ethyl acetate in hexanes) gave N-tert-butyl-2-(1-methyl-1H-pyrazol-3-ylamino)-5-((2-(trimethylsilyl)ethoxy)methyl)-5H-pyrrolo[2,3-b]pyrazine-7-carboxamide (140 mg, 316 µmol, 67%) as a yellow solid. MS (EI/CI) m/z: 444.3.

Step 2

To a solution of N-tert-butyl-2-(1-methyl-1H-pyrazol-3-ylamino)-5-((2-(trimethylsilyl)ethoxy)methyl)-5H-pyrrolo[2,3-b]pyrazine-7-carboxamide (140 mg, 316 µmol) in dichloromethane (3.5 mL) was added trifluoroacetic acid (720 mg, 486 µL, 6.31 mmol) and the mixture stirred at room temperature for 16 h. The reaction mixture was concentrated in vacuo and the residue obtained dissolved in dichloromethane (3 mL), methanol (1.5 mL), and ammonium hydroxide (0.65 mL) and the mixture stirred at room temperature for 1 h. The mixture was concentrated in vacuo then triturated with ether and water. The solid was collected by filtration then dried in vacuo to give N-tert-butyl-2-(1-methyl-1H-pyrazol-3-ylamino)-5H-pyrrolo[2,3-b]pyrazine-7-carboxamide (44 mg, 140 µmol, 45%) as a brown solid. $^1$H NMR (400 MHz, methanol-d) δ ppm: 8.07 (s, 1H), 7.93 (s, Step 1

A mixture of 2-bromo-N-isopropyl-5-((2-(trimethylsilyl)ethoxy)methyl)-5H-pyrrolo[2,3-b]pyrazine-7-carboxamide (150 mg, 363 µmol), 5-methylpyridin-2-amine (58.9 mg, 544 µmol), BINAP (11.3 mg, 18.1 µmol), palladium (II) acetate (20.4 mg, 90.7 µmol) and sodium tert-butoxide (87.2 mg, 907 µmol) was added DMF (780 µL) and toluene (390 µL) was heated in a microwave at 140° C. for 20 min. The mixture was cooled then diluted with water and ethyl acetate. The mixture was extracted with ethyl acetate (3×) then the organic extracts were combined and washed with brine, dried over magnesium sulfate and purified by chromatography (silica, 30-70% ethyl acetate in hexanes) to give N-isopropyl-2-(5-methylpyridin-2-ylamino)-5-((2-(trimethylsilyl)ethoxy)methyl)-5H-pyrrolo[2,3-b]pyrazine-7-carboxamide (90 mg, 204 µmol, 56%) as an off-white solid. MS (EI/CI) m/z: 441.3 [M+H].

Step 2

To a solution of N-isopropyl-2-(5-methylpyridin-2-ylamino)-5-((2-(trimethylsilyl)ethoxy)methyl)-5H-pyrrolo[2,3-b]pyrazine-7-carboxamide (90 mg, 204 µmol) in dichloromethane (2.5 mL) was added trifluoroacetic acid (466 mg, 315 µL, 4.09 mmol) and stirred at room temperature for 16 h. The reaction mixture was concentrated in vacuo then the residue obtained was dissolved in dichloromethane (3 mL), methanol (1.5 mL) and ammonium hydroxide (0.45 mL). After 3 h at room temperature, the mixture was concentrated in vacuo then triturated with water and ether. The solid was collected by filtration to give N-isopropyl-2-(5-methylpyridin-2-ylamino)-5H-pyrrolo[2,3-b]pyrazine-7-carboxamide (23 mg, 74.1 µmol, 36%) as an off white solid. $^1$H NMR (400 MHz, DMSO-d) δ ppm: 12.40 (s, 1H), 9.92 (s, 1H), 8.43 (s, 1H), 8.14 (s, 1H), 8.09 (d, J=3.2, 1 H), 7.86 (s, 1H), 7.85 (d, J=15.1 Hz, 1H), 7.55 (dd, J=8.5, 2.3 Hz, 1H), 4.16 (m, 1H), 2.26 (s, 3H), 1.25 (d, J=6.5, 6 H); MS (EI/CI) m/z: 311.1 [M+H].

Example 5

N-tert-Butyl-2-(1-methyl-1H-pyrazol-4-ylamino)-5H-pyrrolo[2,3-b]pyrazine-7-carboxamide

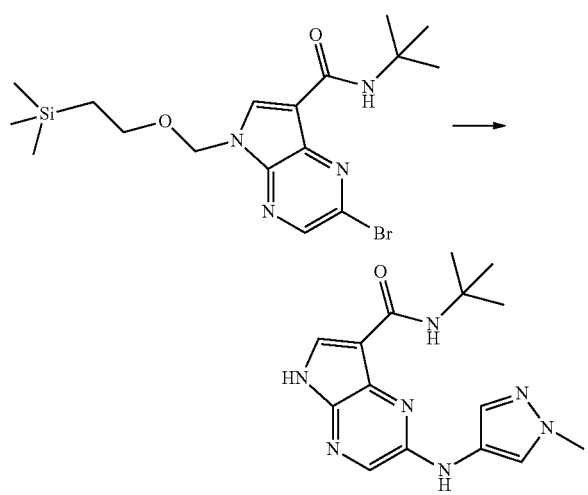

Step 1

To a mixture of 2-bromo-N-tert-butyl-5-((2-(trimethylsilyl)ethoxy)methyl)-5H-pyrrolo[2,3-b]pyrazine-7-carboxamide (150 mg, 351 mol), 1-methyl-1H-pyrazol-4-amine hydrochloride (70.3 mg, 526 mol), BINAP (10.9 mg, 17.5 mol), palladium (II) acetate (19.7 mg, 87.7 mol) and sodium tert-butoxide (84.3 mg, 877 mol) was added DMF (1 mL) and toluene (500 µL). After heating in a microwave at 140° C. for 20 min, the reaction mixture was cooled, diluted with water and extracted with ethyl acetate (3×). The combined organic extracts were washed with brine, then dried over magnesium sulfate, and purified by chromatography (silica, 30-70% ethyl acetate in hexanes) to give N-tert-butyl-2-(1-methyl-1H-pyrazol-4-ylamino)-5-((2-(trimethylsilyl)ethoxy)methyl)-5H-pyrrolo[2,3-b]pyrazine-7-carboxamide (89 mg, 201 mol, 57%) as a yellow solid. MS (EI/CI) m/z: 314.1 [M+H].

Step 2

To a solution of N-tert-butyl-2-(1-methyl-1H-pyrazol-4-ylamino)-5-((2-(trimethylsilyl)ethoxy)methyl)-5H-pyrrolo[2,3-b]pyrazine-7-carboxamide (89 mg, 201 mol) in dichloromethane (3 mL) was added trifluoroacetic acid (458 mg, 309 µL, 4.01 mmol) and the reaction mixture stirred at room temperature for 16 h. The mixture was concentrated in vacuo then dissolved in dichloromethane (3 mL), methanol (1.5 mL) and ammonium hydroxide (0.45 mL) and the mixture stirred at room temperature for 1 h. After concentration in vacuo, the mixture was triturated with water and filtered to collect the solid. The solid was washed with ether and dried to give N-tert-butyl-2-(1-methyl-1H-pyrazol-4-ylamino)-5H-pyrrolo[2,3-b]pyrazine-7-carboxamide (58 mg, 185 mol, 92%) as a brown solid. $^1$H NMR (400 MHz, DMSO-d) δ ppm: 12.18 (s, 1H), 9.11 (s, 1H), 7.90 (d, J=3.2, 1 H), 7.86 (s, 1H), 7.85 (s, 1H), 7.72 (s, 1H), 7.55 (s, 1H), 3.80 (s, 3H), 1.43 (s, 9H); MS (EI/CI) m/z: 314.1 [M+H].

Example 6

N-tert-Butyl-2-(6-methylpyridin-3-ylamino)-5H-pyrrolo[2,3-b]pyrazine-7-carboxamide

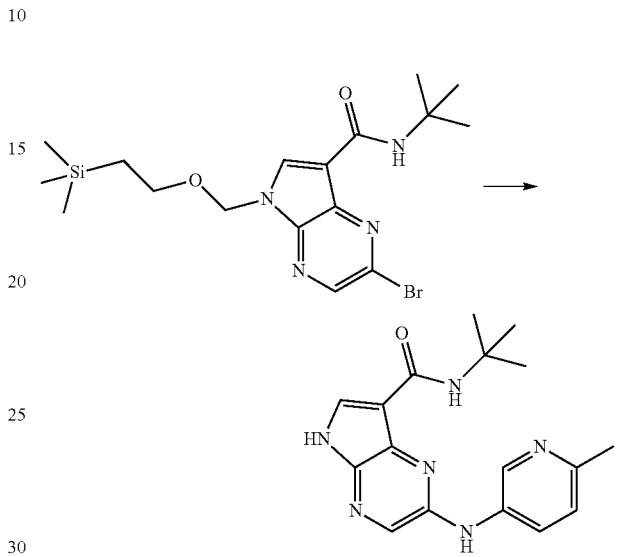

Step 1

A mixture of 2-bromo-N-tert-butyl-5-((2-(trimethylsilyl)ethoxy)methyl)-5H-pyrrolo[2,3-b]pyrazine-7-carboxamide (150 mg, 351 mol), 6-methylpyridin-3-amine (56.9 mg, 526 mol), BINAP (10.9 mg, 17.5 mol), palladium (II) acetate (19.7 mg, 87.7 mol) and sodium tert-butoxide (84.3 mg, 877 mol) in DMF (1 mL) and toluene (500 µL) was heated in a microwave at 140° C. for 20 min. The reaction mixture was cooled then diluted with water and extracted into ethyl acetate (3×). The combined organic extracts were washed with brine then dried over magnesium sulfate. Purification by chromatography (silica, 30-70% ethyl acetate in hexanes) gave N-tert-butyl-2-(6-methylpyridin-3-ylamino)-5-((2-(trimethylsilyl)ethoxy)methyl)-5H-pyrrolo[2,3-b]pyrazine-7-carboxamide (57 mg, 125 mol, 36%) as a brown solid. MS (EI/CI) m/z: 455.2 [M+H].

Step 2

To a solution of N-tert-butyl-2-(6-methylpyridin-3-ylamino)-5-((2-(trimethylsilyl)ethoxy)methyl)-5H-pyrrolo[2,3-b]pyrazine-7-carboxamide (55 mg, 121 mol) in dichloromethane (1.9 mL) was added trifluoroacetic acid (276 mg, 186 µL, 2.42 mmol) and the mixture stirred at room temperature for 16 h. The reaction mixture was concentrated in vacuo and the residue obtained then dissolved in dichloromethane (2 mL), methanol (1 mL) and ammonium hydroxide (0.25 mL) and the mixture stirred at room temperature for 1 h. The mixture was concentrated and triturated with water, then filtered to obtain a solid which was washed with ether and dried to give N-tert-butyl-2-(6-methylpyridin-3-ylamino)-5H-pyrrolo[2,3-b]pyrazine-7-carboxamide (33 mg, 102 mol, 84%) as a brown solid. $^1$H NMR (400 MHz, DMSO-d) δ ppm: 12.23 (s, 1H), 9.41 (s, 1H), 8.60 (d, J=2.3, 1 H), 7.91 (m, 3H), 7.59 (s, 1H), 7.06 (d, J=8.5, 1 H), 2.31 (s, 3H), 1.32 (s, 9H); MS (EI/CI) m/z: 325.1 [M+H].

Example 7

N-tert-Butyl-2-(2-methylpyrimidin-5-ylamino)-5H-pyrrolo[2,3-b]pyrazine-7-carboxamide

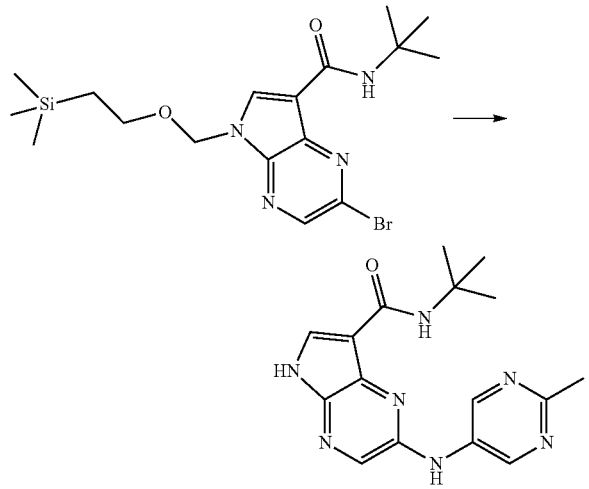

Step 1

A mixture of 2-bromo-N-tert-butyl-5-((2-(trimethylsilyl)ethoxy)methyl)-5H-pyrrolo[2,3-b]pyrazine-7-carboxamide (150 mg, 351 μmol), 2-methylpyrimidin-5-amine (57.4 mg, 526 μmol), BINAP (10.9 mg, 17.5 μmol), palladium (II) acetate (19.7 mg, 87.7 μmol) and sodium tert-butoxide (84.3 mg, 877 μmol) in DMF (1 mL) and toluene (500 μL) was heated in a microwave at 140° C. for 20 min. The reaction mixture was diluted with water then extracted into ethyl acetate (3×). The combined organic extracts were washed with brine then dried over magnesium sulfate. Purification by chromatography (silica, 40-80% ethyl acetate in hexanes) gave N-tert-butyl-2-(2-methylpyrimidin-5-ylamino)-5-((2-(trimethylsilyl)ethoxy)methyl)-5H-pyrrolo[2,3-b]pyrazine-7-carboxamide (78 mg, 171 μmol, 49%) as a brown solid. MS (EI/CI) m/z: 456.2 [M+H].

Step 2

To a solution of N-tert-butyl-2-(2-methylpyrimidin-5-ylamino)-5-((2-(trimethylsilyl)ethoxy)methyl)-5H-pyrrolo[2,3-b]pyrazine-7-carboxamide (78 mg, 171 μmol) in dichloromethane (2.5 mL) was added trifluoroacetic acid (390 mg, 264 μL, 3.42 mmol) and the mixture stirred at room temperature for 16 h. The reaction mixture was concentrated in vacuo and the residue obtained diluted with dichloromethane (2.5 mL), methanol (1.2 mL) and ammonium hydroxide (0.35 mL) and the mixture stirred at room temperature for 1 h. The reaction mixture was concentrated in vacuo then triturated with water. The solid was collected by filtration and washed with water and ether to give N-tert-butyl-2-(2-methylpyrimidin-5-ylamino)-5H-pyrrolo[2,3-b]pyrazine-7-carboxamide (43 mg, 132 μmol, 77%) as a brown solid. $^1$H NMR (400 MHz, DMSO-d) δ ppm: 12.31 (s, 1H), 9.57 (s, 1H), 8.90 (s, 2H), 7.96 (d, J=3.3, 1H), 7.92 (s, 1H), 7.53 (s, 1H), 2.46 (s, 3H), 1.32 (s, 9H); MS (EI/CI) m/z: 326.1 [M+H].

Example 8

N-tert-Butyl-2-(5-methylpyrazin-2-ylamino)-5H-pyrrolo[2,3-b]pyrazine-7-carboxamide

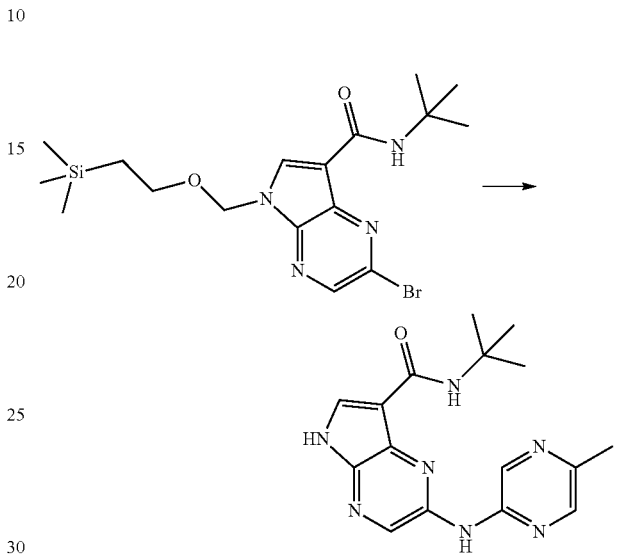

Step 1

A mixture of 2-bromo-N-tert-butyl-5-((2-(trimethylsilyl)ethoxy)methyl)-5H-pyrrolo[2,3-b]pyrazine-7-carboxamide (150 mg, 351 mol), 5-methylpyrazin-2-amine (57.4 mg, 526 mol), BINAP (10.9 mg, 17.5 mol), palladium (II) acetate (19.7 mg, 87.7 mol) and sodium tert-butoxide (84.3 mg, 877 mol) in added DMF (1 mL) and toluene (500 μL) was heated in a microwave at 140° C. for 20 min. The reaction mixture was diluted with water then extracted into ethyl acetate (3×). The combined organic extracts were washed with brine then dried over magnesium sulfate. Purification by chromatography (silica, 30-70% ethyl acetate in hexanes) gave N-tert-butyl-2-(5-methylpyrazin-2-ylamino)-5-((2-(trimethylsilyl)ethoxy)methyl)-5H-pyrrolo[2,3-b]pyrazine-7-carboxamide (72 mg, 158 mol, 45%) as an off white solid. MS (EI/CI) m/z: 456.2 [M+H].

Step 2

To a solution of N-tert-butyl-2-(5-methylpyrazin-2-ylamino)-5-((2-(trimethylsilyl)ethoxy)methyl)-5H-pyrrolo[2,3-b]pyrazine-7-carboxamide (72 mg, 158 mol) in dichloromethane (2.5 mL) was added trifluoroacetic acid (360 mg, 243 μL, 3.16 mmol) and stirred at room temperature for 16 h. The reaction mixture was concentrated in vacuo and the residue obtained diluted with dichloromethane (2.5 mL), methanol (1.2 mL) and ammonium hydroxide (0.35 mL) and the mixture stirred at room temperature for 1 h. The mixture was concentrated and triturated with water. The solid was collected by filtration and washed with water and ether to give N-tert-butyl-2-(5-methylpyrazin-2-ylamino)-5H-pyrrolo[2,3-b]pyrazine-7-carboxamide (26 mg, 79.9 mol, 51%) as a light green solid. $^1$H NMR (400 MHz, DMSO-d) δ ppm: 12.45 (s, 1H), 10.12 (s, 1H), 9.17 (d, J=1.5, 1 H), 8.40 (s, 1H), 8.21 (s, 1H), 8.10 (d, J=3.2, 1 H), 7.73 (s, 1H), 2.42 (s, 3H), 1.46 (s, 9H); MS (EI/CI) m/z: 326.1 [M+H].

Example 9

N-tert-Butyl-2-(3-methyl-1H-pyrazol-5-ylamino)-5H-pyrrolo[2,3-b]pyrazine-7-carboxamide

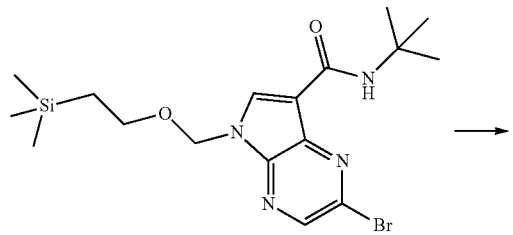

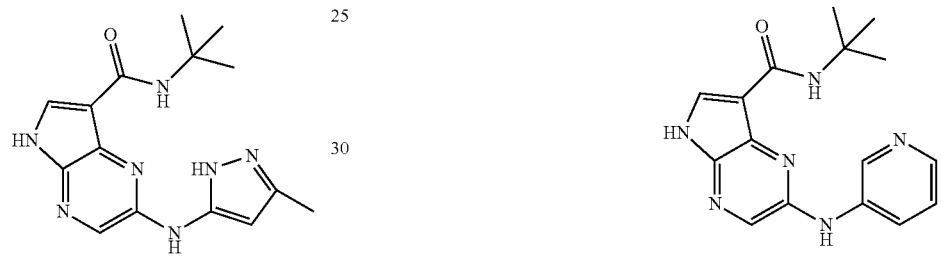

A mixture of 2-bromo-N-tert-butyl-5-((2-(trimethylsilyl)ethoxy)methyl)-5H-pyrrolo[2,3-b]pyrazine-7-carboxamide (150 mg, 351 μmol), 3-methyl-1H-pyrazol-5-amine (51.1 mg, 526 μmol), BINAP (10.9 mg, 17.5 μmol), palladium (II) acetate (19.7 mg, 87.7 μmol) and sodium tert-butoxide (84.3 mg, 877 μmol) in DMF (1 mL) and toluene (500 μL) was heated in a microwave at 140° C. for 20 min. The reaction mixture was diluted with water then extracted into ethyl acetate (3×). The combined organic extracts were washed with brine then dried over magnesium sulfate. Purification by chromatography (silica, 50-100% ethyl acetate in hexanes) gave N-tert-butyl-2-(3-methyl-1H-pyrazol-5-ylamino)-5-((2-(trimethylsilyl)ethoxy)methyl)-5H-pyrrolo[2,3-b]pyrazine-7-carboxamide (27 mg, 60.9 μmol, 17.3%) as a brown solid. MS (EI/CI) m/z: 443.3 [M+H].

Step 2

To a solution of N-tert-butyl-2-(3-methyl-1H-pyrazol-5-ylamino)-5-((2-(trimethylsilyl)ethoxy)methyl)-5H-pyrrolo[2,3-b]pyrazine-7-carboxamide (25 mg, 56.4 μmol) in dichloromethane (1 mL) was added trifluoroacetic acid (129 mg, 86.8 μL, 1.13 mmol) and the mixture stirred at room temperature for 16 h. The reaction mixture was concentrated in vacuo and the residue obtained diluted with dichloromethane (1 mL), methanol (0.5 mL) and ammonium hydroxide (0.15 mL) and stirred at room temperature for 1 h. Purification by chromatography (silica, 20-50% [10% methanol/dichloromethane/0.5% ammonium hydroxide]/dichloromethane) gave N-tert-butyl-2-(3-methyl-1H-pyrazol-5-ylamino)-5H-pyrrolo[2,3-b]pyrazine-7-carboxamide (10 mg, 31.9 μmol, 57%) as a light brown solid. $^1$H NMR (400 MHz, DMSO-d) δ ppm: 12.19 (s, 1H), 10.12 (s, 1H), 9.53 (s, 1H), 8.07 (s, 1H), 7.93 (d, J=3.0, 1 H), 7.81 (s, 1H), 6.33 (s, 1H), 2.19 (s, 3H), 1.45 (s, 9H); MS (EI/CI) m/z: 314.1 [M+H].

Example 10

N-tert-Butyl-2-(pyridin-3-ylamino)-5H-pyrrolo[2,3-b]pyrazine-7-carboxamide

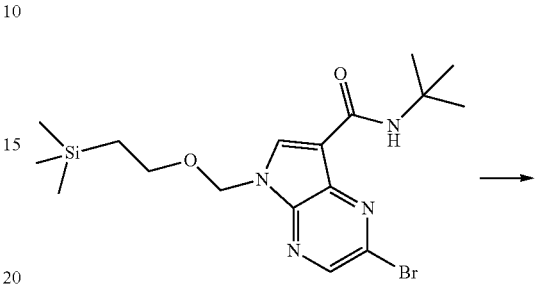

Step 1

A mixture of 2-bromo-N-tert-butyl-5-((2-(trimethylsilyl)ethoxy)methyl)-5H-pyrrolo[2,3-b]pyrazine-7-carboxamide (150 mg, 351 mol), pyridin-3-amine (49.5 mg, 526 mol), BINAP (10.9 mg, 17.5 mol), palladium (II) acetate (19.7 mg, 87.7 mol) and sodium tert-butoxide (84.3 mg, 877 mol) in DMF (1 mL) and toluene (500 μL) was heated in a microwave at 140° C. for 20 min. The reaction mixture was diluted with water then extracted into ethyl acetate (3×). The combined organic extracts were washed with brine then dried over magnesium sulfate. Purification by chromatography (silica, 30-70% ethyl acetate in hexanes) gave N-tert-butyl-2-(pyridin-3-ylamino)-5-((2-(trimethylsilyl)ethoxy)methyl)-5H-pyrrolo[2,3-b]pyrazine-7-carboxamide (44 mg, 99.9 mol, 28.5%) as a yellow solid. MS (EI/CI) m/z: 311.1 [M+H].

Step 2

To a solution of N-tert-butyl-2-(pyridin-3-ylamino)-5-((2-(trimethylsilyl)ethoxy)methyl)-5H-pyrrolo[2,3-b]pyrazine-7-carboxamide (44 mg, 99.9 mol) in dichloromethane (1.6 mL) was added trifluoroacetic acid (228 mg, 154 μL, 2.00 mmol) and the reaction mixture stirred at room temperature for 16 h. The reaction mixture was concentrated in vacuo and the residue obtained diluted with dichloromethane (1.6 mL), methanol (0.8 mL) and ammonium hydroxide (0.2 mL) and stirred at room temperature for 1 h. The mixture was concentrated and triturated with water. The solid was collected by filtration and washed with water and ether to give N-tert-butyl-2-(pyridin-3-ylamino)-5H-pyrrolo[2,3-b]pyrazine-7-carboxamide (24 mg, 77.3 mol, 77%) as a brown solid. $^1$H NMR (400 MHz, DMSO-d) δ ppm: 12.26 (s, 1H), 9.54 (s, 1H), 8.77 (d, J=2.5, 1 H), 8.04 (d, J=4.6, 1 H), 7.98 (d, J=8.5, 1 H), 7.92 (d, J=3.3, 1 H), 7.91 (s, 1H), 7.57 (s, 1H), 7.19 (m, 1H), 1.31 (s, 9H); MS (EI/CI) m/z: 311.1 [M+H].

Example 11

N-tert-Butyl-2-(2-fluoro-4-methylphenylamino)-5H-pyrrolo[2,3-b]pyrazine-7-carboxamide

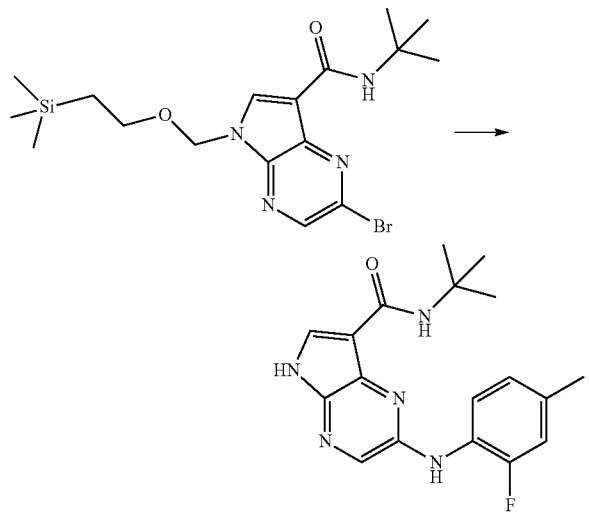

Step 1

A mixture of 2-bromo-N-tert-butyl-5-((2-(trimethylsilyl) ethoxy)methyl)-5H-pyrrolo[2,3-b]pyrazine-7-carboxamide (150 mg, 351 μmol), 2-fluoro-4-methylaniline (65.9 mg, 526 μmol), BINAP (10.9 mg, 17.5 μmol), palladium (II) acetate (19.7 mg, 87.7 μmol) and sodium tert-butoxide (84.3 mg, 877 μmol) in DMF (1 mL) and toluene (500 μL) was heated in a microwave at 140° C. for 20 min. The reaction mixture was diluted with water then extracted into ethyl acetate (3×). The combined organic extracts were washed with brine then dried over magnesium sulfate. Purification by chromatography (silica, 20-50% ethyl acetate/hexanes) gave N-tert-butyl-2-(2-fluoro-4-methylphenylamino)-5-((2-(trimethylsilyl) ethoxy)methyl)-5H-pyrrolo[2,3-b]pyrazine-7-carboxamide (87 mg, 184 μmol, 53%) as an off-white solid. MS (EI/CI) m/z: 470.1 [M−H].

Step 2

To a solution of N-tert-butyl-2-(2-fluoro-4-methylphenylamino)-5-((2-(trimethylsilyl)ethoxy)methyl)-5H-pyrrolo[2,3-b]pyrazine-7-carboxamide (87 mg, 184 μmol) in dichloromethane (3 mL) was added trifluoroacetic acid (421 mg, 284 μL, 3.69 mmol) and the mixture stirred at room temperature for 16 h. The reaction mixture was concentrated in vacuo and the residue obtained diluted with dichloromethane (3 mL), methanol (1.5 mL) and ammonium hydroxide (0.4 mL) and stirred at room temperature for 1 h. The mixture was concentrated and triturated with water. The solid was collected by filtration and washed with water and ether to give N-tert-butyl-2-(2-fluoro-4-methylphenylamino)-5H-pyrrolo[2,3-b]pyrazine-7-carboxamide (58 mg, 170 μmol, 92%) as an off-white solid. $^1$H NMR (400 MHz, DMSO-d) δ ppm: 12.27 (s, 1H), 8.97 (s, 1H), 8.10 (s, 1H), 7.96 (d, J=2.3, 1 H), 7.81 (t, J=8.6, 1 H), 7.70 (s, 1H), 7.10 (d, J=12.4, 1 H), 6.95 (d, J=8.0, 1 H), 2.29 (s, 3H), 1.32 (s, 9H); MS (EI/CI) m/z: 342.1 [M+H].

Example 12

N-tert-butyl-2-(p-tolylamino)-5H-pyrrolo[2,3-b]pyrazine-7-carboxamide

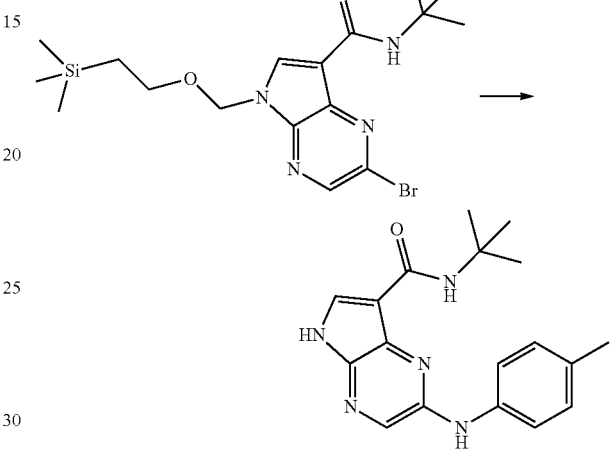

Step 1

A mixture of 2-bromo-N-tert-butyl-5-((2-(trimethylsilyl) ethoxy)methyl)-5H-pyrrolo[2,3-b]pyrazine-7-carboxamide (150 mg, 351 μmol), p-toluidine (56.4 mg, 526 μmol), BINAP (10.9 mg, 17.5 μmol), palladium (II) acetate (19.7 mg, 87.7 μmol) and sodium tert-butoxide (84.3 mg, 877 μmol) in DMF (1 mL) and toluene (500 μL) was heated in a microwave at 140° C. for 20 min. The reaction mixture was diluted with water then extracted into ethyl acetate (3×). The combined organic extracts were washed with brine then dried over magnesium sulfate. Purification by chromatography (silica, 20-45% ethyl acetate in hexanes) gave N-tert-butyl-2-(p-tolylamino)-5-((2-(trimethylsilyl)ethoxy)methyl)-5H-pyrrolo[2,3-b]pyrazine-7-carboxamide (80 mg, 116 μmol, 33%) as a brown gum. MS (EI/CI) m/z: 454.4 [M+H].

Step 2

To a solution of N-tert-butyl-2-(p-tolylamino)-5-((2-(trimethylsilyl)ethoxy)methyl)-5H-pyrrolo[2,3-b]pyrazine-7-carboxamide (80 mg, 176 μmol) in dichloromethane (3 mL) was added trifluoroacetic acid (402 mg, 272 μL, 3.53 mmol) and the mixture stirred at room temperature for 16 h. The reaction mixture was concentrated in vacuo and the residue obtained diluted with dichloromethane (3 mL), methanol (1.5 mL) and ammonium hydroxide (0.4 mL) and stirred at room temperature for 1 h. The mixture was concentrated and triturated with water. The solid was collected by filtration and washed with water and ether. Purification by chromatography (silica, 20-40% of a 10:89.5:0.5 methanol:dichloromethane:ammonium hydroxide solution in dichloromethane) gave N-tert-butyl-2-(p-tolylamino)-5H-pyrrolo[2,3-b]pyrazine-7-carboxamide (17 mg, 52.6 μmol, 30%) as a light yellow solid. $^1$H NMR (400 MHz, DMSO-d) δ ppm: 12.26 (s, 1H), 9.34 (s, 1H), 7.97 (s, 1H), 7.96 (d, J=3.3, 1 H), 7.76 (s, 1H), 7.57 (t, J=8.5, 2 H), 7.09 (d, J=8.1, 2 H), 2.26 (s, 3H), 1.44 (s, 9H); MS (EI/CI) m/z: 324.1 [M+H].

Example 13

N-tert-Butyl-2-(3-(methylsulfonyl)phenylamino)-5H-pyrrolo[2,3-b]pyrazine-7-carboxamide

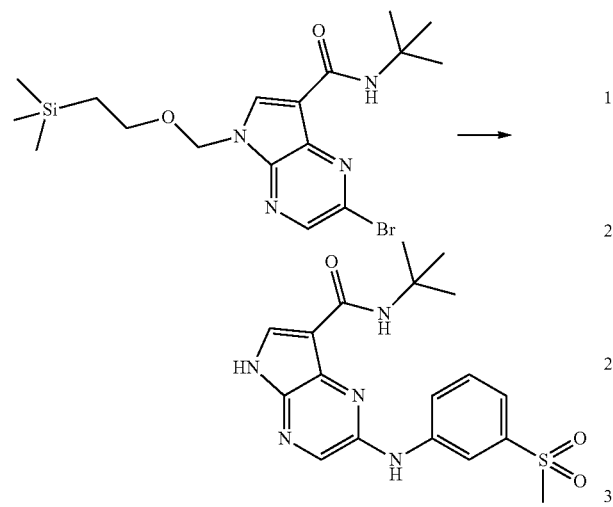

Step 1

A mixture of 2-bromo-N-tert-butyl-5-((2-(trimethylsilyl)ethoxy)methyl)-5H-pyrrolo[2,3-b]pyrazine-7-carboxamide (150 mg, 351 mol), 3-(methylsulfonyl)aniline hydrochloride (109 mg, 526 mol), BINAP (10.9 mg, 17.5 mol), palladium (II) acetate (19.7 mg, 87.7 mol) and sodium tert-butoxide (101 mg, 1.05 mmol, Eq: 3) in DMF (1 mL) and toluene (500 μL) was heated in a microwave at 140° C. for 20 min. The reaction mixture was diluted with water then extracted into ethyl acetate (3×). The combined organic extracts were washed with brine then dried over magnesium sulfate. Purification by chromatography (silica, 20-50% ethyl acetate in hexanes) gave N-tert-butyl-2-(3-(methylsulfonyl)phenylamino)-5-((2-(trimethylsilyl)ethoxy)methyl)-5H-pyrrolo[2,3-b]pyrazine-7-carboxamide (61 mg, 118 mol, 34%) as a brown gum. (EI/CI) m/z: 518.3 [M+H].

Step 2

To a solution of N-tert-butyl-2-(3-(methylsulfonyl)phenylamino)-5-((2-(trimethylsilyl)ethoxy)methyl)-5H-pyrrolo[2,3-b]pyrazine-7-carboxamide (61 mg, 118 mol) in dichloromethane (1.8 mL) was added trifluoroacetic acid (269 mg, 182 μL, 2.36 mmol) and the mixture stirred at room temperature for 16 h. The reaction mixture was concentrated in vacuo and the residue obtained diluted with dichloromethane (1.8 mL), methanol (0.9 mL) and ammonium hydroxide (0.25 mL) and stirred at room temperature for 1 h. The mixture was concentrated and triturated with water. The solid was collected by filtration and washed with water and ether. Purification by chromatography (silica, GRADIENT UNKNOWN dichloromethane/methanol/0.5% ammonium hydroxide) gave N-tert-butyl-2-(3-(methylsulfonyl)phenylamino)-5H-pyrrolo[2,3-b]pyrazine-7-carboxamide (26 mg, 67.1 mol, 57%) as a yellow solid. ¹H NMR (400 MHz, DMSO-d) δ ppm: 12.42 (s, 1H), 9.87 (s, 1H), 8.33 (d, J=8.2, 1 H), 8.05 (d, J=3.4, 1 H), 8.03 (s, 1H), 7.79 (t, J=2.0, 1 H), 7.68 (s, 1H), 7.54 (t, J=8.0, 1 H), 7.47 (d, J=7.7, 1 H), 3.21 (s, 3H), 1.42 (s, 9H); MS (EI/CI) m/z: 388.2 [M+H].

Example 14

N-tert-Butyl-2-(1-ethyl-1H-pyrazol-4-ylamino)-5H-pyrrolo[2,3-b]pyrazine-7-carboxamide

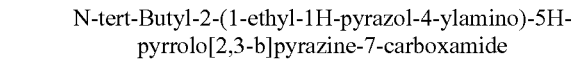

Step 1

A mixture of 2-bromo-N-tert-butyl-5-((2-(trimethylsilyl)ethoxy)methyl)-5H-pyrrolo[2,3-b]pyrazine-7-carboxamide (150 mg, 351 μmol), 1-ethyl-1H-pyrazol-4-amine hydrochloride (51.8 mg, 526 μmol), BINAP (10.9 mg, 17.5 μmol), palladium (II) acetate (19.7 mg, 87.7 μmol) and sodium tert-butoxide (101 mg, 1.05 mmol, Eq: 3) in DMF (1 mL) and toluene (500 μL) was heated in a microwave at 140° C. for 20 min. The reaction mixture was diluted with water then extracted into ethyl acetate (3×). The combined organic extracts were washed with brine then dried over magnesium sulfate. Purification by chromatography (silica, 40-80% ethyl acetate in hexanes) gave N-tert-butyl-2-(1-ethyl-1H-pyrazol-4-ylamino)-5-((2-(trimethylsilyl)ethoxy)methyl)-5H-pyrrolo[2,3-b]pyrazine-7-carboxamide (82 mg, 179 μmol, 51%) as a yellow gum. (EI/CI) m/z: 458.4 [M+H].

Step 2

To a solution of N-tert-butyl-2-(1-ethyl-1H-pyrazol-4-ylamino)-5-((2-(trimethylsilyl)ethoxy)methyl)-5H-pyrrolo[2,3-b]pyrazine-7-carboxamide (82 mg, 179 μmol) in dichloromethane (2.7 mL) was added trifluoroacetic acid (409 mg, 276 μL, 3.58 mmol) and the mixture stirred at room temperature for 16 h. The reaction mixture was concentrated in vacuo and the residue obtained diluted with dichloromethane (3 mL), methanol (1.5 mL) and ammonium hydroxide (0.4 mL) and stirred at room temperature for 1 h. The reaction mixture was concentrated then purified by chromatography (silica, 15-65% dichloromethane/[10% dichloromethane/methanol/0.5% ammonium hydroxide]) to give N-tert-butyl-2-(1-ethyl-1H-pyrazol-4-ylamino)-5H-pyrrolo[2,3-b]pyrazine-7-carboxamide (33 mg, 101 μmol, 56%) as a yellow solid. ¹H NMR (400 MHz, DMSO-d) δ ppm: 12.16 (s, 1H), 9.06 (s, 1H), 7.90

(d, J=3.3, 1 H), 7.85 (s, 1H), 7.84 (s, 1H), 7.73 (s, 1H), 7.59 (s, 1H), 4.08 (q, J=7.3, 2 H), 1.42 (s, 9H), 1.36 (t, J=7.3, 3 H); MS (EI/CI) m/z: 328.1 [M+H].

Example 15

N-tert-Butyl-2-(2-(dimethylcarbamoyl)phenylamino)-5H-pyrrolo[2,3-b]pyrazine-7-carboxamide

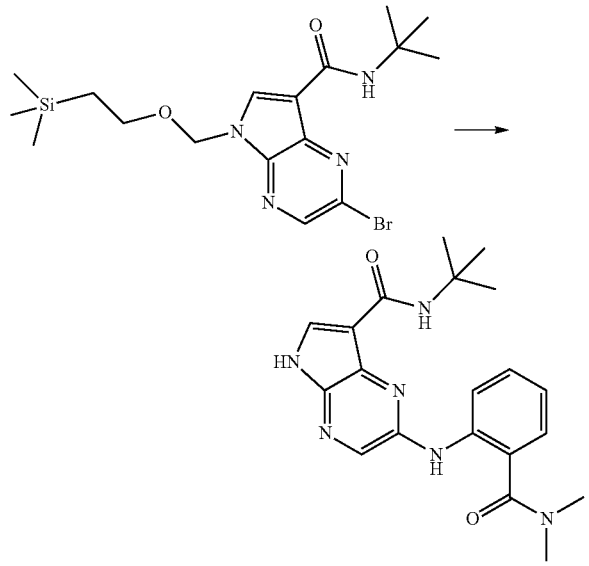

Step 1

To a solution of 2-bromo-N-tert-butyl-5-((2-(trimethylsilyl)ethoxy)methyl)-5H-pyrrolo[2,3-b]pyrazine-7-carboxamide (150 mg, 351 μmol) in dichloromethane (5.5 mL) was added trifluoroacetic acid (800 mg, 541 μL, 7.02 mmol) and the mixture stirred at room temperature for 16 h. The reaction mixture was concentrated in vacuo and the residue obtained diluted with dichloromethane (5 mL), methanol (2.5 mL) and ammonium hydroxide (0.7 mL) and stirred at room temperature for 1 h. The mixture was concentrated and triturated with water. The solid was collected by filtration and washed with water and ether to give 2-bromo-N-tert-butyl-5H-pyrrolo[2,3-b]pyrazine-7-carboxamide (80 mg, 269 μmol, 77%) as an off white solid.

Step 2

A mixture of 2-bromo-N-tert-butyl-5H-pyrrolo[2,3-b]pyrazine-7-carboxamide (80 mg, 269 μmol), 2-amino-N,N-dimethylbenzamide hydrochloride (81.0 mg, 404 μmol), BINAP (8.38 mg, 13.5 μmol), palladium (II) acetate (15.1 mg, 67.3 μmol) and sodium tert-butoxide (77.6 mg, 808 μmol, Eq: 3) in DMF (1 mL) and toluene (500 μL) was heated in a microwave at 140° C. for 20 min. The reaction mixture was diluted with water then extracted into ethyl acetate (3×). The combined organic extracts were washed with brine then dried over magnesium sulfate. Purification by chromatography (15-45% dichloromethane/[10% dichloromethane/methanol/0.5% ammonium hydroxide]) gave N-tert-butyl-2(2(dimethylcarbamoyl)phenylamino)-5H-pyrrolo[2,3-b]pyrazine-7-carboxamide (16 mg, 42.1 μmol, 16%) as an off-white solid. ¹H NMR (400 MHz, DMSO-d) δ ppm: 12.25 (s, 1H), 8.77 (s, 1H), 8.06 (s, 1H), 7.96 (d, J=3.0, 1 H), 7.91 (d, J=7.9, 1 H), 7.78 (s, 1H), 7.38 (t, J=7.7, 1 H), 7.30 (d, J=7.5, 1 H), 7.11 (t, J=7.5, 1 H), 2.88 (s, 3H), 2.80 (s, 3H), 1.27 (s, 9H); MS (EI/CI) m/z: 381.2 [M+H].

Example 16

N-tert-Butyl-2-(1,5-dimethyl-1H-pyrazol-4-ylamino)-5H-pyrrolo[2,3-b]pyrazine-7-carboxamide

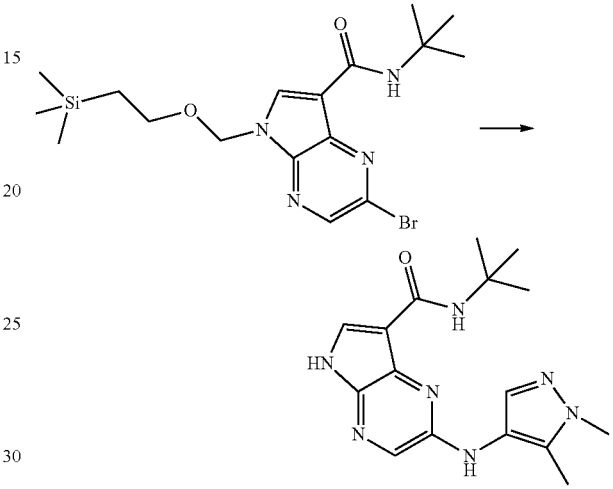

Step 1

A mixture of 2-bromo-N-tert-butyl-5-((2-(trimethylsilyl)ethoxy)methyl)-5H-pyrrolo[2,3-b]pyrazine-7-carboxamide (150 mg, 351 mol), 1,5-dimethyl-1H-pyrazol-4-amine dihydrochloride (96.9 mg, 526 mol), BINAP (10.9 mg, 17.5 mol), palladium (II) acetate (19.7 mg, 87.7 mol) and sodium tert-butoxide (118 mg, 1.23 mmol) in DMF (1 mL) and toluene (500 L) was heated in a microwave at 140° C. for 20 min. The reaction mixture was diluted with water then extracted into ethyl acetate (3×). The combined organic extracts were washed with brine then dried over magnesium sulfate. Purification by chromatography (50-100% ethyl acetate in hexanes) gave N-tert-butyl-2-(1,5-dimethyl-1H-pyrazol-4-ylamino)-5-((2-(trimethylsilyl)ethoxy)methyl)-5H-pyrrolo[2,3-b]pyrazine-7-carboxamide (45 mg, 98.3 mol, 28%) as a yellow gum. (EI/CI) m/z: 458.3 [M+H].

Step 2

To a solution of N-tert-butyl-2-(1,5-dimethyl-1H-pyrazol-4-ylamino)-5-((2-(trimethylsilyl)ethoxy)methyl)-5H-pyrrolo[2,3-b]pyrazine-7-carboxamide (45 mg, 98.3 μmol) in dichloromethane (1.5 mL) was added trifluoroacetic acid (224 mg, 152 μL, 1.97 mmol) and the mixture stirred at room temperature for 16 h. The reaction mixture was concentrated in vacuo and the residue obtained diluted with dichloromethane (1.5 mL), methanol (0.75 mL) and ammonium hydroxide (0.2 mL) and stirred at room temperature for 2 h. The reaction mixture was concentrated then purified by chromatography (silica, 10-45% of a 1:4 methanol:dichloromethane solution in dichloromethane) to give N-tert-butyl-2-(1,5-dimethyl-1H-pyrazol-4-ylamino)-5H-pyrrolo[2,3-b]pyrazine-7-carboxamide (18 mg, 55.0 μmol, 56%) as a yellow solid. ¹H NMR (400 MHz, DMSO-d) δ ppm: 12.10 (s, 1H), 8.39 (s, 1H), 7.87 (s, 1H), 7.86 (s, 1H), 7.85 (d, J=3.3, 1 H), 3.71 (s, 3H), 2.16 (s, 3H), 1.30 (s, 9H); MS (EI/CI) m/z: 328.2 [M+H].

Example 17

N-(1-Hydroxy-2-methylpropan-2-yl)-2-(1-methyl-1H-pyrazol-4-ylamino)-5H-pyrrolo[2,3-b]pyrazine-7-carboxamide

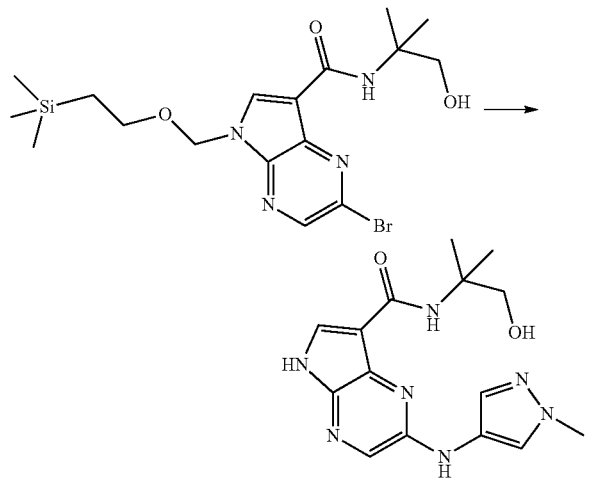

Step 1

A mixture of 2-bromo-N-(1-hydroxy-2-methylpropan-2-yl)-5-((2-(trimethylsilyl)ethoxy)methyl)-5H-pyrrolo[2,3-b]pyrazine-7-carboxamide (150 mg, 338 mol), 1-methyl-1H-pyrazol-4-amine hydrochloride (67.8 mg, 526 mol), BINAP (10.5 mg, 16.9 mol), palladium (II) acetate (19.0 mg, 84.6 mol) and sodium tert-butoxide (81.3 mg, 846 mol) in DMF (1 mL) and toluene (500 L) was heated in a microwave at 140° C. for 20 min. The reaction mixture was diluted with water then extracted into ethyl acetate (3×). The combined organic extracts were washed with brine then dried over magnesium sulfate. Purification by chromatography (silica, 20-65% of a 10:89.5:0.5 methanol:dichloromethane:ammonium hydroxide solution in dichloromethane) gave N-(1-hydroxy-2-methylpropan-2-yl)-2-(1-methyl-1H-pyrazol-4-ylamino)-5-((2-(trimethylsilyl)ethoxy)methyl)-5H-pyrrolo[2,3-b]pyrazine-7-carboxamide (28 mg, 60.9 mol, 18%) as a light yellow solid. (EI/CI) m/z: 460.3 [M+H].

Step 2

To a solution of N-(1-hydroxy-2-methylpropan-2-yl)-2-(1-methyl-1H-pyrazol-4-ylamino)-5-((2-(trimethylsilyl)ethoxy)methyl)-5H-pyrrolo[2,3-b]pyrazine-7-carboxamide (26 mg, 56.6 mol) in dichloromethane (1 mL) was added trifluoroacetic acid (129 mg, 87.2 µL, 1.13 mmol) and the mixture stirred at room temperature for 16 h. The reaction mixture was concentrated in vacuo and the residue obtained diluted with dichloromethane (1 mL), methanol (0.5 mL) and ammonium hydroxide (0.15 mL) and stirred at room temperature for 2 h. The mixture was concentrated and triturated with water. The solid was collected by filtration and washed with water and ether to give N-(1-hydroxy-2-methylpropan-2-yl)-2-(1-methyl-1H-pyrazol-4-ylamino)-5H-pyrrolo[2,3-b]pyrazine-7-carboxamide (12 mg, 36.4 mol, 64%) as a brown solid. ¹H NMR (400 MHz, DMSO-d) δ ppm: 12.19 (s, 1H), 9.16 (s, 1H), 8.01 (s, 1H), 7.91 (d, J=3.0, 1 H), 7.86 (s, 1H), 7.70 (s, 1H), 7.49 (s, 1H), 5.15 (t, J=5.7, 1 H), 3.82 (s, 3H), 3.57 (d, J=5.9, 2 H), 1.37 (s, 9H); MS (EI/CI) m/z: 330.2 [M+H].

Example 18

N-tert-Butyl-2-(3-methylisothiazol-5-ylamino)-5H-pyrrolo[2,3-b]pyrazine-7-carboxamide

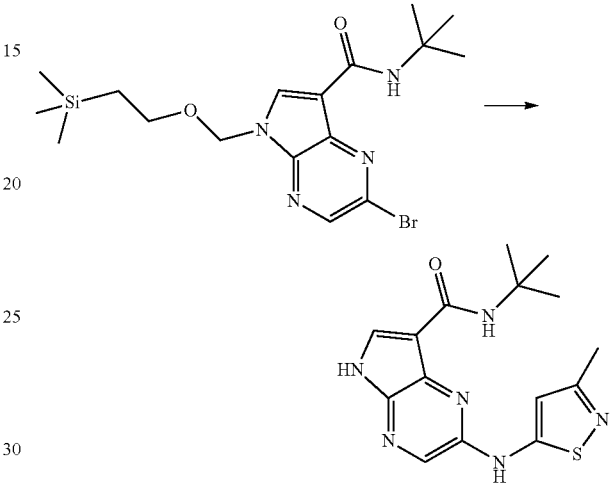

Step 1

A mixture of 2-bromo-N-tert-butyl-5-((2-(trimethylsilyl)ethoxy)methyl)-5H-pyrrolo[2,3-b]pyrazine-7-carboxamide (150 mg, 351 mol), 3-methylisothiazol-5-amine hydrochloride (79.3 mg, 526 mol), BINAP (10.9 mg, 17.5 mol), palladium (II) acetate (19.7 mg, 87.7 mol) and sodium tert-butoxide (101 mg, 1.05 mmol, Eq: 3) in DMF (1.2 mL) and toluene (600 µL) was heated in a microwave at 140° C. for 20 min. The reaction mixture was diluted with water then extracted into ethyl acetate (3×). The combined organic extracts were washed with brine then dried over magnesium sulfate. Purification by chromatography (silica, 50-100% ethyl acetate in hexanes) gave N-tert-butyl-2-(3-methylisothiazol-5-ylamino)-5-((2-(trimethylsilyl)ethoxy)methyl)-5H-pyrrolo[2,3-b]pyrazine-7-carboxamide (32 mg, 69.5 mol, 20%) as a yellow solid. (EI/CI) m/z: 461.3 [M+H].

Step 2

To a solution of N-tert-butyl-2-(3-methylisothiazol-5-ylamino)-5-((2-(trimethylsilyl)ethoxy)methyl)-5H-pyrrolo[2,3-b]pyrazine-7-carboxamide (32 mg, 69.5 mol) in dichloromethane (1.2 mL) was added trifluoroacetic acid (158 mg, 107 µL, 1.39 mmol) and the mixture stirred at room temperature for 16 h. The reaction mixture was concentrated in vacuo and the residue obtained diluted with dichloromethane (1.2 mL), methanol (0.6 mL) and ammonium hydroxide (0.15 mL) and stirred at room temperature for 2 h. The mixture was concentrated and triturated with water. The solid was collected by filtration and washed with water and ether to give N-tert-butyl-2-(3-methylisothiazol-5-ylamino)-5H-pyrrolo[2,3-b]pyrazine-7-carboxamide (18 mg, 54.5 mol, 78.4%) as a brown solid. ¹H NMR (400 MHz, DMSO-d) δ ppm: 12.55

(s, 1H), 11.39 (s, 1H), 8.15 (d, J=3.2, 1 H), 8.11 (s, 1H), 7.37 (s, 1H), 6.70 (s, 1H), 2.33 (s, 3H), 1.55 (s, 9H); MS (EI/CI) m/z: 331.1 [M+H].

Example 19

N-tert-Butyl-2-(2,4-dimethylphenylamino)-5H-pyrrolo[2,3-b]pyrazine-7-carboxamide

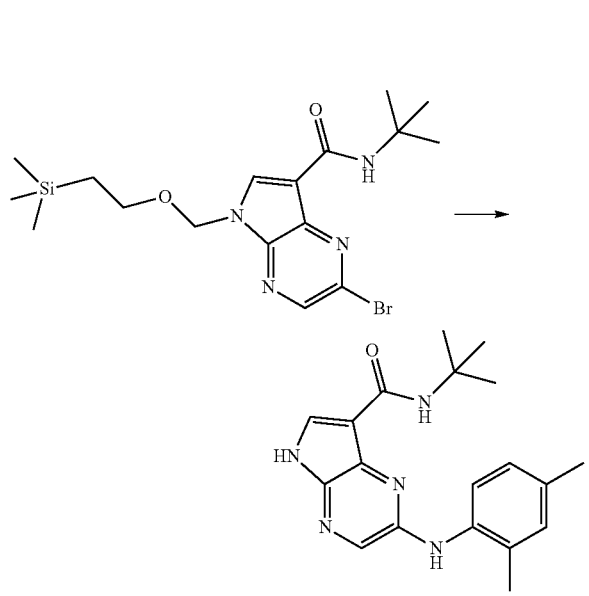

Step 1

A mixture of 2-bromo-N-tert-butyl-5-((2-(trimethylsilyl)ethoxy)methyl)-5H-pyrrolo[2,3-b]pyrazine-7-carboxamide (200 mg, 468 mol), 2,4-dimethylaniline (85.1 mg, 526 mol), BINAP (14.6 mg, 23.4 mol), palladium (II) acetate (26.3 mg, 117 mol) and sodium tert-butoxide (112 mg, 1.17 mmol) in DMF (1 mL) and toluene (500 µL) was heated in a microwave at 140° C. for 20 min. The reaction mixture was diluted with water then extracted into ethyl acetate (3×). The combined organic extracts were washed with brine then dried over magnesium sulfate. Purification by chromatography (silica, 20-60% ethyl acetate in hexanes) gave N-tert-butyl-2-(2,4-dimethylphenylamino)-5-((2-(trimethylsilyl)ethoxy)methyl)-5H-pyrrolo[2,3-b]pyrazine-7-carboxamide (82 mg, 175 mol, 37.5%) as a brown gum. (EI/CI) m/z: 468.4 [M+H].

Step 2

To a solution of N-tert-butyl-2-(2,4-dimethylphenylamino)-5-((2-(trimethylsilyl)ethoxy)methyl)-5H-pyrrolo[2,3-b]pyrazine-7-carboxamide (82 mg, 175 mol) in dichloromethane (2.7 mL) was added trifluoroacetic acid (400 mg, 270 µL, 3.51 mmol) and the mixture stirred at room temperature for 16 h. The reaction mixture was concentrated in vacuo and the residue obtained diluted with dichloromethane (3 mL), methanol (1.5 mL) and ammonium hydroxide (0.4 mL) and stirred at room temperature for 1 h. The mixture was concentrated and triturated with water. The solid was collected by filtration and washed with water and ether to give N-tert-butyl-2-(2,4-dimethylphenylamino)-5H-pyrrolo[2,3-b]pyrazine-7-carboxamide (7 mg, 20.7 mol, 12%) as a yellow solid. $^1$H NMR (400 MHz, CDCl$_3$-d) δ ppm: 9.19 (s, 1H), 8.12 (d, J=3.0, 1 H), 7.95 (s, 1H), 7.86 (s, 1H), 7.50 (d, J=7.8, 1 H), 7.15 (s, 1H), 7.08 (d, J=8.2, 1 H), 6.33 (s, 1H), 2.38 (s, 3H), 2.34 (s, 1H), 1.49 (s, 9H); MS (EI/CI) m/z: 338.2 [M+H].

Example 20

N-tert-Butyl-2-(4-(methylsulfonyl)phenylamino)-5H-pyrrolo[2,3-b]pyrazine-7-carboxamide

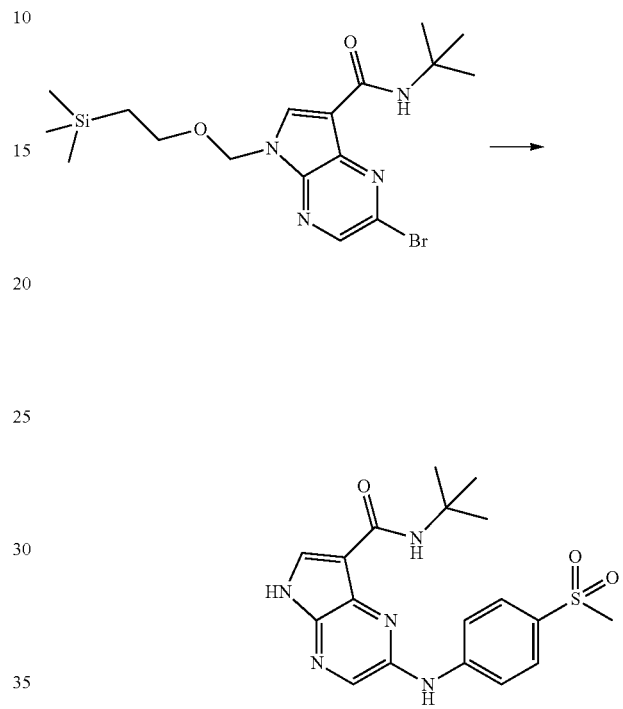

Step 1

A mixture of 2-bromo-N-tert-butyl-5-((2-(trimethylsilyl)ethoxy)methyl)-5H-pyrrolo[2,3-b]pyrazine-7-carboxamide (125 mg, 292 µmol), 4-(methylsulfonyl)aniline (75.1 mg, 439 µmol), xantphos (50.8 mg, 87.7 µmol), Pd$_2$(dba)$_3$ (26.8 mg, 29.2 µmol) and cesium carbonate (191 mg, 585 µmol) in dioxane (2 mL) was heated in a microwave at 150° C. for 20 min. The mixture was cooled, filtered through celite, and the filtrate concentrated in vacuo. Purification by chromatography (silica, 20-75% ethyl acetate in hexanes) gave N-tert-butyl-2-(4-(methylsulfonyl)phenylamino)-5-((2-(trimethylsilyl)ethoxy)methyl)-5H-pyrrolo[2,3-b]pyrazine-7-carboxamide (90 mg, 174 µmol, 59%) as a light yellow solid. (EI/CI) m/z: 518.3 [M+H].

Step 2

N-tert-butyl-2-(4-(methylsulfonyl)phenylamino)-5-((2-(trimethylsilyl)ethoxy)methyl)-5H-pyrrolo[2,3-b]pyrazine-7-carboxamide (90 mg, 174 µmol) was dissolved in dichloromethane (3 mL) and treated with trifluoroacetic acid (396 mg, 268 µL, 3.48 mmol). After stirring at room temperature for 16 h, the mixture was concentrated in vacuo then re-dissolved in dichloromethane (3 mL), methanol (1.5 mL) and ammonium hydroxide (0.35 mL) and the mixture stirred at room temperature for 1 h. The mixture was concentrated in vacuo then diluted with water, triturated and filtered. The solid obtained was washed with ether then dried to give N-tert-butyl-2-(4-(methylsulfonyl)phenylamino)-5H-pyrrolo[2,3-b]pyrazine-7-carboxamide (65 mg, 168 µmol, 97%) as a yellow solid. $^1$H NMR (400 MHz, DMSO-d) δ ppm: 12.55 (s, 1H), 10.12 (s, 1H), 8.19 (d, J=2.8, 1 H), 8.16 (s, 1H), 7.95 (d, J=8.8, 2 H), 7.88 (d, J=8.8, 2 H), 7.75 (s, 1H), 3.22 (s, 3H), 1.54 (s, 9H); MS (EI/CI) m/z: 388.2 [M+H].

Example 21

N-tert-Butyl-2-(methyl(pyridin-3-yl)amino)-5H-pyrrolo[2,3-b]pyrazine-7-carboxamide

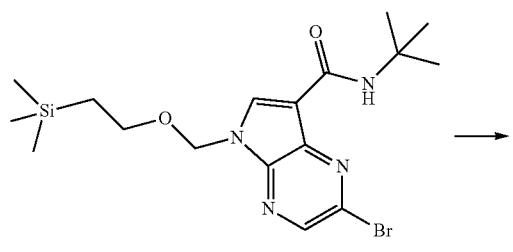

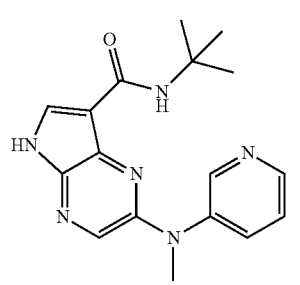

8.05 (d, J=3.1, 1 H), 7.96 (s, 1H), 7.92 (s, 1H), 7.82 (m, 1H), 7.46 (m, 1H), 3.50 (s, 3H), 1.32 (s, 9H); MS (EI/CI) m/z: 325.1 [M+H].

Example 22

N-tert-Butyl-2-(3-methylisoxazol-5-ylamino)-5H-pyrrolo[2,3-b]pyrazine-7-carboxamide

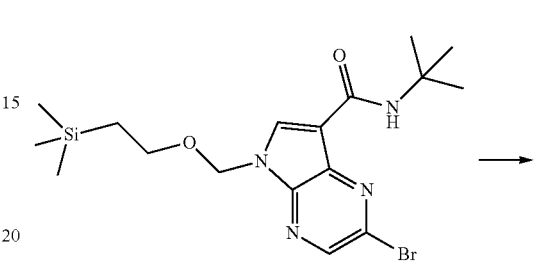

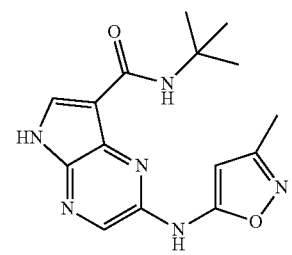

Step 1

A mixture of 2-bromo-N-tert-butyl-5-((2-(trimethylsilyl)ethoxy)methyl)-5H-pyrrolo[2,3-b]pyrazine-7-carboxamide (125 mg, 292 µmol), N-methylpyridin-3-amine (47.4 mg, 439 µmol), xantphos (50.8 mg, 87.7 µmol), Pd$_2$(dba)$_3$ (26.8 mg, 29.2 µmol) and cesium carbonate (191 mg, 585 µmol) in dioxane (2 mL) was heated in a microwave at 150° C. for 20 min. The mixture was cooled and then filtered through a pad of celite. The filtrate was concentrated in vacuo then purified by chromatography (silica, ethyl acetate in hexanes) to give N-tert-butyl-2-(methyl(pyridin-3-yl)amino)-5-((2-(trimethylsilyl)ethoxy)methyl)-5H-pyrrolo[2,3-b]pyrazine-7-carboxamide (38 mg, 83.6 µmol, 29%) as a yellow gum. (EI/CI) m/z: 455.4 [M+H].

Step 2

N-tert-butyl-2-(methyl(pyridin-3-yl)amino)-5-((2-(trimethylsilyl)ethoxy)methyl)-5H-pyrrolo[2,3-b]pyrazine-7-carboxamide (38 mg, 83.6 µmol) was dissolved in dichloromethane (1.5 mL) and treated with trifluoroacetic acid (191 mg, 129 µL, 1.67 mmol). After 16 h, the mixture was concentrated and the residue re-dissolved in dichloromethane (1.5 mL), methanol (0.75 mL) and ammonium hydroxide (0.2 mL) and the mixture stirred at room temperature for 1 h. The mixture was concentrated then triturated with water and filtered to obtain a solid. This was washed with ether then dried to give N-tert-butyl-2-(methyl(pyridin-3-yl)amino)-5H-pyrrolo[2,3-b]pyrazine-7-carboxamide (16 mg, 49.3 µmol, 59%) as a light yellow solid. $^1$H NMR (400 MHz, DMSO-d) δ ppm: 12.33 (s, 1H), 8.64 (d, J=2.5, 1 H), 8.40 (dd, J=4.7, 1.2, 1 H), Step 1

A mixture of 2-bromo-N-tert-butyl-5-((2-(trimethylsilyl)ethoxy)methyl)-5H-pyrrolo[2,3-b]pyrazine-7-carboxamide (125 mg, 292 mol), 3-methylisoxazol-5-amine (43.0 mg, 439 mol), xantphos (50.8 mg, 87.7 mol), Pd$_2$(dba)$_3$ (26.8 mg, 29.2 mol) and cesium carbonate (191 mg, 585 mol) in dioxane (2 mL) was heated in a microwave at 150° C. for 20 min. The mixture was cooled then filtered through a pad of celite. The filtrate was concentrated in vacuo then purified by chromatography (silica, 20-75% ethyl acetate in hexanes) to give N-tert-butyl-2-(3-methylisoxazol-5-ylamino)-5-((2-(trimethylsilyl)ethoxy)methyl)-5H-pyrrolo[2,3-b]pyrazine-7-carboxamide (33 mg, 74.2 mol, 25.4%) as a yellow solid. (EI/CI) m/z: 455.3 [M+H].

Step 2

N-tert-Butyl-2-(3-methylisoxazol-5-ylamino)-5-((2-(trimethylsilyl)ethoxy)methyl)-5H-pyrrolo[2,3-b]pyrazine-7-carboxamide (33 mg, 74.2 mol) was dissolved in dichloromethane (1.3 mL) and treated with trifluoroacetic acid (169 mg, 114 µL, 1.48 mmol). The mixture was stirred at room temperature for 16 h, then concentrated and re-dissolved in dichloromethane (1.3 mL), methanol (0.65 mL) and ammonium hydroxide (0.2 mL) and stirred at room temperature for 1 h. The mixture was concentrated and diluted with water, triturated and filtered. The solid obtained was washed with ether and dried to give N-tert-butyl-2-(3-methylisoxazol-5-ylamino)-5H-pyrrolo[2,3-b]pyrazine-7-carboxamide (16 mg, 45.8 mol, 62%) as a yellow solid. $^1$H NMR (400 MHz, DMSO-d) δ ppm: 12.53 (s, 1H), 11.06 (s, 1H), 8.14 (d, J=3.0, 1 H), 8.09 (s, 1H), 7.57 (s, 1H), 6.18 (s, 1H), 2.17 (s, 3H), 1.48 (s, 9H); MS (EI/CI) m/z: 315.1 [M+H].

Example 23

N-tert-Butyl-2-(6-(methylsulfonyl)pyridin-3-ylamino)-5H-pyrrolo[2,3-b]pyrazine-7-carboxamide

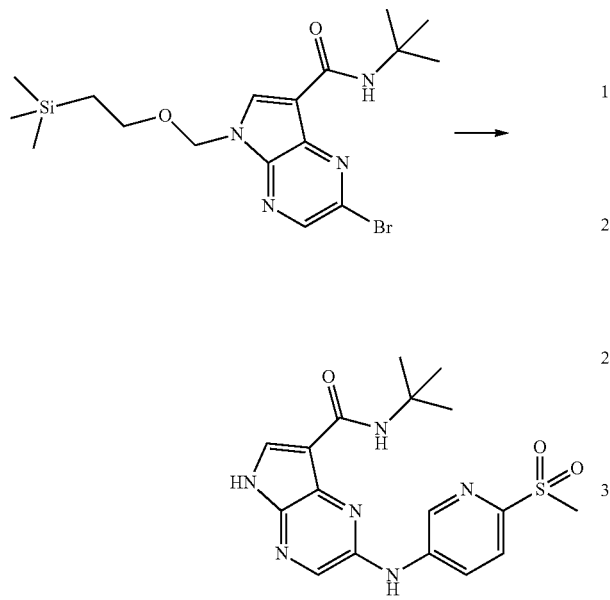

Step 1

A mixture of 2-bromo-N-tert-butyl-5-((2-(trimethylsilyl)ethoxy)methyl)-5H-pyrrolo[2,3-b]pyrazine-7-carboxamide (150 mg, 351 µmol), 6-(methylsulfonyl)pyridin-3-amine (90.7 mg, 526 µmol), xantphos (60.9 mg, 105 µmol), Pd₂(dba)₃ (32.1 mg, 35.1 µmol) and cesium carbonate (229 mg, 702 µmol) in dioxane (2.4 mL) was heated in a microwave at 150° C. for 20 min. The mixture was cooled then filtered through a pad of celite. The filtrate was concentrated in vacuo then purified by chromatography (silica, 20-95% ethyl acetate in hexanes) to give N-tert-butyl-2-(6-(methylsulfonyl)pyridin-3-ylamino)-5-((2-(trimethylsilyl)ethoxy)methyl)-5H-pyrrolo[2,3-b]pyrazine-7-carboxamide (97 mg, 187 µmol, 53%) as a yellow solid. (EI/CI) m/z: 458.3 [M+H].

Step 2

N-tert-Butyl-2-(6-(methylsulfonyl)pyridin-3-ylamino)-5-((2-(trimethylsilyl)ethoxy)methyl)-5H-pyrrolo[2,3-b]pyrazine-7-carboxamide (97 mg, 187 µmol) was dissolved in dichloromethane (2.88 mL) and treated with trifluoroacetic acid (426 mg, 288 µL, 3.74 mmol). The mixture was stirred at room temperature for 16 h. The mixture was concentrated then re-dissolved in dichloromethane (3 mL), methanol (1.5 mL) and ammonium hydroxide (0.5 mL) and the mixture stirred at room temperature for 1 h. The mixture was concentrated in vacuo then triturated with water and filtered. The solid obtained was washed with ether then dried to give N-tert-butyl-2-(6-(methylsulfonyl)pyridin-3-ylamino)-5H-pyrrolo[2,3-b]pyrazine-7-carboxamide (71 mg, 183 µmol, 98%) as a yellow solid. ¹H NMR (400 MHz, DMSO-d) δ ppm: 12.51 (s, 1H), 10.26 (s, 1H), 8.99 (d, J=2.5, 1 H) 8.37 (dd, J=8.4, 2.7, 1 H), 8.14 (s, 1H), 8.11 (s, 1H), 7.92 (d, J=8.7, 1 H), 7.62 (s, 1H), 3.21 (s, 3H), 1.45 (s, 9H); MS (EI/CI) m/z: 389.2 [M+H].

Example 24

N-tert-Butyl-2-(3-(1-hydroxyethyl)phenylamino)-5H-pyrrolo[2,3-b]pyrazine-7-carboxamide Step 1

A mixture of 2-bromo-N-tert-butyl-5-((2-(trimethylsilyl)ethoxy)methyl)-5H-pyrrolo[2,3-b]pyrazine-7-carboxamide (150 mg, 351 µmol), 1-(3-aminophenyl)ethanol (72.2 mg, 526 µmol), xantphos (60.9 mg, 105 µmol), Pd₂(dba)₃ (32.1 mg, 35.1 µmol) and cesium carbonate (229 mg, 702 µmol) in dioxane (2 mL) was heated in a microwave at 150° C. for 20 min. The mixture was cooled then filtered through a pad of celite. The filtrate was concentrated in vacuo then purified by chromatography (silica, 40-70% ethyl acetate in hexanes) to give N-tert-butyl-2-(3-(1-hydroxyethyl)phenylamino)-5-((2-(trimethylsilyl)ethoxy)methyl)-5H-pyrrolo[2,3-b]pyrazine-7-carboxamide (143 mg, 148 µmol, 42%) as a yellow solid. (EI/CI) m/z: 519.3 [M+H].

Step 2

N-tert-Butyl-2-(3-(1-hydroxyethyl)phenylamino)-5-((2-(trimethylsilyl)ethoxy)methyl)-5H-pyrrolo[2,3-b]pyrazine-7-carboxamide (143 mg, 296 mol) was dissolved in dichloromethane (4.5 mL) and treated with trifluoroacetic acid (674 mg, 456 µL, 5.91 mmol). The mixture was stirred at room temperature for 16 h. The mixture was concentrated then re-dissolved in dichloromethane (4 mL), methanol (3 mL) and ammonium hydroxide (0.7 mL) and the mixture stirred at room temperature for 2 h. The reaction mixture was concentrated then purified by chromatography (silica, methanol in dichloromethane) gave N-tert-butyl-2-(3-(1-hydroxyethyl)phenylamino)-5H-pyrrolo[2,3-b]pyrazine-7-carboxamide (55 mg, 156 µmol, 53%) as a yellow solid. ¹H NMR (400 MHz, DMSO-d) δ ppm: 12.29 (s, 1H), 9.44 (s, 1H), 8.00 (s, 1H), 7.99 (s, 1H), 7.98 (d, J=2.8, 1 H), 7.78 (s, 1H), 7.19 (m, 2H), 6.91 (d, J=7.5, 1 H), 5.17 (d, J=4.0, 1 H), 4.70 (m, 1H), 3.38 (q, J=7.2, 1 H), 1.43 (s, 9H), 1.34 (d. J=6.3, 3 H), 1.09 (t, J=7.2, 1 H); MS (EI/CI) m/z: 354.2 [M+H].

Example 25

N-tert-Butyl-2-(2-methoxypyrimidin-5-ylamino)-5H-pyrrolo[2,3-b]pyrazine-7-carboxamide

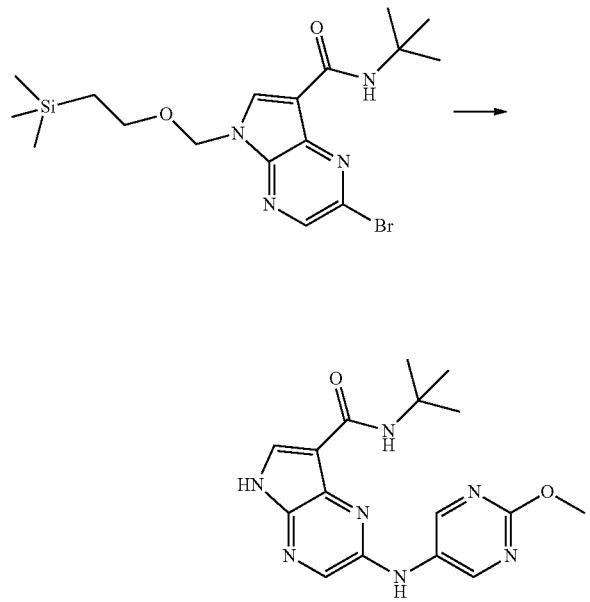

Step 1

A mixture of 2-bromo-N-tert-butyl-5-((2-(trimethylsilyl)ethoxy)methyl)-5H-pyrrolo[2,3-b]pyrazine-7-carboxamide (150 mg, 351 μmol), 2-methoxypyrimidin-5-amine (65.9 mg, 526 μmol), xantphos (60.9 mg, 105 μmol), Pd$_2$(dba)$_3$ (32.1 mg, 35.1 μmol) and cesium carbonate (229 mg, 702 μmol) in dioxane (2 mL) was heated in a microwave at 150° C. for 20 min. The mixture was cooled then filtered through a pad of celite. The filtrate was concentrated in vacuo then purified by chromatography (silica, 40-80% ethyl acetate in hexanes) to give N-tert-butyl-2-(2-methoxypyrimidin-5-ylamino)-5-((2-(trimethylsilyl)ethoxy)methyl)-5H-pyrrolo[2,3-b]pyrazine-7-carboxamide (99 mg, 210 μmol, 60%) as a yellow solid. (EI/CI) m/z: 484.3 [M+H].

Step 2

N-tert-Butyl-2-(2-methoxypyrimidin-5-ylamino)-5-((2-(trimethylsilyl)ethoxy)methyl)-5H-pyrrolo[2,3-b]pyrazine-7-carboxamide (100 mg, 212 μmol) was dissolved in dichloromethane and treated with trifluoroacetic acid (484 mg, 327 μL, 4.24 mmol). The mixture was stirred at room temperature for 16 h. The mixture was concentrated then re-dissolved in dichloromethane (3 mL), methanol (1.5 mL) and ammonium hydroxide (0.45 mL) and the mixture stirred at room temperature for 1 h. The mixture was concentrated in vacuo then triturated with water and filtered. The solid obtained was washed with ether then dried to give N-tert-butyl-2-(2-methoxypyrimidin-5-ylamino)-5H-pyrrolo[2,3-b]pyrazine-7-carboxamide (64 mg, 187 μmol, 88%) as a yellow solid. $^1$H NMR (400 MHz, DMSO-d) δ ppm: 12.35 (s, 1H), 9.48 (s, 1H), 8.86 (s, 2H), 8.01 (s, 1H), 7.97 (s, 1H), 7.63 (s, 1H), 3.88 (s, 3H), 1.38 (s, 9H); MS (EI/CI) m/z: 342.1 [M+H].

Example 26

N-(1-Hydroxy-2-methylpropan-2-yl)-2-(pyridin-3-ylamino)-5H-pyrrolo[2,3-b]pyrazine-7-carboxamide

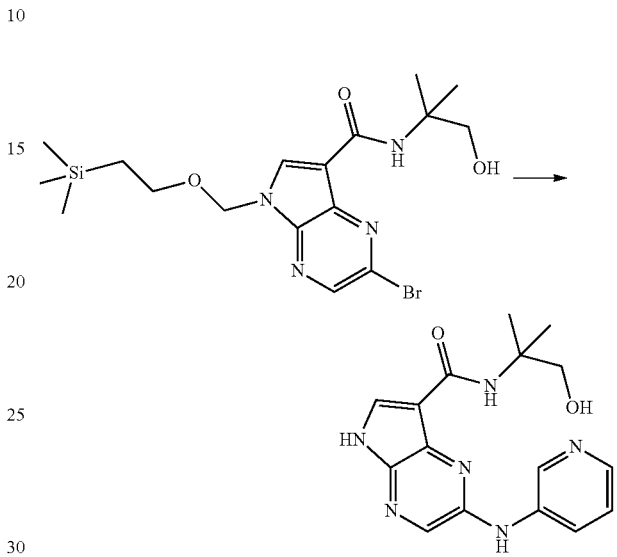

Step 1

A mixture of 2-bromo-N-(1-hydroxy-2-methylpropan-2-yl)-5-((2-(trimethylsilyl)ethoxy)methyl)-5H-pyrrolo[2,3-b]pyrazine-7-carboxamide (150 mg, 338 μmol), pyridin-3-amine (47.8 mg, 507 μmol), xantphos (58.7 mg, 101 μmol), Pd$_2$(dba)$_3$ (31.0 mg, 33.8 μmol) and cesium carbonate (220 mg, 677 μmol) in dioxane (2 mL) was heated in a microwave at 150° C. for 20 min. The mixture was cooled then filtered through a pad of celite. The filtrate was concentrated in vacuo then purified by chromatography (silica, 40-100% ethyl acetate in hexanes gradient then dichloromethane/methanol) to give N-(1-hydroxy-2-methylpropan-2-yl)-2-(pyridin-3-ylamino)-5-((2-(trimethylsilyl)ethoxy)methyl)-5H-pyrrolo[2,3-b]pyrazine-7-carboxamide (32 mg, 59.6 μmol, 18%) as a light yellow solid. (EI/CI) m/z: 472.3 [M+H].

Step 2

N-(1-Hydroxy-2-methylpropan-2-yl)-2-(pyridin-3-ylamino)-5-((2-(trimethylsilyl)ethoxy)methyl)-5H-pyrrolo[2,3-b]pyrazine-7-carboxamide (32 mg, 70.1 μmol) was dissolved in dichloromethane (1.2 mL) and treated with trifluoroacetic acid (160 mg, 108 μL, 1.4 mmol). The mixture was stirred at room temperature for 16 h. The mixture was concentrated then re-dissolved in dichloromethane (1 mL), methanol (0.5 mL) and ammonium hydroxide (0.2 mL) and the mixture stirred at room temperature for 1 h. The mixture was concentrated in vacuo then triturated with water and filtered. The solid obtained was washed with ether then dried to give N-(1-hydroxy-2-methylpropan-2-yl)-2-(pyridin-3-ylamino)-5H-pyrrolo[2,3-b]pyrazine-7-carboxamide (21 mg, 64.3 μmol, 92%) as a light yellow solid. $^1$H NMR (400 MHz, DMSO-d) δ ppm: 12.39 (s, 1H), 9.66 (s, 1H), 8.85 (d, J=2.5, 1 H), 8.21 (m, 1H), 8.16 (dd, J=4.7, 1.6, 1 H), 8.04 (s, 1H), 8.03 (s, 1H), 7.67 (s, 1H), 7.33 (m, 1H), 5.05 (t, J=5.6, 1 H), 3.58 (d, J=5.9, 2 H), 1.36 (s, 6H); MS (EI/CI) m/z: 327.1 [M+H].

Example 27

2-(3-(1-Aminoethyl)phenylamino)-N-tert-butyl-5H-pyrrolo[2,3-b]pyrazine-7-carboxamide

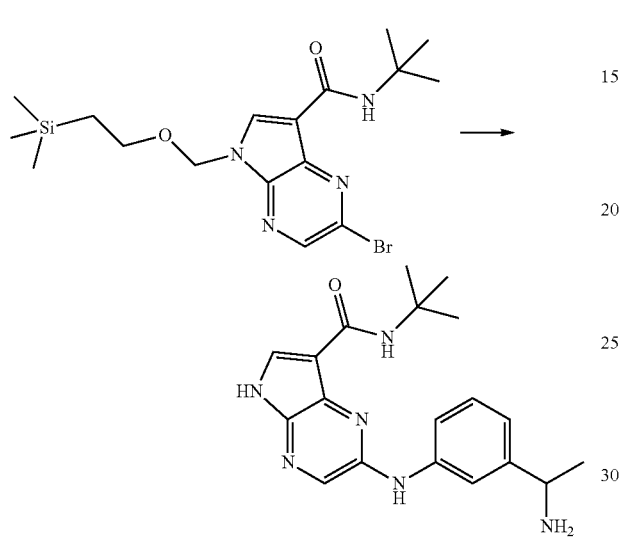

Step 1

A mixture of 2-bromo-N-tert-butyl-5-((2-(trimethylsilyl)ethoxy)methyl)-5H-pyrrolo[2,3-b]pyrazine-7-carboxamide (150 mg, 351 mol), tert-butyl 1-(3-aminophenyl)ethylcarbamate (124 mg, 526 mol), xantphos (60.9 mg, 105 mol), Pd$_2$(dba)$_3$ (32.1 mg, 35.1 mol) and cesium carbonate (229 mg, 702 mol) in dioxane (2 mL) was heated in a microwave at 150° C. for 20 min. The mixture was cooled then filtered through a pad of celite. The filtrate was concentrated in vacuo then purified by chromatography (silica, 20-40% ethyl acetate in hexanes) gave tert-butyl 1-(3-(7-(tert-butylcarbamoyl)-5-((2-(trimethylsilyl)ethoxy)methyl)-5H-pyrrolo[2,3-b]pyrazin-2-ylamino)phenyl)ethylcarbamate (150 mg, 257 mol, 73%) as a yellow gum. (EI/CI) m/z: 583.5 [M+H].

Step 2

To a solution of tert-butyl 1-(3-(7-(tert-butylcarbamoyl)-5-((2-(trimethylsilyl)ethoxy)methyl)-5H-pyrrolo[2,3-b]pyrazin-2-ylamino)phenyl)ethylcarbamate (150 mg, 257 mol) in dichloromethane (4 mL) was added trifluoroacetic acid (587 mg, 397 µL, 5.15 mmol) and the mixture stirred at room temperature for 16 h. The mixture was concentrated then re-dissolved in dichloromethane (4 mL), methanol (2 mL) and ammonium hydroxide (0.7 mL) and the mixture stirred at room temperature for 1 h. The reaction mixture was concentrated then purified by chromatography (silica, 6-10% methanol/dichloromethane) to give 2-(3-(1-aminoethyl)phenylamino)-N-tert-butyl-5H-pyrrolo[2,3-b]pyrazine-7-carboxamide (64 mg, 182 mol, 71%) as a yellow solid. $^1$H NMR (400 MHz, DMSO-d) δ ppm: 9.44 (s, 1H), 8.01 (s, 1H), 7.99 (d, J=7.9, 1 H), 7.98 (s, 1H), 7.77 (s, 1H), 7.22 (t, J=7.8, 1 H), 7.20 (s, 1H), 6.98 (d, J=7.8, 1 H), 4.05 (q, J=6.1, 1 H), 1.43 (s, 9H), 1.32 (d, J=6.5, 3 H); MS (EI/CI) m/z: 353.2 [M+H].

Example 28

N-tert-Butyl-2-(2-(methylsulfonyl)pyridin-4-ylamino)-5H-pyrrolo[2,3-b]pyrazine-7-carboxamide

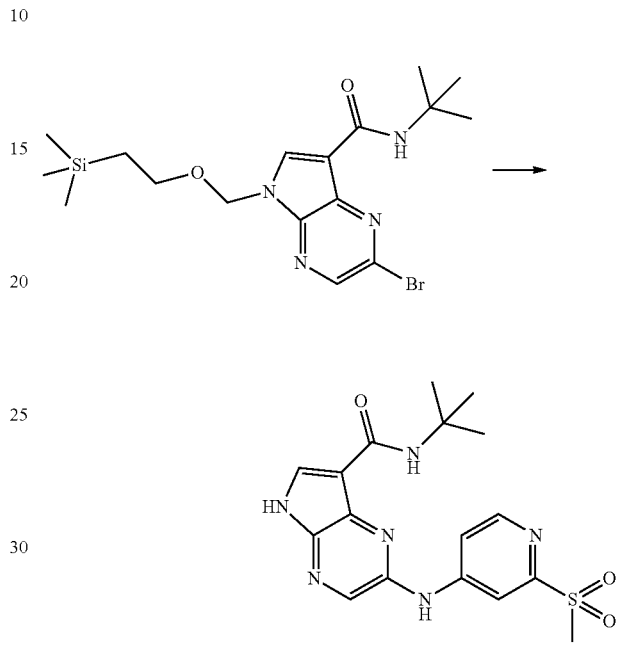

Step 1

A mixture of 2-bromo-N-tert-butyl-5-((2-(trimethylsilyl)ethoxy)methyl)-5H-pyrrolo[2,3-b]pyrazine-7-carboxamide (120 mg, 281 µmol), 2-(methylsulfonyl)pyridin-4-amine (55 mg, 319 µmol), xantphos (48.7 mg, 84.2 µmol), Pd$_2$(dba)$_3$ (25.7 mg, 28.1 µmol) and cesium carbonate (183 mg, 562 µmol) in dioxane (2 mL) was heated in a microwave at 150° C. for 20 min. The mixture was cooled then filtered through a pad of celite. The filtrate was concentrated in vacuo then purified by chromatography (silica, 35-70% ethyl acetate in hexanes) to give N-tert-butyl-2-(2-(methylsulfonyl)pyridin-4-ylamino)-5-((2-(trimethylsilyl)ethoxy)methyl)-5H-pyrrolo[2,3-b]pyrazine-7-carboxamide (127 mg, 245 µmol, 87%) as a light yellow gum. (EI/CI) m/z: 519.1 [M+H].

Step 2

To a solution of N-tert-butyl-2-(2-(methylsulfonyl)pyridin-4-ylamino)-5-((2-(trimethylsilyl) ethoxy)methyl)-5H-pyrrolo[2,3-b]pyrazine-7-carboxamide (127 mg, 245 µmol) in dichloromethane was added trifluoroacetic acid (558 mg, 377 µL, 4.9 mmol) and the mixture stirred at room temperature for 16 h. The mixture was concentrated then re-dissolved in dichloromethane (4 mL), methanol (2 mL) and ammonium hydroxide (0.7 mL) and the mixture stirred at room temperature for 1 h. The mixture was concentrated in vacuo then triturated with water and filtered. The solid obtained was washed with ether then dried to give N-tert-butyl-2-(2-(methylsulfonyl)pyridin-4-ylamino)-5H-pyrrolo[2,3-b]pyrazine-7-carboxamide (94 mg, 242 µmol, 99%) as an off white solid. $^1$H NMR (400 MHz, DMSO-d) δ ppm: 12.51 (s, 1H), 10.36 (s, 1H), 8.39 (d, J=5.9, 1 H), 8.10 (s, 1H), 8.01 (s, 1H), 7.99 (dd, J=5.3, 2.3, 1 H), 7.83 (d, J=2.1, 1 H), 7.52 (s, 1H), 3.15 (s, 3H), 1.35 (s, 9H); MS (EI/CI) m/z: 389.1 [M+H].

Example 29

N-tert-Butyl-2-(5-(methylsulfonyl)pyridin-3-ylamino)-5H-pyrrolo[2,3-b]pyrazine-7-carboxamide

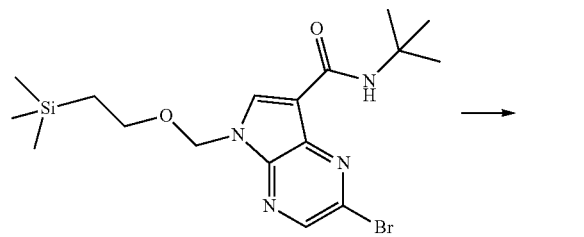

Step 1

To a mixture of 2-amino-N-tert-butyl-5-((2-(trimethylsilyl)ethoxy)methyl)-5H-pyrrolo[2,3-b]pyrazine-7-carboxamide (92 mg, 253 mol), 3-bromo-5-(methylsulfonyl)pyridine (77.7 mg, 329 mol), xantphos (43.9 mg, 75.9 mol), Pd$_2$(dba)$_3$ (23.2 mg, 25.3 mol) and cesium carbonate (165 mg, 506 mol) in dioxane (2 mL) was heated in a microwave at 150° C. for 20 min. The mixture was cooled then filtered through a pad of celite. The filtrate was concentrated in vacuo then purified by chromatography (silica, 30-70% ethyl acetate in hexanes) to give N-tert-butyl-2-(5-(methylsulfonyl)pyridin-3-ylamino)-5-((2-(trimethylsilyl)ethoxy)methyl)-5H-pyrrolo[2,3-b]pyrazine-7-carboxamide (125 mg, 241 mol, 95%) as a yellow gum. (EI/CI) m/z: 519.3 [M+H].

Step 2

To a solution of N-tert-butyl-2-(5-(methylsulfonyl)pyridin-3-ylamino)-5-((2-(trimethylsilyl)ethoxy)methyl)-5H-pyrrolo[2,3-b]pyrazine-7-carboxamide (125 mg, 241 mol) in dichloromethane was added trifluoroacetic acid (550 mg, 371 μL, 4.82 mmol) and the mixture stirred at room temperature for 16 h. The mixture was concentrated then re-dissolved in dichloromethane (3.7 mL), methanol (1.6 mL) and ammonium hydroxide (0.5 mL) and the mixture stirred at room temperature for 1 h. The mixture was concentrated in vacuo then triturated with water and filtered. The solid obtained was washed with ether then dried to give N-tert-butyl-2-(5-(methylsulfonyl)pyridin-3-ylamino)-5H-pyrrolo[2,3-b]pyrazine-7-carboxamide (92 mg, 237 mol, 98%) as a yellow solid. $^1$H NMR (400 MHz, DMSO-d) δ ppm: 12.38 (s, 1H), 9.90 (s, 1H), 9.40 (d, J=2.5, 1 H), 8.55 (d, J=1.9, 1 H), 8.06 (t, J=2.2, 1H), 8.01 (s, 1H), 7.96 (s, 1H), 7.54 (s, 1H), 3.22 (s, 3H), 1.31 (s, 9H); MS (EI/CI) m/z: 389.1 [M+H].

Example 30

N-tert-Butyl-2-(1,3-dimethyl-1H-pyrazol-4-ylamino)-5H-pyrrolo[2,3-b]pyrazine-7-carboxamide

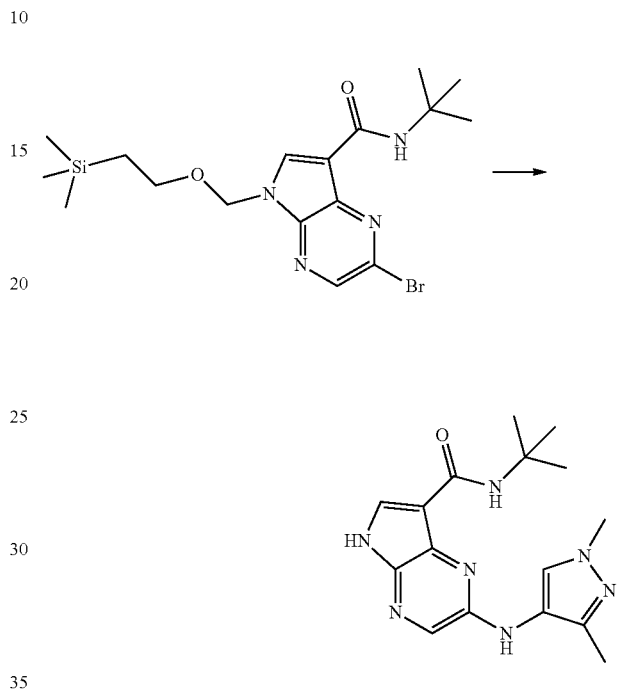

Step 1

A mixture of 2-bromo-N-tert-butyl-5-((2-(trimethylsilyl)ethoxy)methyl)-5H-pyrrolo[2,3-b]pyrazine-7-carboxamide (150 mg, 351 μmol), 1,3-dimethyl-1H-pyrazol-4-amine (58.5 mg, 526 μmol), xantphos (60.9 mg, 105 μmol), Pd$_2$(dba)$_3$ (32.1 mg, 35.1 μmol) and cesium carbonate (229 mg, 702 μmol) in dioxane (2 mL) was heated in a microwave at 150° C. for 20 min. The mixture was cooled then filtered through a pad of celite. The filtrate was concentrated in vacuo then purified by chromatography (silica, 25-100% ethyl acetate in hexanes) lo give N-tert-butyl-2-(1,3-dimethyl-1H-pyrazol-4-ylamino)-5-((2-(trimethylsilyl)ethoxy)methyl)-5H-pyrrolo[2,3-b]pyrazine-7-carboxamide (89 mg, 194 μmol, 55%) as a yellow gum. (EI/CI) m/z: 458.3 [M+H].

Step 2

To a solution of N-tert-butyl-2-(1,3-dimethyl-1H-pyrazol-4-ylamino)-5-((2-(trimethylsilyl)ethoxy)methyl)-5H-pyrrolo[2,3-b]pyrazine-7-carboxamide (89 mg, 194 μmol) in dichloromethane (3 mL) was added trifluoroacetic acid (443 mg, 300 μL, 3.89 mmol) and the mixture stirred at room temperature for 16 h. The mixture was concentrated then re-dissolved in dichloromethane (3 mL), methanol (1.5 mL) and ammonium hydroxide (0.45 mL) and the mixture stirred at room temperature for 2 h. The reaction mixture was concentrated then purified by chromatography (silica, 5-8% methanol in dichloromethane) to give N-tert-butyl-2-(1,3-dimethyl-1H-pyrazol-4-ylamino)-5H-pyrrolo[2,3-b]pyrazine-7-carboxamide (40 mg, 122 μmol, 63%) as a light brown solid. $^1$H NMR (400 MHz, DMSO-d) δ ppm: 12.13 (s, 1H), 8.44 (s, 1H), 7.91 (s, 1H), 7.87 (d, J=3.2, 1 H), 7.82 (s, 1H), 7.81 (s, 1H), 3.71 (s, 3H), 2.09 (s, 3H), 1.35 (s, 9H); MS (EI/CI) m/z: 328.1 [M+H].

Example 31

N-tert-Butyl-2-(3-methyl-1,2,4-thiadiazol-5-ylamino)-5H-pyrrolo[2,3-b]pyrazine-7-carboxamide

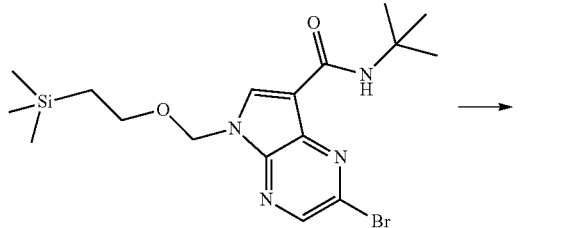

Step 1

A mixture of 2-bromo-N-tert-butyl-5-((2-(trimethylsilyl)ethoxy)methyl)-5H-pyrrolo[2,3-b]pyrazine-7-carboxamide (150 mg, 351 µmol), 3-methyl-1,2,4-thiadiazol-5-amine (60.6 mg, 526 µmol), xantphos (60.9 mg, 105 µmol), Pd$_2$(dba)$_3$ (32.1 mg, 35.1 µmol) and cesium carbonate (229 mg, 702 µmol) in dioxane (2 mL) was heated in a microwave at 150° C. for 20 min. Purification by chromatography (silica, 30-70% ethyl acetate in hexanes) gave N-tert-butyl-2-(3-methyl-1,2,4-thiadiazol-5-ylamino)-5-((2-(trimethylsilyl)ethoxy)methyl)-5H-pyrrolo[2,3-b]pyrazine-7-carboxamide (128 mg, 277 µmol, 79%) as an orange solid. (EI/CI) m/z: 462.3 [M+H].

Step 2

To a solution of N-tert-butyl-2-(3-methyl-1,2,4-thiadiazol-5-ylamino)-5-((2-(trimethylsilyl)ethoxy)methyl)-5H-pyrrolo[2,3-b]pyrazine-7-carboxamide (128 mg, 277 µmol) in dichloromethane (4.3 mL) was added trifluoroacetic acid (632 mg, 427 µL, 5.55 mmol) and the mixture stirred at room temperature for 16 h. The mixture was concentrated then re-dissolved in dichloromethane (4 mL), methanol (2 mL) and ammonium hydroxide (0.6 mL) and the mixture stirred at room temperature for 1 h. The mixture was concentrated in vacuo then triturated with water and filtered. The solid obtained was washed with ether then dried to give N-tert-butyl-2-(3-methyl-1,2,4-thiadiazol-5-ylamino)-5H-pyrrolo[2,3-b]pyrazine-7-carboxamide (90 mg, 272 µmol, 98%) as a light yellow solid. $^1$H NMR (400 MHz, DMSO-d) δ ppm: 12.80 (s, 1H), 12.57 (s, 1H), 8.35 (s, 1H), 8.34 (s, 1H), 7.34 (s, 1H), 2.53 (s, 3H), 1.62 (s, 9H); MS (EI/CI) m/z: 332.1 [M+H].

Example 32

N-tert-Butyl-2-(2-methyl-6,7-dihydro-2H-pyrazolo[4,3-b]pyridin-4(5H)-yl)-5H-pyrrolo[2,3-b]pyrazine-7-carboxamide

Step 1

4,5,6,7-Tetrahydro-1H-pyrazolo[4,3-b]pyridine

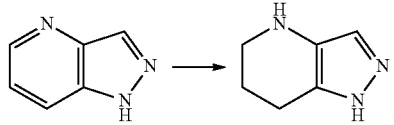 [SMILES: c1cnc2cn[nH]c2c1 ; c1n[nH]c2c1NCCC2]

A 250 mL Parr bottle was charged with a solution of 1H-pyrazolo[4,3-b]pyridine (2 g, 16.8 mmol, obtained from J&W PharmLab, LLC) in TFA (20.0 mL) and platinum(IV) oxide (381 mg, 1.68 mmol). The reaction mixture was evacuated twice with hydrogen and shaken under 55 psi pressure of hydrogen for 24 h. The reaction mixture was filtered over celite, and the filter cake washed with 5% methanol in CH$_2$Cl$_2$. The filtrate was concentrated in vacuo to afford a light brown oil that was dissolved in methanol (20 mL). Concentrated ammonium hydroxide solution was added drop wise until the pH remained basic (pH 8). The mixture was concentrated in vacuo then the residue adsorbed on silica gel and purified by chromatography (silica, 150 g column, 50 µm from Analogix, 0 to 5% of a 9:1 methanol:ammonium hydroxide solution in dichloromethane, 15 min) to give a yellow oil. This oil solidified upon drying under high vacuum to yield 4,5,6,7-tetrahydro-1H-pyrazolo[4,3-b]pyridine (1.712 g, 13.9 mmol, 83%) as a yellow solid. $^1$H NMR (CHLOROFORM-d) d: 7.09 (s, 1H), 3.14-3.25 (m, 2H), 2.76 (t, J=6.6 Hz, 2H), 1.88-2.02 (m, 2H). MS (EI/CI) m/z: 124.1 [M+H]$^+$.

Step 2 tert-Butyl 6,7-dihydro-1H-pyrazolo[4,3-b]pyridine-4(5H)-carboxylate

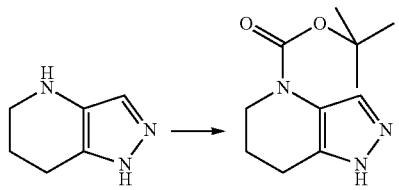 [SMILES: c1n[nH]c2c1NCCC2 ; CC(C)(C)OC(=O)N1CCCc2[nH]ncc21]

To a colorless solution of 4,5,6,7-tetrahydro-1H-pyrazolo[4,3-b]pyridine (168 mg, 1.36 mmol) in methanol (10 mL) was added di-tert-butyl dicarbonate (327 mg, 348 µL, 1.5 mmol) and the reaction was stirred at room temperature for 90 min. The solvents were evaporated under vacuum and the crude residue was purified by chromatography (40 g column, 50 m from Analogix, 0 to 5% 9:1 methanol:ammonium hydroxide in CH$_2$Cl$_2$, 20 min) to give tert-butyl 6,7-dihydro-1H-pyrazolo[4,3-b]pyridine-4(5H)-carboxylate (188 mg, 62%) as a colorless oil. $^1$H NMR (CHLOROFORM-d) δ: 11.38 (br. s., 1H), 7.43-8.06 (m, 1H), 3.69 (br. s., 2H), 2.75 (t, J=6.2 Hz, 2H), 1.89-2.02 (m, 2H), 1.43-1.65 (m, 9H). MS (EI/CI) m/z: 224.1 [M+H]+.

Step 3 tert-Butyl 2-methyl-6,7-dihydro-2H-pyrazolo[4,3-b]pyridine-4(5H)-carboxylate and tert-butyl 1-methyl-6,7-dihydro-1H-pyrazolo[4,3-b]pyridine-4(5H)-carboxylate

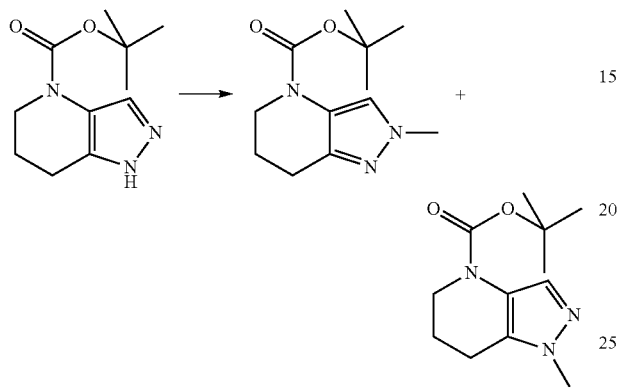

A solution of tert-butyl 6,7-dihydro-1H-pyrazolo[4,3-b]pyridine-4(5H)-carboxylate (188 mg, 842 mol) in N,N-dimethylformamide (5.0 mL) was cooled at 0° C. with stirring then a solution of potassium tert-butoxide (1M in THF, 1.18 mL, 1.18 mmol) was slowly added. After stirring for 30 min methyl iodide (167 mg, 73.7 μL, 1.18 mmol) was added. After 30 min the mixture was warmed to room temperature and stirred for an additional 18 h. The mixture was quenched with saturated NH$_4$Cl solution in water and the product was extracted with CH$_2$Cl$_2$ (3×30 mL).

The combined organics were dried over magnesium sulfate then concentrated in vacuo to an off-white solid. The solid was dissolved in toluene and purified by flash chromatography (115 g column, 50 m silica gel from Analogix, 0-20% ethyl acetate in hexanes, 15 min) to give two alkylation products. The less polar, N-2 alkylation product, tert-butyl 2-methyl-6,7-dihydro-2H-pyrazolo[4,3-b]pyridine-4(5H)-carboxylate (56 mg, 28%) was obtained as a light yellow solid $^1$H NMR (CHLOROFORM-d) δ: 7.22-7.78 (m, 1H), 3.78 (s, 3H), 3.56-3.70 (m, 2H), 2.71 (t, J=6.4 Hz, 2H), 1.87-2.00 (m, 2H), 1.46-1.59 (m, 9H). MS (EI/CI) m/z: 238.1 [M+H]. The more polar, N-1 alkylated product, tert-butyl 1-methyl-6,7-dihydro-1H-pyrazolo[4,3-b]pyridine-4(5H)-carboxylate (55 mg, 28%) was obtained as a light yellow solid. $^1$H NMR (CHLOROFORM-d) δ: 7.52 (br. s., 1H), 3.73 (s, 3H), 3.66 (br. s., 2H), 2.65 (t, J=6.4 Hz, 2H), 1.91-2.06 (m, 2H), 1.57 (br. s., 9H). MS (EI/CI) m/z: 238.1 [M+H].

Step 4

2-Methyl-4,5,6,7-tetrahydro-2H-pyrazolo[4,3-b]pyridine

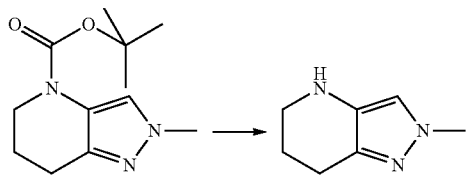

To a stirred solution of tert-butyl 2-methyl-6,7-dihydro-2H-pyrazolo[4,3-b]pyridine-4(5H)-carboxylate (56 mg, 236 mol) in CH$_2$Cl$_2$ (4.00 mL) was added TFA (740 mg, 500 μL, 6.49 mmol) at room temperature. After 18 h, the reaction mixture was concentrated in vacuo and the residue obtained was purified by chromatography (40 g column, 50 m silica-gel from Analogix, 0 to 5% 9:1 methanol:ammonium hydroxide in CH$_2$Cl$_2$, 20 min) to give 2-methyl-4,5,6,7-tetrahydro-2H-pyrazolo[4,3-b]pyridine (25 mg, 77%). $^1$H NMR (CHLOROFORM-d) δ: 6.81 (s, 1H), 3.75 (s, 3H), 3.11-3.18 (m, 2H), 3.04 (s, 1H), 2.73 (t, J=6.4 Hz, 2H), 1.86-2.00 (m, 2H).

Step 5

N-tert-Butyl-2-(2-methyl-6,7-dihydro-2H-pyrazolo[4,3-b]pyridin-4(5H)-yl)-5-((2-(trimethylsilyl)ethoxy)methyl)-5H-pyrrolo[2,3-b]pyrazine-7-carboxamide

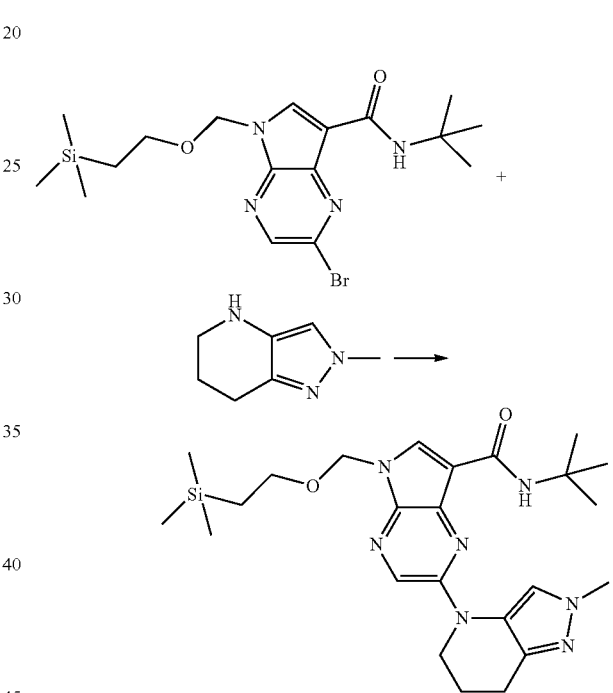

A microwave vial was charged with a mixture of 2-bromo-N-tert-butyl-5-((2-(trimethylsilyl)ethoxy)methyl)-5H-pyrrolo[2,3-b]pyrazine-7-carboxamide (77.9 mg, 182 μmol), 2-methyl-4,5,6,7-tetrahydro-2H-pyrazolo[4,3-b]pyridine (25 mg, 182 μmol), xantphos (31.6 mg, 54.7 μmol), Pd$_2$(dba)$_3$ (16.7 mg, 18.2 μmol) and Cs$_2$CO$_3$ (119 mg, 364 μmol) in dioxane (2 mL). The mixture was purged with argon and then heated to 150° C. for 20 min under microwave irradiation. The mixture was diluted with CH$_2$Cl$_2$ and then filtered through a pad of celite. The filtrate was concentrated in vacuo and the residue purified by chromatography (40 g column, 50 m silica-gel from Analogix, 0 to 5% 9:1 methanol:ammonium hydroxide in CH$_2$Cl$_2$, 20 min) to give N-tert-butyl-2-(2-methyl-6,7-dihydro-2H-pyrazolo[4,3-b]pyridin-4(5H)-yl)-5-((2-(trimethylsilyl)ethoxy)methyl)-5H-pyrrolo[2,3-b]pyrazine-7-carboxamide (87 mg, 99%) as a yellow foam. $^1$H NMR (CHLOROFORM-d) δ: 8.20 (s, 1H), 8.15 (s, 1H), 7.99 (s, 1H), 7.85 (s, 1H), 5.64 (s, 2H), 3.91 (s, 3H), 3.50-3.63 (m, 2H), 2.93 (t, J=6.6 Hz, 2H), 2.15-2.30 (m, 2H), 1.53-1.62 (m, 11H), 0.86-1.05 (m, 2H), 0.00 (s, 9H). MS (EI/CI) m/z: 484.0 [M+H]·

Step 6

N-tert-Butyl-2-(2-methyl-6,7-dihydro-2H-pyrazolo[4,3-b]pyridin-4(5H)-yl)-5H-pyrrolo[2,3-b]pyrazine-7-carboxamide

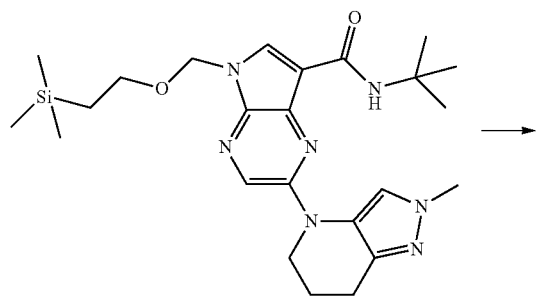

To a stirred solution of N-tert-butyl-2-(2-methyl-6,7-dihydro-2H-pyrazolo[4,3-b]pyridin-4(5H)-yl)-5-((2-(trimethylsilyl)ethoxy)methyl)-5H-pyrrolo[2,3-b]pyrazine-7-carboxamide (87 mg, 180 µmol) in CH$_2$Cl$_2$ (4 mL) was added TFA (740 mg, 500 µL, 6.49 mmol). After 24 h, the mixture was concentrated in vacuo and the residue was re-dissolved in 5 mL of a mixture of (CH$_2$Cl$_2$/methanol/ammonium hydroxide; 60:10:1) and the mixture stirred at room temperature for 24 h, then evaporated to a yellow solid, which was purified by chromatography (spherical silica 20-45 m, 23 g, Versaflash Supelco, 0 to 5% 9:1 methanol:ammonium hydroxide in CH$_2$Cl$_2$, 30 min) to give a residue that was dissolved in CH$_2$Cl$_2$ then precipitated with cyclohexane. The yellow solid was obtained by decanting the mother liquor and dried under high vacuum to give N-tert-butyl-2-(2-methyl-6,7-dihydro-2H-pyrazolo[4,3-b]pyridin-4(5H)-yl)-5H-pyrrolo[2,3-b]pyrazine-7-carboxamide (23 mg, 36%). $^1$H NMR (CHLOROFORM-d) δ: 9.46 (br. s., 1H), 8.08-8.21 (m, 2H), 7.97 (br. s., 1H), 7.82 (s, 1H), 3.88 (m, 5H), 2.89 (t, J=6.2 Hz, 2H), 2.14-2.28 (m, 2H), 1.56 (s, 9H). MS (EI/CI) m/z: 354.1 [M+H]$^+$.

Example 33

N-tert-Butyl-2-(1-methyl-6,7-dihydro-1H-pyrazolo[4,3-b]pyridin-4(5H)-yl)-5H-pyrrolo[2,3-b]pyrazine-7-carboxamide Step 1

1-Methyl-4,5,6,7-tetrahydro-1H-pyrazolo[4,3-b]pyridine

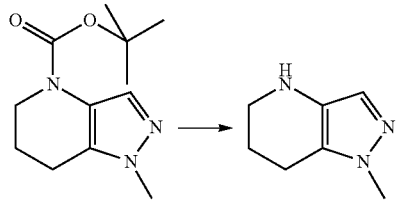

To a stirred solution of tert-butyl 1-methyl-6,7-dihydro-1H-pyrazolo[4,3-b]pyridine-4(5H)-carboxylate (55 mg, 232 µmol) in CH$_2$Cl$_2$ (4 mL) was added TFA (740 mg, 500 µL, 6.49 mmol). After 18 h, the reaction mixture was concentrated in vacuo and the residue obtained purified by chromatography (40 g column, 50 m silica-gel from Analogix, 0 to 5% 9:1 methanol:ammonium hydroxide in CH$_2$Cl$_2$, 20 min) to give 1-methyl-4,5,6,7-tetrahydro-1H-pyrazolo[4,3-b]pyridine (22 mg, 69%). $^1$H NMR (CHLOROFORM-d) δ: 7.05 (s, 1H), 3.70 (s, 3H), 3.08-3.21 (m, 2H), 2.88 (br. s., 1H), 2.64 (t, J=6.4 Hz, 2H), 1.84-2.01 (m, 2H). MS (EI/CI) m/z: 138.2 [M+H]$^+$.

Step 2

N-tert-Butyl-2-(1-methyl-6,7-dihydro-1H-pyrazolo[4,3-b]pyridin-4(5H)-yl)-5-((2-(trimethylsilyl)ethoxy)methyl)-5H-pyrrolo[2,3-b]pyrazine-7-carboxamide

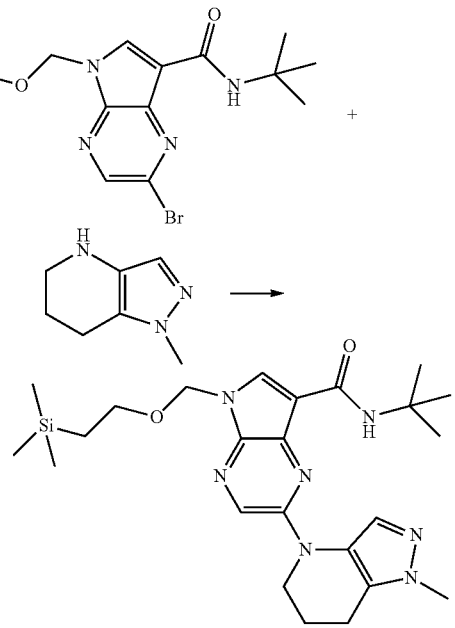

A microwave vial was charged with a mixture of 2-bromo-N-tert-butyl-5-((2-(trimethylsilyl)ethoxy)methyl)-5H-pyrrolo[2,3-b]pyrazine-7-carboxamide (68.5 mg, 160 µmol), 1-methyl-4,5,6,7-tetrahydro-1H-pyrazolo[4,3-b]pyridine (22 mg, 160 µmol), xantphos (27.8 mg, 48.1 µmol), Pd₂(dba)₃ (14.7 mg, 16.0 µmol), Cs₂CO₃ (105 mg, 321 µmol) and dioxane (2 mL). The reaction mixture was purged with argon and then heated to 150° C. for 20 min under microwave irradiation. The mixture was diluted with CH₂Cl₂ and then filtered through a pad of celite. The filtrate was concentrated in vacuo and the residue purified by chromatography (40 g column, 50 µm silica-gel from Analogix, 0 to 5% 9:1 methanol:ammonium hydroxide in CH₂Cl₂, min) to give N-tert-butyl-2-(1-methyl-6,7-dihydro-1H-pyrazolo[4,3-b]pyridin-4(5H)-yl)-5-((2-(trimethylsilyl)ethoxy)methyl)-5H-pyrrolo[2,3-b]pyrazine-7-carboxamide (77 mg, 99%) as a yellow foam. $^1$H NMR (CHLOROFORM-d) δ: 8.29 (s, 1H), 8.14 (s, 1H), 8.10 (s, 1H), 7.88 (s, 1H), 5.63 (s, 2H), 3.93-4.01 (m, 2H), 3.87 (s, 3H), 3.52-3.63 (m, 2H), 2.80-2.91 (m, 2H), 2.16-2.29 (m, 2H), 1.55-1.61 (m, 11H), 0.87-1.02 (m, 2H), 0.00 (s, 9H). MS (EI/CI) m/z: 484.0 [M+H]⁺.

Step 3

N-tert-Butyl-2-(1-methyl-6,7-dihydro-1H-pyrazolo[4,3-b]pyridin-4(5H)-yl)-5H-pyrrolo[2,3-b]pyrazine-7-carboxamide

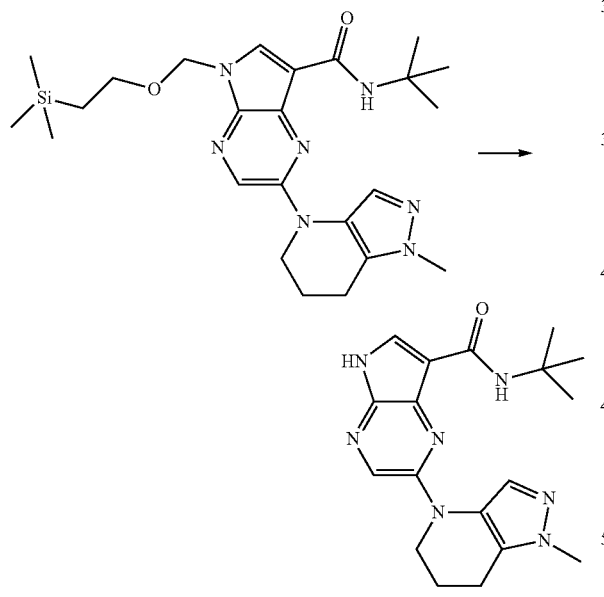

To a stirred solution of N-tert-butyl-2-(1-methyl-6,7-dihydro-1H-pyrazolo[4,3-b]pyridin-4(5H)-yl)-5-((2-(trimethylsilyl)ethoxy)methyl)-5H-pyrrolo[2,3-b]pyrazine-7-carboxamide (77 mg, 159 µmol) in CH₂Cl₂ (4 mL) was added TFA (740 mg, 500 µL, 6.49 mmol). After 24 h the solvents were evaporated and the residue was re-dissolved in 5 mL of a mixture of (CH₂Cl₂/methanol/ammonium hydroxide; 60:10:1). After stirring at room temperature for 24 h, the mixture was concentrated in vacuo to a yellow solid, which was purified by chromatography (spherical silica 20-45 µm, 23 g, Versaflash Supelco, 0 to 5% 9:1 methanol:ammonium hydroxide in CH₂Cl₂, 30 min) to give a product that was dissolved in CH₂Cl₂ and precipitated by addition of cyclohexane. The yellow solid formed was separated by decantation of the mother liquor and then dried under high vacuum to give N-tert-butyl-2-(1-methyl-6,7-dihydro-1H-pyrazolo[4,3-b]pyridin-4(5H)-yl)-5H-pyrrolo[2,3-b]pyrazine-7-carboxamide (33 mg, 59%) as a yellow solid. $^1$H NMR (CHLOROFORM-d) δ: 8.95 (br. s., 1H), 8.24 (s, 1H), 8.02-8.14 (m, 2H), 7.85 (s, 1H), 3.88-3.99 (m, 2H), 3.83 (s, 3H), 2.81 (t, J=6.6 Hz, 2H), 2.08-2.24 (m, 2H), 1.55 (s, 9H). MS (EI/CI) m/z: 354.1 [M+H]⁺.

Example 34

3-Methyl-2-(1-methyl-1H-pyrazol-4-ylamino)-5H-pyrrolo[2,3-b]pyrazine-7-carboxylic acid tert-butylamide Step 1

3,5-Dibromo-6-methyl-pyrazin-2-ylamine

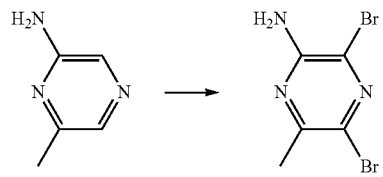

3,5-Dibromo-6-methyl-pyrazin-2-ylamine was prepared by the bromination of 6-methyl-pyrazin-2-ylamine, according to the method described by Sato (Sato, N., J. Het. Chem., 1980, 17, 143-147). $^1$H NMR (400 MHz, DMSO-d₆) δ ppm 2.34 (s, 3H), 6.86 (br s, 2H, —NH₂); MS (EI/CI) m/z: 266 [M+H].

Step 2

5-Bromo-6-methyl-3-trimethylsilanylethynyl-pyrazin-2-ylamine

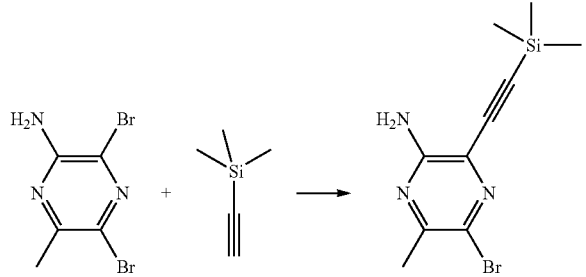

A solution of trimethylsilylacetylene (1.03 g, 29.4 mmol) in tetrahydrofuran (2 mL) was added dropwise to a cooled (water bath at ca. 15° C.) mixture of 3,5-dibromo-6-methyl-pyrazin-2-ylamine (7.48 g, 28 mmol), copper (I) iodide (1.07 g, 5.6 mmol), bis-triphenylphosphine palladium dichloride (1.97 g, 2.3 mmol), triethylamine (3.542 g, 35 mmol) and tetrahydrofuran (75 mL). The mixture was stirred under an atmosphere of argon, for 16 hours, during which time the reaction was allowed to warm to ambient temperature. The reaction mixture was poured onto water and extracted with hexanes-ethyl acetate (2:1). The organic layer was washed successively with saturated ammonium chloride solution, water, and then again with saturated ammonium chloride solution, water, then dried over anhydrous magnesium sulfate, treated with activated charcoal, filtered through celite and concentrated under reduced pressure. Purification by chromatography (silica, 20% ethyl acetate in hexanes) gave (6.19 g, 77%) of 5-bromo-6-methyl-3-trimethylsilanylethynyl-pyrazin-2-ylamine as an off white solid. $^1$H NMR (400 MHz, DMSO-d$_6$) δ ppm 0.26 (s, 9H), 2.39 (s, 3H), 6.71 (br s, 2H, —NH$_2$).

Step 3

2-Bromo-3-methyl-5H-pyrrolo[2,3-b]pyrazine

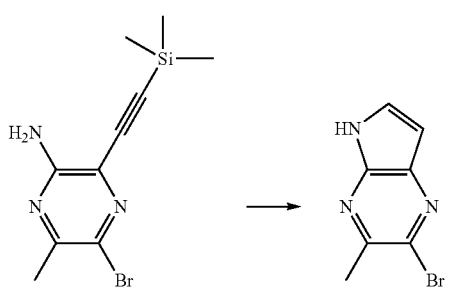

A solution of 5-bromo-6-methyl-3-trimethylsilanylethynyl-pyrazin-2-ylamine (6.19 g, 21.8 mmol) in tetrahydrofuran (15 mL) was added, dropwise under an argon atmosphere, to a solution of tetrahydrofuran (24 mL) and 1 M potassium t-butoxide in tetrahydrofuran (24 mL, 24 mmol) which was cooled in a bath at –30° C. The mixture was stirred for 1 h, the cooling bath was removed and the mixture stirred at room temperature. After 19 h the mixture was cooled in an ice bath and quenched by the addition of 0.5 M hydrochloric acid (48 mL). The mixture was then poured into water and extracted twice with ethyl acetate. The combined ethyl acetate layers were washed with water, dried over anhydrous magnesium sulfate, treated with activated charcoal, filtered through celite and concentrated under reduced pressure to give an orange solid (3.83 g) which was mostly 2-bromo-3-methyl-5H-pyrrolo[2,3-b]pyrazine along with a small amount of desilylated starting material. This material was used in the next step without further purification. NMR data was obtained from material prepared in a separate reaction and purified by chromatography (silica, hexanes-ethyl acetate 70:30). $^1$H NMR (400 MHz, DMSO-d$_6$) δ ppm 2.64 (s, 3H), 6.57 (d, d, J=1.5, 3.3 Hz, 1H), 7.84 (t, J=3.3 Hz, 1H), 12.12 (br s, 1H, NH) MS (EI/CI) m/z: 212 [M+H].

Step 4

2-Bromo-3-methyl-5-(2-trimethylsilanyl-ethoxymethyl)-5H-pyrrolo[2,3-b]pyrazine

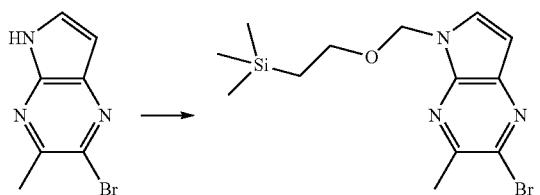 [SMILES: Cc1nc2[nH]ccc2nc1Br ; Cc1nc2c(ccn2COCC[Si](C)(C)C)nc1Br]

To a mixture of the crude 2-bromo-3-methyl-5H-pyrrolo[2,3-b]pyrazine (3.83 g, 18 mmol) prepared above and N,N-dimethylformamide (25 mL), under an atmosphere of argon and cooled in an ice bath, was added 95% sodium hydride oil dispersion (0.912 g, 36 mmol) (gas evolution). The mixture was stirred for 15 minutes, and then (2-chloromethoxy-ethyl)-trimethylsilane (3.61 g, 22 mmol) in N,N-dimethylformamide (3 mL) was added dropwise. After 10 minutes, the cooling bath was removed and the mixture stirred for another 3½ hours at room temperature. The mixture was cooled in an ice bath, quenched by the addition of water, and then poured into water and extracted three times with ether. The combined ether extracts were washed twice with water, dried over anhydrous magnesium sulfate, filtered and concentrated under reduced pressure. Purification by chromatography (silica, 15% ethyl acetate in hexanes) gave 2-bromo-3-methyl-5-(2-trimethylsilanyl-ethoxymethyl)-5H-pyrrolo[2,3-b]pyrazine (3.47 g, 56%) as an amber solid. $^1$H NMR (400 MHz, DMSO-d$_6$) δ ppm –0.11 (s, 9H), 0.82 (m, 2H), 2.67 (s, 3H), 3.51 (m, 2H), 5.59 (s, 2H), 6.67 (d, J=3.5 Hz, 1H), 8.01 (d, J=3.5 Hz, 1H).

Step 5

2-Bromo-3-methyl-5-(2-trimethylsilanyl-ethoxymethyl)-5H-pyrrolo[2,3-b]pyrazine-7-carbaldehyde

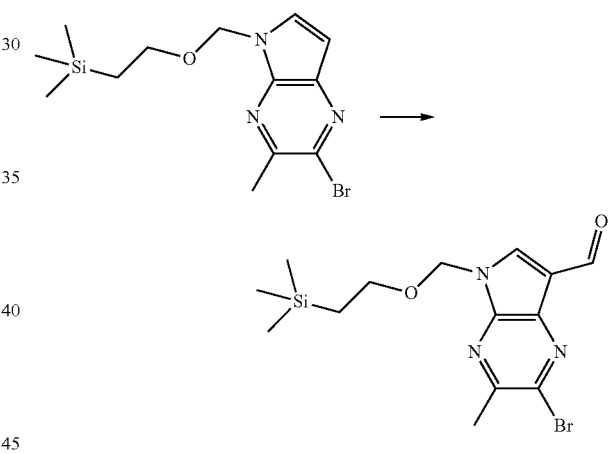

Trifluoroacetic anhydride (10.2 mL, 60.8 mmol) was added dropwise, with cooling (ice bath), to N,N-dimethylformamide (24 mL) under an argon atmosphere. The cooling bath was removed for 15 min to facilitate stirring and then replaced. A solution of 2-bromo-3-methyl-5-(2-trimethylsilanyl-ethoxymethyl)-5H-pyrrolo[2,3-b]pyrazine (3.47 g, 10.1 mmol) in dichloromethane (5 mL) was added dropwise. The cooling bath was removed; the mixture was stirred for 15 min, then set in a bath at 45° C. and stirred for 16 h. The mixture was cooled, then poured onto ice water (200 mL) containing sodium carbonate (13 g) and extracted four times with ether. The combined ether extracts were washed twice with water, dried over anhydrous magnesium sulfate, filtered and concentrated under reduced pressure. Purification by chromatography on (silica, 20% ethyl acetate in hexanes) gave 2-bromo-3-methyl-5-(2-trimethylsilanyl-ethoxymethyl)-5H-pyrrolo[2,3-b]pyrazine-7-carbaldehyde (3.17 g, 84%) as a light yellow solid. $^1$H NMR (400 MHz, DMSO-d$_6$) δ ppm –0.09 (s, 9H), 0.85 (t, J=8.0 Hz, 2H), 2.71 (s, 3H), 3.58 (t, J=8.0 Hz, 2H), 5.68 (s, 2H), 8.87 (s, 1H), 10.04 (s, 1H).

Step 6

2-Bromo-3-methyl-5-(2-trimethylsilanyl-ethoxymethyl)-5H-pyrrolo[2,3-b]pyrazine-7-carboxylic acid

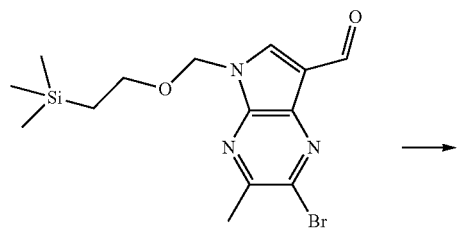

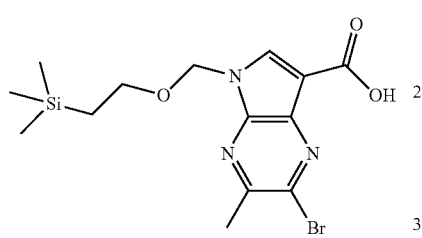

To a stirred mixture of 2-bromo-3-methyl-5-(2-trimethylsilanyl-ethoxymethyl)-5H-pyrrolo[2,3-b]pyrazine-7-carbaldehyde (3.17 g, 8.55 mmol), tert-butanol (10 mL), tetrahydrofuran (10 mL), and water (10 mL) was added sulfamic acid (3.32 g, 34 mmol) and then a solution of potassium dihydrogen phosphate (8.85 g, 65 mmol) and sodium chlorite (1.93 g, 21 mmol) in water (42 mL). After 1 h the mixture was diluted with ethyl acetate, washed once with brine, dried over anhydrous magnesium sulfate, filtered and concentrated under reduced pressure to give 2-bromo-3-methyl-5-(2-trimethylsilanyl-ethoxymethyl)-5H-pyrrolo[2,3-b]pyrazine-7-carboxylic acid (3.02 g, 91%) as a light yellow solid. This material was used in the next step without further purification. $^1$H NMR (400 MHz, DMSO-d$_6$) δ ppm −0.10 (s, 9H), 0.83 (t, J=8.0 Hz, 2H), 2.69 (s, 3H), 3.55 (t, J=8.0 Hz, 2H), 5.64 (s, 2H), 8.64 (s, 1H), 12.46 (br s, J=9.06 Hz, 1H, —COOH).

Step 7

2-Bromo-3-methyl-5-(2-trimethylsilanyl-ethoxymethyl)-5H-pyrrolo[2,3-b]pyrazine-7-carboxylic acid tert-butylamide

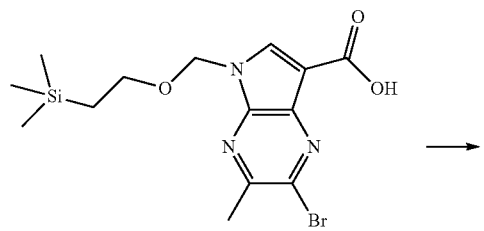

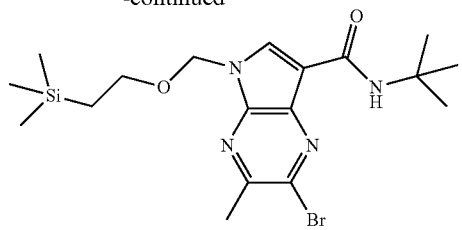

A mixture of 2-bromo-3-methyl-5-(2-trimethylsilanyl-ethoxymethyl)-5H-pyrrolo[2,3-b]pyrazine-7-carboxylic acid (1.16 g, 3 mmol), HBTU [1-[bis(dimethylamino)methylene]-1H-benzotriazolium 3-oxide, hexafluorophosphate (1-) (1:1) (1.48 g, 3.9 mmol), N,N-dimethylformamide (12 mL) and triethylamine (0.61 g, 6 mmol) was stirred at room temperature for 1 h, and then tert-butylamine (0.63 mL, 6 mmol) was added. The mixture was stirred an additional hour and then diluted with ethyl acetate, washed once with 0.5 M sodium carbonate, twice with water, once with brine, dried over anhydrous sodium sulfate, filtered and concentrated under reduced pressure. Purification by chromatography (silica, 20% ethyl acetate in hexanes) gave 2-bromo-3-methyl-5-(2-trimethylsilanyl-ethoxymethyl)-5H-pyrrolo[2,3-b]pyrazine-7-carboxylic acid tert-butylamide (1.22 g, 92%) as a white crystalline solid. $^1$H NMR (400 MHz, DMSO-d$_6$) δ ppm −0.09 (s, 9H), 0.83 (t, J=8.2 Hz, 2H), 1.43 (s, 9H), 2.71 (s, 3H), 3.54 (t, J=8.2 Hz, 2H), 5.64 (s, 2H), 7.64 (s, 1H), 8.49 (s, 1H).

MS (EI/CI) m/z: 441 [M+H]

Step 8

3-Methyl-2-(1-methyl-1H-pyrazol-4-ylamino)-5-(2-trimethylsilanyl-ethoxymethyl)-5H-pyrrolo[2,3-b]pyrazine-7-carboxylic acid tert-butylamide

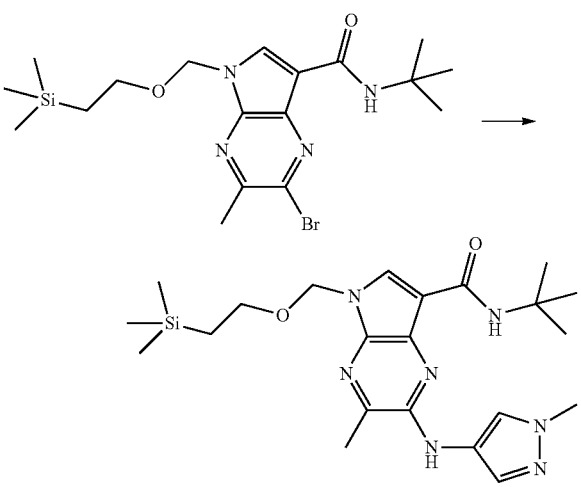

A mixture of 2-bromo-3-methyl-5-(2-trimethylsilanyl-ethoxymethyl)-5H-pyrrolo[2,3-b]pyrazine-7-carboxylic acid tert-butylamide (0.110 g, 0.25 mmol), 1-methyl-1H-pyrazol-4-ylamine 1.35-HCl salt (0.073 g, 0.5 mmol), tris(dibenzylideneacetone)dipalladium (0.011 g, 0.0125 mmol), racemic BINAP [rac-2,2'-bis(diphenylphosphino)-1,1'-binaphthyl](0.023 g, 0.038 mmol) and sodium tert-butoxide (0.094 g, 0.98 mmol) in toluene (2½ mL), under an argon atmosphere, was heated and stirred in a sealed vessel at 110° C. for 18.5 h. The cooled reaction mixture was diluted with ethyl acetate, washed once with brine, dried over anhydrous sodium sulfate, filtered and concentrated under reduced pressure. Purification by chromatography (silica, 70% ethyl acetate in hexanes) gave 0.104 g of slightly impure 3-methyl-2-(1-methyl-1H-pyrazol-4-ylamino)-5-(2-trimethylsilanyl-ethoxymethyl)-5H-pyrrolo[2,3-b]pyrazine-7-carboxylic acid tert-butylamide as a yellow-brown solid. This material was combined with 0.022 g of partially purified product obtained from a separate, lower yielding, coupling reaction (palladium acetate was used in place of tris(dibenzylideneacetone)dipalladium), and purified by chromatography (silica, ethyl acetate) to give 3-methyl-2-(1-methyl-1H-pyrazol-4-ylamino)-5-(2-trimethylsilanyl-ethoxymethyl)-5H-pyrrolo[2,3-b]pyrazine-7-carboxylic acid tert-butylamide (0.112 g) as a light yellow solid. $^1$H NMR (400 MHz, DMSO-$d_6$) δ ppm −0.08 (s, 9H), 0.83 (t, J=8.2 Hz, 2H), 1.38 (s, 9H), 2.54 (s, 3H), 3.51 (t, J=8.2 Hz, 2H), 3.80 (s, 3H), 5.55 (s, 2H), 7.61 (s, 1H), 7.68 (s, 1H), 7.85 (s, 1H), 8.01 (s, 1H), 8.19 (s, 1H); MS (EI/CI) m/z: 458 [M+H].

Step 9

3-Methyl-2-(1-methyl-1H-pyrazol-4-ylamino)-5H-pyrrolo[2,3-b]pyrazine-7-carboxylic acid tert-butylamide

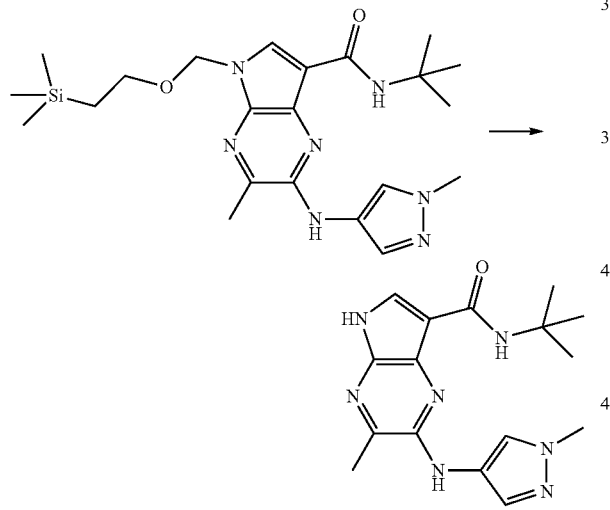

A mixture of 3-methyl-2-(1-methyl-1H-pyrazol-4-ylamino)-5-(2-trimethylsilanyl-ethoxymethyl)-5H-pyrrolo[2,3-b]pyrazine-7-carboxylic acid tert-butylamide (0.110 g, 0.24 mmol), dichloromethane (2.5 mL) and trifluoroacetic acid (0.5 mL) was left to stand at room temperature of 13 h and then concentrated under reduced pressure. The yellow residue was stirred with dichloromethane-methanol-ammonium hydroxide (50:10:1, 10 mL) for 1½ h and then concentrated under reduced pressure. The residue was taken up in ethyl acetate and washed successively with 0.5 M sodium carbonate, water and then brine. The ethyl acetate layer was dried over anhydrous sodium sulfate, filtered and concentrated under reduced pressure to give 0.082 g of a light yellow solid. By nmr, the conversion was incomplete, so the mixture was stirred another 2 hours with dichloromethane-methanol-ammonium hydroxide (5:5:1) for 1.5 hours and then diluted with ethyl acetate and washed once with water and once with brine. The ethyl acetate layer was dried over anhydrous sodium sulfate, filtered and concentrated under reduced pressure to give 0.075 g of a light yellow solid. Recrystallization from acetonitrile-methanol gave 3-methyl-2-(1-methyl-1H-pyrazol-4-ylamino)-5H-pyrrolo[2,3-b]pyrazine-7-carboxylic acid tert-butylamide (0.047 g, 41%) as a light yellow crystalline solid. $^1$H NMR (400 MHz, DMSO-$d_6$) δ ppm 1.38 (s, 9H), 2.52 (s, 3H), 3.80 (s, 3H), 7.60 (s, 1H), 7.68 (s, 1H), 7.79 (s, 1H), 7.84 (s, 1H), 8.07 (s, 1H, —NH), 11.97 (br s, 1H, —NH). MS (EI/CI) m/z: 328 [M+H].

Example 35

2-(3-Methanesulfonyl-phenylamino)-3-methyl-5H-pyrrolo[2,3-b]pyrazine-7-carboxylic acid tert-butylamide Step 1

2-(3-Methanesulfonyl-phenylamino)-3-methyl-5-(2-trimethylsilanyl-ethoxymethyl)-5H-pyrrolo[2,3-b]pyrazine-7-carboxylic acid tert-butylamide

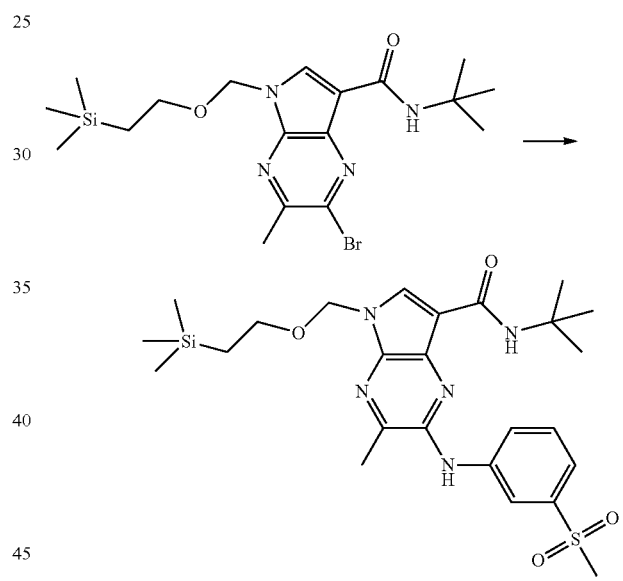

A mixture of 2-bromo-3-methyl-5-(2-trimethylsilanyl-ethoxymethyl)-5H-pyrrolo[2,3-b]pyrazine-7-carboxylic acid tert-butylamide (0.110 g, 0.25 mmol), 3-methanesulfonyl-phenylamine (0.086 g, 0.5 mmol), tris(dibenzylideneacetone)dipalladium (0.011 g, 0.0125 mmol), racemic BINAP [rac-2,2'-bis(diphenylphosphino)-1,1'-binaphthyl](0.023 g, 0.038 mmol) and sodium tert-butoxide (0.060 g, 0.63 mmol) in toluene (2.5 mL), under an argon atmosphere, was heated and stirred in a sealed vessel at 110° C. for 21.5 h. The cooled reaction mixture was diluted with ethyl acetate, washed once with brine, dried over anhydrous sodium sulfate, filtered and concentrated under reduced pressure. Purification by chromatography (silica, 75% ethyl acetate in hexanes) gave 0.107 g of slightly impure 2-(3-methanesulfonyl-phenylamino)-3-methyl-5-(2-trimethylsilanyl-ethoxymethyl)-5H-pyrrolo[2,3-b]pyrazine-7-carboxylic acid tert-butylamide as a yellow glass. The reaction was repeated as above, and the combined slightly impure products were purified further by chromatography (silica, 33% ethyl acetate in hexanes) to give 2-(3-methanesulfonyl-phenylamino)-3-methyl-5-(2-trimethylsilanyl-ethoxymethyl)-5H-pyrrolo[2,3-b]pyrazine-7-carboxylic acid tert-butylamide (0.169 g, 64%) as a light yellow solid. ¹H NMR (400 MHz, DMSO-d₆) δ ppm −0.07 (s, 9H), 0.85 (t, J=8.2 Hz, 2H), 1.30 (s, 9H), 2.64 (s, 3H), 3.19 (s, 3H), 3.54 (t, J=8.2 Hz, 2H), 5.59 (s, 2H), 7.49 (m, 1H), 7.56 (m, 1H), 7.62 (s, 1H), 7.96 (m, 1H), 8.05 (m, 1H), 8.16 (s, 1H), 8.74 (s, 1H). MS (EI/CI) m/z: 532 [M+H].

Step 2

2-(3-Methanesulfonyl-phenylamino)-3-methyl-5H-pyrrolo[2,3-b]pyrazine-7-carboxylic acid tert-butylamide

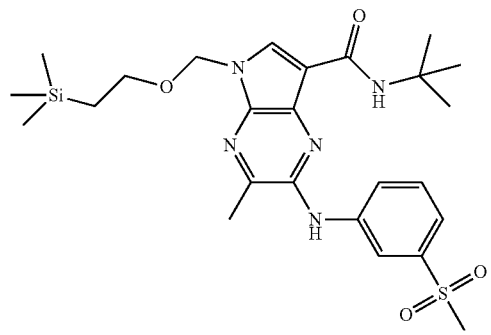

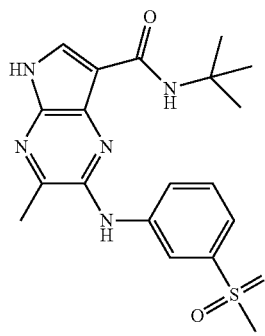

A mixture of 2-(3-methanesulfonyl-phenylamino)-3-methyl-5-(2-trimethylsilanyl-ethoxymethyl)-5H-pyrrolo[2,3-b]pyrazine-7-carboxylic acid tert-butylamide (0.167 g, 0.31 mmol), dichloromethane (2.5 mL) and trifluoroacetic acid (0.5 mL) was left at room temperature for 14 h and then concentrated under reduced pressure. The yellow residue was stirred with dichloromethane-methanol-ammonium hydroxide (3:3:1, 7 mL) for 3 h. The reaction mixture was then diluted with ethyl acetate, washed once with brine, dried over anhydrous sodium sulfate and concentrated under reduced pressure, to give 0.126 g of a light yellow solid. The product was recrystallized from acetonitrile-methanol to give 2-(3-methanesulfonyl-phenylamino)-3-methyl-5H-pyrrolo[2,3-b]pyrazine-7-carboxylic acid tert-butylamide (0.063 g, 50%) as a light yellow crystalline solid. ¹H NMR (400 MHz, DMSO-d₆) δ ppm 1.30 (s, 9H), 2.61 (s, 3H), 3.19 (s, 3H), 7.46 (m, 1H), 7.54 (m, 1H), 7.64 (s, 1H), 7.94 (m, 1H), 7.96 (s, 1H), 8.04 (m, 1H), 8.66 (s, 1H), 12.21 (br s, 1H). MS (EI/CI) m/z: 402 [M+H].

Example 36

3-Methyl-2-(3-methyl-isothiazol-5-ylamino)-5H-pyrrolo[2,3-b]pyrazine-7-carboxylic acid tert-butylamide Step 1

3-Methyl-2-(3-methyl-isothiazol-5-ylamino)-5-(2-trimethylsilanyl-ethoxymethyl)-5H-pyrrolo[2,3-b]pyrazine-7-carboxylic acid tert-butylamide

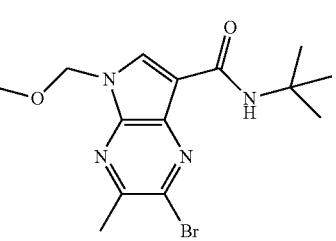

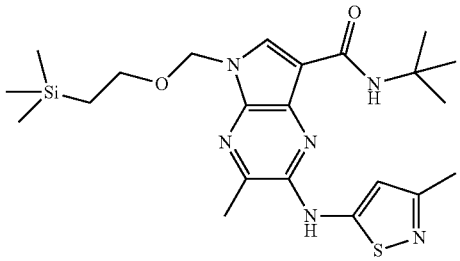

A mixture of 2-bromo-3-methyl-5-(2-trimethylsilanyl-ethoxymethyl)-5H-pyrrolo[2,3-b]pyrazine-7-carboxylic acid tert-butylamide (0.221 g, 0.5 mmol), 3-methyl-isothiazol-5-ylamine hydrochloride (0.151 g, 1 mmol), tris(dibenzylideneacetone)dipalladium (0.023 g, 0.025 mmol), racemic BINAP [rac-2,2'-bis(diphenylphosphino)-1,1'-binaphthyl] (0.047 g, 0.075 mmol) and sodium tert-butoxide (0.144 g, 1.5 mmol) in toluene (3.5 mL), under an argon atmosphere, was heated and stirred in a sealed vessel at 110° C. for 19 h. The cooled reaction mixture was diluted with ethyl acetate, washed once with brine, dried over anhydrous sodium sulfate, filtered and concentrated under reduced pressure. Purification by chromatography (silica, 75% ethyl acetate in hexanes, then repeated with 50% ethyl acetate in hexanes, and again with 40% ethyl acetate I hexanes) gave 3-methyl-2-(3-methyl-isothiazol-5-ylamino)-5-(2-trimethylsilanyl-ethoxymethyl)-5H-pyrrolo[2,3-b]pyrazine-7-carboxylic acid tert-butylamide (0.101 g, 43%) as a yellow solid. ¹H NMR (400 MHz, DMSO-d₆) δ ppm −0.08 (s, 9H), 0.84 (t, J=8.0 Hz, 2H), 1.55 (s, 9H), 2.35 (s, 3H), 2.67 (s, 3H), 3.53 (t, J=8.0 Hz, 2H), 5.61 (s, 2H), 6.94 (s, 1H), 7.34 (s, 1H), 8.25 (s, 1H), 10.49 (s, 1H). MS (EI/CI) m/z: 475 [M+H].

Step 2

3-Methyl-2-(3-methyl-isothiazol-5-ylamino)-5H-pyrrolo[2,3-b]pyrazine-7-carboxylic acid tert-butylamide

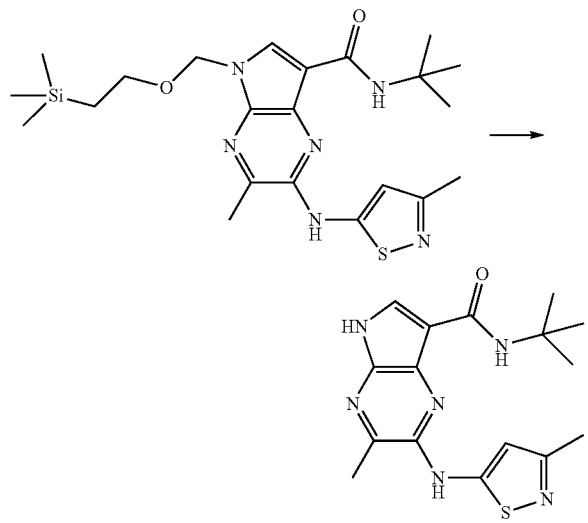

A mixture of 3-methyl-2-(3-methyl-isothiazol-5-ylamino)-5-(2-trimethylsilanyl-ethoxymethyl)-5H-pyrrolo[2,3-b]pyrazine-7-carboxylic acid tert-butylamide (0.099 g, 0.21 mmol), dichloromethane (2.5 mL) and trifluoroacetic acid (0.5 mL) was left at room temperature for 14 h and then concentrated under reduced pressure. The yellow residue was stirred with dichloromethane-methanol-ammonium hydroxide (3:3:1, 7 mL) for 3 h. The reaction mixture was then diluted with ethyl acetate, washed once with brine, dried over anhydrous sodium sulfate and concentrated under reduced pressure to give 0.079 g of a light yellow solid. The product was recrystallized from acetonitrile-methanol to give 3-methyl-2-(3-methyl-isothiazol-5-ylamino)-5H-pyrrolo[2,3-b]pyrazine-7-carboxylic acid tert-butylamide (0.046 g, 64%) as a light yellow crystalline solid. $^1$H NMR (400 MHz, DMSO-$d_6$) δ ppm 1.55 (s, 9H), 2.34 (s, 3H), 2.65 (s, 3H), 6.92 (s, 1H), 7.32 (s, 1H), 8.04 (d, J=1.5 Hz, 1H), 10.41 (s, 1H), 12.36 (s, 1H). MS (EI/CI) m/z: 345 [M+H].

Example 37

2-Phenylamino(D5)-5H-pyrrolo[2,3-b]pyrazine-7-carboxylic acid tert-butylamide

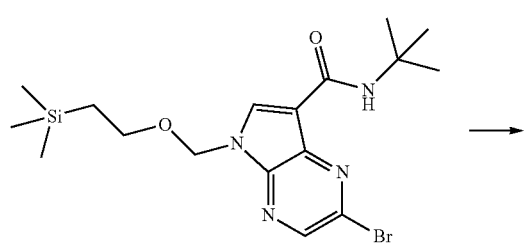

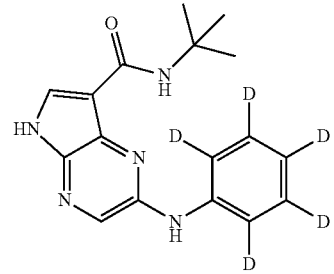

Step 1

A mixture of 2-bromo-N-tert-butyl-5-((2-(trimethylsilyl)ethoxy)methyl)-5H-pyrrolo[2,3-b]pyrazine-7-carboxamide (125 mg, 292 mol), aniline-D5 (43.1 mg, 439 mol), xantphos (50.8 mg, 87.7 mol), Pd$_2$(dba)$_3$ (26.8 mg, 29.2 mol) and cesium carbonate (191 mg, 585 mol) in dioxane (2 mL) was heated in a microwave at 150° C. for 20 min. The reaction mixture was filtered through a pad of celite then the filtrate was concentrated in vacuo and purified by chromatography (silica, 20-60% ethyl acetate in hexanes) to give 2-phenylamino(D5)-5-(2-trimethylsilanyl-ethoxymethyl)-5H-pyrrolo[2,3-b]pyrazine-7-carboxylic acid tert-butylamide (40 mg, 90.0 mol, 31%) as a light yellow solid. $^1$H NMR (400 MHz, CDCl$_3$-d) δ ppm: 8.15 (s, 1H), 7.99 (s, 1H), 7.93 (s, 1H), 6.70 (s, 1H), 5.63 (s, 2H), 3.57 (t, J=8.2, 2 H), 1.57 (s, 9H), 0.96 (t, J=8.1, 2 H), 0.01 (s, 9H).

Step 2

To a solution of 2-phenylamino(D5)-5-(2-trimethylsilanyl-ethoxymethyl)-5H-pyrrolo[2,3-b]pyrazine-7-carboxylic acid tert-butylamide (40 mg, 90.0 mol) in dichloromethane (1.5 mL) was added trifluoroacetic acid (205 mg, 139 µL, 1.8 mmol) and the mixture stirred at room temperature for 16 h. The mixture was concentrated then re-dissolved in dichloromethane (1.5 mL), methanol (0.75 mL) and ammonium hydroxide (0.2 mL) and the mixture stirred at room temperature for 1 h. The mixture was concentrated in vacuo then triturated with water and filtered. The solid obtained was washed with ether then dried to give 2-phenylamino(D5)-5H-pyrrolo[2,3-b]pyrazine-7-carboxylic acid tert-butylamide (24 mg, 76.3 mol, 85%) as a yellow solid. $^1$H NMR (400 MHz, DMSO-d) δ ppm: 12.31 (s, 1H), 9.47 (s, 1H), 8.00 (s, 1H), 7.99 (s, 1H), 7.76 (s, 1H), 1.44 (s, 9H); MS (EI/CI) m/z: 315.1 [M+H].

Example 38

N-tert-Butyl-3-chloro-2-(3-methylisothiazol-5-ylamino)-5H-pyrrolo[2,3-b]pyrazine-7-carboxamide
2-Bromo-N-tert-butyl-3-chloro-5-((2-(trimethylsilyl)ethoxy)methyl)-5H-pyrrolo[2,3-b]pyrazine-7-carboxamide

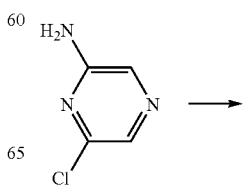

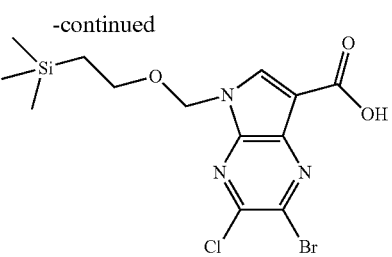

Step 1

3,5-Dibromo-6-chloro-pyrazin-2-ylamine

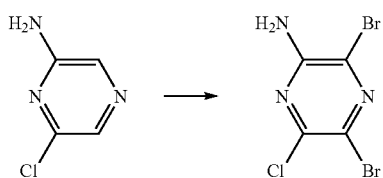

To a solution of 6-chloro-pyrazin-2-ylamine (5.0 g, 38.8 mmol) in chloroform (194 mL) was added N-bromosuccinimide (20.7 g, 116 mmol) under a nitrogen atmosphere and the reaction mixture was stirred at room temperature for 5 h. The resulting mixture was poured into an aqueous solution of $K_2CO_3$ (300 mL) and extracted with dichloromethane (200 mL×4). The combined organic extracts were dried and purified by chromatography (silica, 10-20% ethyl acetate in hexanes) to give 3,5-dibromo-6-chloro-pyrazin-2-ylamine (4.2 g, 38%) as a yellow solid. LC-MS: 286.0 (M−H).

Step 2

5-Bromo-6-chloro-3-trimethylsilanylethynyl-pyrazin-2-ylamine

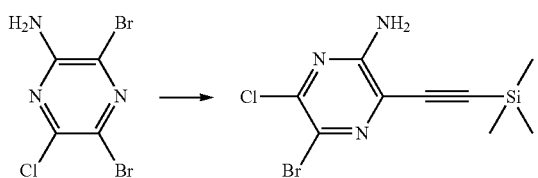

To a stirred solution of 3,5-dibromo-6-chloro-pyrazin-2-ylamine (5.0 g, 17.42 mmol) in anhydrous THF (40 mL) was added triethylamine (3.52 g, 34.84 mmol) and CuI (0.333 g, 1.74 mmol). The mixture was degassed with bubbling argon for 10 min then evacuated and back-filled with argon. It was purged thoroughly with argon for 20 min and $Pd(PPh_3)_2Cl_2$ (0.355 g, 0.52 mmol) was added. The reaction mixture was cooled to −5° C., TMS-acetylene (1.90 g, 19.16 mmol) was added very slowly and the temperature was slowly increased to 15° C. during 3 h. The reaction mixture was diluted with water (30 mL) and extracted with ethyl acetate (100 mL×3). The combined organic layers were concentrated in vacuo then purified by chromatography (silica, 5% ethyl acetate in hexanes) to give 5-bromo-6-chloro-3-trimethylsilanylethynyl-pyrazin-2-ylamine (4.0 g, 75%) as a yellow solid. LC-MS: 304.0 (M+H).

Step 3

2-Bromo-3-chloro-5H-pyrrolo[2,3-b]pyrazine

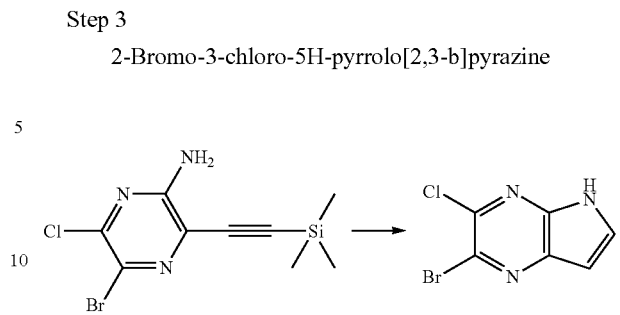

To a stirred solution of 5-bromo-6-chloro-3-trimethylsilanylethynyl-pyrazin-2-ylamine (2.0 g, 6.58 mmol) in THF (28 mL) was added a 1 M solution of KOtBu in THF (7.24 mL, 7.24 mmol) slowly at 0° C. under a nitrogen atmosphere. The reaction mixture was stirred at 0° C. for 10 min and then warmed to room temperature. After 2 h, the mixture was concentrated in vacuo and the residue obtained was suspended in water (7.5 mL) and saturated aqueous $NaHCO_3$ (7.5 mL) and stirred overnight at room temperature The solid was filtered, washed with water and hexanes then dried in an oven at 80° C. to give 2-bromo-3-chloro-5H-pyrrolo[2,3-b]pyrazine (1.64 g) as brown solid. LC-MS: 232 (M−H). This was used directly without further purification.

Step 4

2-Bromo-3-chloro-pyrrolo[2,3-b]pyrazine-5-carboxylic acid tert-butyl ester

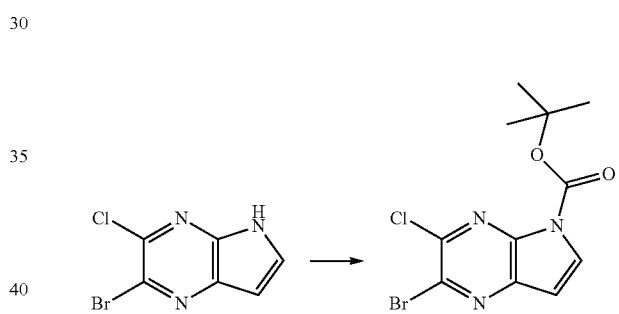

To a stirred suspension of 2-bromo-3-chloro-5H-pyrrolo[2,3-b]pyrazine (1.52 g, 6.55 mmol) in acetonitrile (25 mL) was added DMAP (0.008 g, 0.07 mmol). After 5 min, di-tert-butyl dicarbonate (1.82 mL, 8.52 mmol) was added and the mixture stirred at room temperature for 2 h. The reaction mixture was concentrated in vacuo and the residue obtained then purified by chromatography (silica, 7% ethyl acetate in hexanes) to give 2-bromo-3-chloro-pyrrolo[2,3-b]pyrazine-5-carboxylic acid tert-butyl ester (1.0 g, 46% over two steps) as a yellow solid. LC-MS: 334.2 (M+H).

Step 5

(2-Bromo-3-chloro-7-hydroxymethyl-pyrrolo[2,3-b]pyrazin-5-yl)-methanol

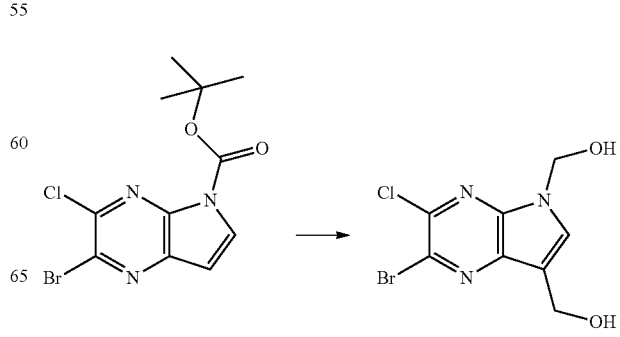

To a stirred solution of 2-bromo-3-chloro-pyrrolo[2,3-b]pyrazine-5-carboxylic acid tert-butyl ester (6.0 g, 18.0 mmol) in 1,4-dioxane (100 mL) was added methanal (5.4 g, 180.4 mmol) and 1 M NaOH solution (54 mL) and the reaction mixture was stirred at room temperature for 16 h. 1.2 N HCl was added into the reaction mixture until the mixture reached pH 7. The reaction mixture was concentrated in vacuo and the residue obtained was diluted with water (50 mL) and extracted with ethyl acetate (150 mL×3). The organic layers were combined and concentrated in vacuo to give (2-bromo-3-chloro-7-hydroxymethyl-pyrrolo[2,3-b]pyrazin-5-yl)-methanol (4.4 g, 83%) as yellow solid. LC-MS: 292.2 (M–H). This was used directly without further purification.

Step 6

2-Bromo-3-chloro-5H-pyrrolo[2,3-b]pyrazine-7-carbaldehyde

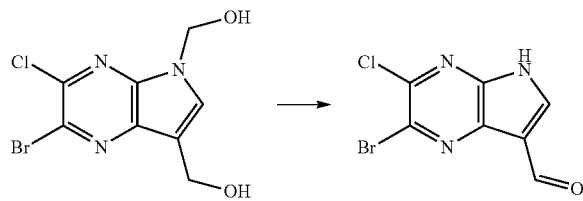 [SMILES: OCc1cn(CO)c2nc(Cl)c(Br)nc12 ; O=Cc1c[nH]c2nc(Cl)c(Br)nc12]

To a stirred suspension of (2-bromo-3-chloro-7-hydroxymethyl-pyrrolo[2,3-b]pyrazin-5-yl)-methanol (2.0 g, 6.84 mmol) in acetone (67 mL) was added Jone's reagent (2.12 mL) and the mixture stirred at room temperature for 20 min. The mixture was cooled then filtered through a pad of celite and the filtrate was concentrated in vacuo. The residue was diluted with THF (35 mL) and 1 N NaOH solution (18 mL). The resulting mixture was stirred at room temperature for 16 h, then concentrated in vacuo to ~20 mL and adjusted to pH7 by addition of 1N HCl. The mixture was extracted with ethyl acetate (100 mL×3), dried and concentrated to give 2-bromo-3-chloro-5H-pyrrolo[2,3-b]pyrazine-7-carbaldehyde (1.4 g, 80%) as a brown solid. LC-MS: 260.2 (M–H). This was used directly without further purification.

Note: Preparation of Jone's reagent: A solution of $CrO_3$ (13.66 g) in water (20 mL) was cooled to 0° C. and conc.$H_2SO_4$ (11.5 mL) was slowly added. The volume of the resulting solution was made up to 50 mL with the addition of water to obtain the Jone's reagent.

Step 7

2-Bromo-3-chloro-5-(2-trimethylsilanyl-ethoxymethyl)-5-pyrrolo[2,3-b]pyrazine-7-carbaldehyde

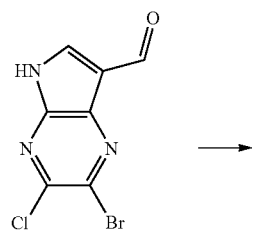

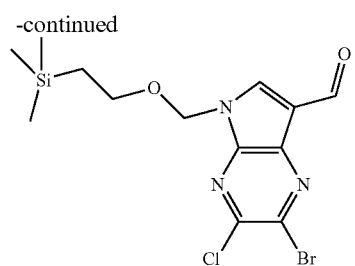

To a stirred suspension of 2-bromo-3-chloro-5H-pyrrolo[2,3-b]pyrazine-7-carbaldehyde (2.0 g, 7.69 mmol) was added LiHMDS (1 M in THF) (9.46 mL, 9.46 mmol) at 0° C. After 1 h, trimethylsilyl ethoxy methoxy chloride (1.5 mL, 8.46 mmol) was added and the reaction mixture warmed to room temperature over 30 min. The reaction mixture was diluted with aqueous $Na_2CO_3$ solution (1.56 g in 35 mL water) and then extracted with ethyl acetate (100 mL×3). The combined organic layers were washed with brine, then purified by chromatography (silica, 5-10% ethyl acetate in hexanes) to give 2-bromo-3-chloro-5-(2-trimethylsilanyl-ethoxymethyl)-5H-pyrrolo[2,3-b]pyrazine-7-carbaldehyde (1.96 g, 65%) as a brown solid. LC-MS: 392.2 (M+H).

Step 8

2-Bromo-3-chloro-5-(2-trimethylsilanyl-ethoxymethyl)-5H-pyrrolo[2,3-b]pyrazine-7-carboxylic acid

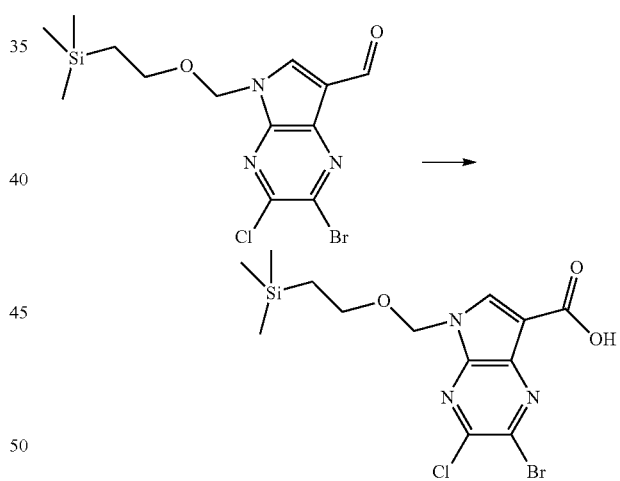

To a stirred solution of 2-bromo-3-chloro-5-(2-trimethylsilanyl-ethoxymethyl)-5H-pyrrolo[2,3-b]pyrazine-7-carbaldehyde (1.96 g, 5.03 mmol) in a (1:1) mixed solvent system of 1,4-dioxane:water (105 mL), were added sulfamic acid (2.93 g, 30.15 mmol), sodium chlorite (0.591 g, 6.53 mmol) and potassium dihydrogen phosphate (8.20 g, 60.3 mmol). The mixture was stirred overnight at room temperature The resulting mixture was diluted with water (50 mL) and extracted with ethyl acetate (150 mL×3). The combined organic phases were washed with brine, dried and concentrated in vacuo to a yellow solid which was thoroughly washed with hexane to give 2-bromo-3-chloro-5-(2-trimethylsilanyl-ethoxymethyl)-5H-pyrrolo[2,3-b]pyrazine-7-carboxylic acid (1.62 g, 79%) as off-white solid. LC-MS: 406.2 (M–H).

Step 9

2-Bromo-N-tert-butyl-3-chloro-5-((2-(trimethylsilyl)ethoxy)methyl)-5H-pyrrolo[2,3-b]pyrazine-7-carboxamide

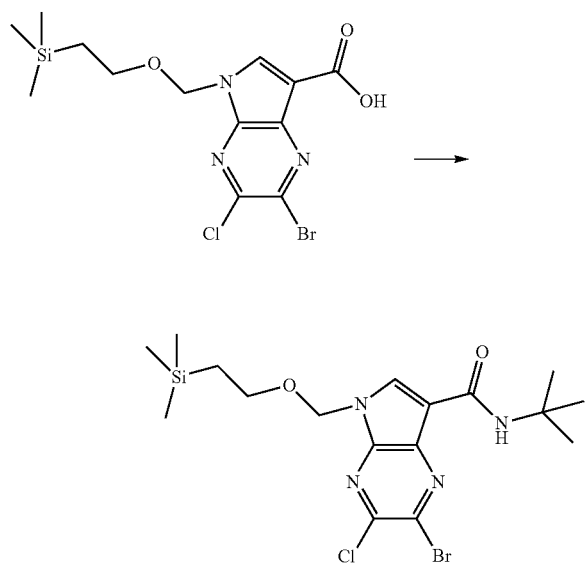

To a solution of 2-bromo-3-chloro-5-((2-(trimethylsilyl)ethoxy)methyl)-5H-pyrrolo[2,3-b]pyrazine-7-carboxylic acid (600 mg, 1.48 mmol) in DMF (5 mL) was added 1-(3-dimethylaminopropyl)-3-ethylcarbodiimide hydrochloride (650 mg, 3.39 mmol) and HOBT (520 mg, 3.39 mmol) and the mixture stirred for 10 min. 2-methylpropan-2-amine (432 mg, 5.9 mmol) was added and the mixture stirred at room temperature for 16 h, then diluted with 10% citric acid and ethyl acetate. The organic layer was separated and washed with 10% citric acid, saturated aqueous $NaHCO_3$ and brine, then concentrated in vacuo and purified by chromatography (silica, 5-20% ethyl acetate in hexanes) to give 2-bromo-N-tert-butyl-3-chloro-5-((2-(trimethylsilyl)ethoxy)methyl)-5H-pyrrolo[2,3-b]pyrazine-7-carboxamide (530 mg, 1.15 mmol, 78%) as a white solid. $^1$H NMR (400 MHz, CHLOROFORM-d) δ ppm: 8.30 (s, 1H), 7.72 (s, 1H), 5.64 (s, 2H), 3.57 (t, J=8.3 Hz, 2H), 1.56 (s, 9H), 0.96 (t, J=8.3 Hz, 2H), 0.01 (s, 9H).

Step 10

N-tert-butyl-3-chloro-2-(3-methylisothiazol-5-ylamino)-5-((2-(trimethylsilyl)ethoxy)methyl)-5H-pyrrolo[2,3-b]pyrazine-7-carboxamide

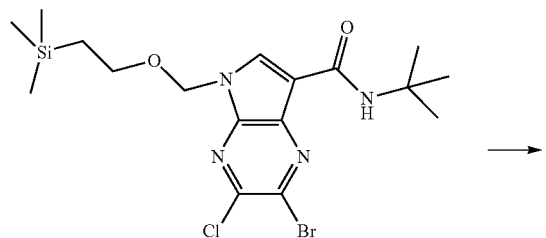

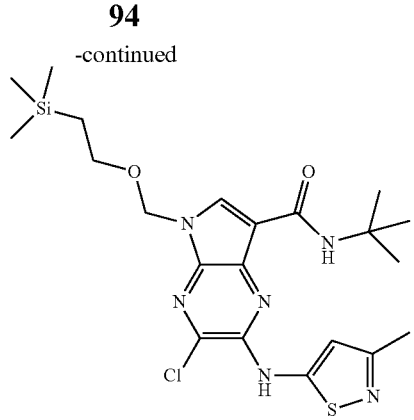

A mixture of 2-bromo-N-tert-butyl-3-chloro-5-((2-(trimethylsilyl)ethoxy)methyl)-5H-pyrrolo[2,3-b]pyrazine-7-carboxamide (125 mg, 271 μmol), 3-methylisothiazol-5-amine hydrochloride (61.2 mg, 406 μmol), $Pd_2(dba)_3$ (24.8 mg, 27.1 μmol), xantphos (47.0 mg, 81.2 μmol) and cesium carbonate (265 mg, 812 μmol) in dioxane (1.5 mL) was heated in a microwave at 150° C. for 20 min. $Pd_2(dba)_3$ (24.8 mg, 27.1 μmol) and xantphos (47.0 mg, 81.2 μmol) were added and continued to heat in a microwave at 150° C. for 30 min. The mixture was cooled then filtered through a pad of celite. The filtrate was concentrated in vacuo then purified by chromatography (silica, 10-50% ethyl acetate in hexanes) to give N-tert-butyl-3-chloro-2-(3-methylisothiazol-5-ylamino)-5-((2-(trimethylsilyl)ethoxy)methyl)-5H-pyrrolo[2,3-b]pyrazine-7-carboxamide (40 mg, 48.5 μmol, 17.9%) as brown gum. (EI/CI) m/z: 495.1 [M+H].

Step 11

N-tert-butyl-3-chloro-2-(3-methylisothiazol-5-ylamino)-5H-pyrrolo[2,3-b]pyrazine-7-carboxamide

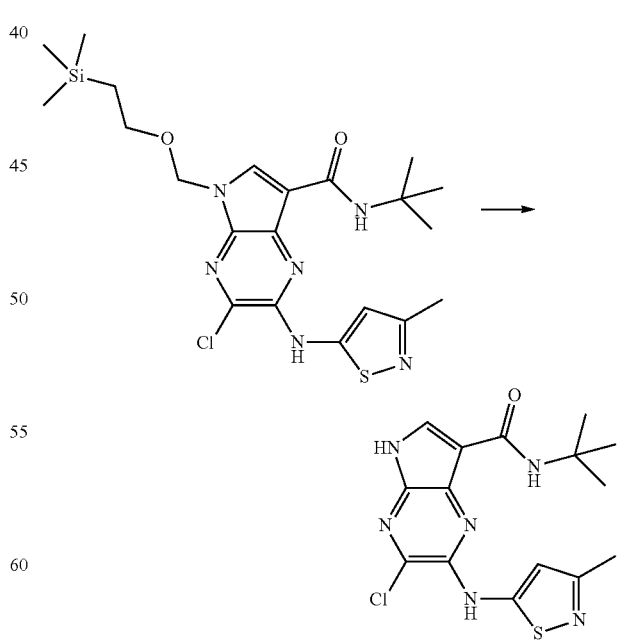

To a solution of N-tert-butyl-3-chloro-2-(3-methylisothiazol-5-ylamino)-5-((2-(trimethylsilyl)ethoxy)methyl)-5H-pyrrolo[2,3-b]pyrazine-7-carboxamide (40 mg, 80.8 μmol) in dichloromethane (1.5 mL) was added trifluoroacetic acid (184 mg, 124 µL, 1.62 mmol) and the mixture stirred at room temperature for 16 h. The mixture was concentrated then re-dissolved in dichloromethane (1.5 mL), methanol (0.75 mL) and ammonium hydroxide (0.2 mL) and the mixture stirred at room temperature for 1 h. The mixture was concentrated in vacuo then triturated with water and filtered. The solid obtained was washed with ether then dried to give N-tert-butyl-3-chloro-2-(3-methylisothiazol-5-ylamino)-5H-pyrrolo[2,3-b]pyrazine-7-carboxamide (15 mg, 37.0 µmol, 46%) as a dark orange solid. $^1$H NMR (400 MHz, DMSO-d) δ ppm: 12.76 (s, 1H), 10.91 (s, 1H), 8.30 (d, J=3.2, 1 H), 7.33 (s, 1H), 7.13 (s, 1H), 2.42 (s, 3H), 1.62 (s, 9H); MS (EI/CI) m/z: 365.0 [M+H].

Biological Examples

SYK Assay Information

Determination of $IC_{50}$ of Spleen Tyrosine Kinase (SYK) inhibition:

SYK kinase assay is a standard kinase assay adapted to a 96 well plate format. This assay is performed in 96-well format for $IC_{50}$ determination with 8 samples which represented 10 half log dilutions and a 40 µL reaction volume. The assay measures the incorporation of radiolabeled $^{33}$P γATP into an N-terminally biotinylated peptide substrate, derived from naturally occurring phosphoacceptor consensus sequence (Biotin-11aa DY*E). Phosphorylated products were detected upon termination of reactions with EDTA and the addition of Streptavidin coated beads. Representative results are in Table II above.

Assay plates: 96-well MultiScreen 0.65 um filter plates (Millipore Cat. No.: MADVNOB 10) Streptavidin coated beads: Streptavidin Sepharose™, suspension 5.0 mL, in 50 mM EDTA/PBS diluted (1:100), (Amersham, Cat. No.: 17-5113-01) Compounds: 10 mM in 100% dimethylsulfoxide (DMSO), final conc.: compound 0.003-100 uM in 10% DMSO Enzyme: SYK RPA purified, truncated construct of Spleen Tyrosine Kinase aa 360-635, stock solution 1 mg/mL, MW: 31.2 KDa, final conc.:0.0005 µM.

Peptide 1: biotinylated peptide is derived from a naturally occurring phosphor-acceptor consensus sequence (Biotin-EPEGDYEEVLE), special order from QCB, stock solution 20 mM, final conc.: 5.0 µM.

ATP: Adenosine-5'-triphosphate 20 mM, (ROCHE Cat. No.: 93202720), final concentration: µM Buffer: HEPES: 2-Hydroxyethyl piperazine-2-ethanesulfonic acid (Sigma, Cat. No.: H-3375) final concentration: 50 mM HEPES pH7.5

BSA: Bovine Serum Albumin Fraction V, fatty acid free (Roche Diagnostics GmbH, Cat. No. 9100221) diluted to a final concentration of 0.1%

EDTA: EDTA stock solution 500 mM, (GIBCO, Cat. No.: 15575-038) final concentration: 0.1 mM DTT: 1,4-Dithiothreitol (Roche Diagnostics GmbH, Cat. No.: 197777), final conc.: 1 mM $MgCl_2 \times 6H_2O$: MERCK, Cat. No.: 105833.1000, final concentration: 10 mM Assay Dilution Buffer (ADB): 50 mM HEPES, 0.1 mM EGTA, 0.1 mM Na Vanadate, 0.1 mM (3-glycerophosphate, 10 mM $MgCl_2$, 1 mM DTT, 0.1% BSA, pH 7.5

Bead wash buffer: 10 g/L PBS (Phosphate buffered saline) with 2M NaCl+1% phosphoric acid.

Experimental Method:

In 40 µL volume, 26 µL of ADB diluted, purified recombinant human SYK360-635 [0.5 nM] was mixed with 4 µL of 10× concentrations of the test compounds, [usually 100 µM-0.003 µM] in [10%] DMSO and the mixture was incubated for 10 min at RT.

The kinase reaction was initiated by the addition of 10 µL 4× substrate cocktail containing the DYE peptide substrate [0 or 5 µM], ATP [20 µM] and $^{33}$PγATP [2 µCi/rxn]. After incubation at 30° C. for 15 min, the reaction was terminated by the transfer of 25 µL of the reaction sample to a 96 well 0.65 µm Millipore MADVNOB membrane/plate containing 200 µL 5 mM EDTA and 20% Streptavidine coated beads in PBS.

The unbound radionucleotides were washed under vacuum with 3×250 µL 2M NaCl; 2×250 µL 2M NaCl+1% phosphoric acid; 1×250 µL $H_2O$. After the last wash membrane/plates were transferred to an adaptor plate, heat dried for 15 min at 60° C., and 50 µL scintillation cocktail was added to each well and 4 h later the amount of radioactivity was counted in a top counter. The percent inhibition was calculated based on the uninhibited enzyme rate:

% Inhibition=100/(1+($IC_{50}$/Inhibitor conc)$^n$)

The $IC_{50}$ was calculated using a non-linear curve fit with XLfit software (ID Business Solution Ltd., Guilford, Surrey, UK).

Ramos Calcium Influx FLIPR Assay

Human B cell lymphoma cell line Ramos was cultivated in RPMI-1640 with 10% Fetal Bovine Serum (Invitrogen). Cells were seeded into assay plate and loaded with calcium dye by adding 30 µl of dye loading buffer according to manufacturer's instruction (Beckton Dickinson Calcium Kit, Cat#80500). The cells were then treated with serial diluted compounds for 30 min before stimulation. Baseline fluorescence was recorded for about 20 seconds followed by stimulation with mouse anti-human IgM (10 µg/mL, clone M2E6, Antibody Solutions Inc.) for Ramos cells, and record of the maximal fluorescent counts in each well. Maximal counts divided by baseline counts, defined as fold change from baseline for each well, was used for $IC_{50}$ calculation.

B Cell CD69 Up-Regulation Assay in Human Whole Blood

Human Blood was collected from healthy volunteers into Vacutainers (BD Biosciences, San Jose, Calif.) containing sodium heparin. Test compound was suspended in DMSO and nine half-log serial dilutions were made. The concentration of compound in the assay was 0.5%. 100 µL whole blood was pre-incubated with compound for 30 min and then stimulated with goat F(ab')$_2$ anti-human IgM (50 µg/mL, Southern Biotech) for 20 h. At the end of the 20 hour incubation, samples were incubated with fluorochrome-conjugated antibodies, PE mouse anti-human CD20 and APC Mouse anti-human CD69 (BD Biosciences), for 30 minutes. Samples were then lysed with Lyse solution (BD) and washed with PBS containing 2% fetal bovine serum (FBS). Fluorescent signals were acquired on flow cytometer LSR II (BD) and data were analyzed by Flow Jo. The percentage of activated (CD69hi) B-cell lymphocytes (CD20+) were determined using un-stimulated (negative control) and stimulated (positive control) wells as reference guidelines. The percentage inhibition was calculated and an $IC_{50}$ curve was constructed using GraphPad Prism software with sigmoidal curve fitting.

Data are shown below in μM in Table II.

TABLE II

| Compound | ENZYME_FILTRATION_IC50 | RAMOS_IC50 | Ic50: human whole blood |
|---|---|---|---|
| I-1 | 0.0085 | 0.1221 | 0.6271 |
| I-2 | 0.0274 | 0.2447 | 0.5354 |
| I-3 | 0.0211 | 0.1463 | 0.2039 |
| I-4 | 0.0428 | 0.2583 | 0.9178 |
| I-5 | 0.0137 | 0.1100 | 0.0758 |

SEQUENCE LISTING

<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Biotinylated peptide

<400> SEQUENCE: 1

Glu Pro Glu Gly Asp Tyr Glu Glu Val Leu Glu
1               5                   10

TABLE II-continued

| Compound | ENZYME_FILTRATION_IC50 | RAMOS_IC50 | Ic50: human whole blood |
|---|---|---|---|
| I-6 | 0.0171 | 0.1146 | 0.4304 |
| I-7 | 0.1637 | 0.2827 | 0.2575 |
| I-8 | 0.0513 | 0.3344 | 0.4220 |
| I-9 | 0.0155 | 0.0931 | 0.3429 |
| I-10 | 0.0163 | 0.0645 | |
| I-11 | 0.0109 | 1.3326 | |
| I-12 | 0.0032 | 0.0767 | 2.1550 |
| I-13 | 0.0128 | 0.0690 | 0.1901 |
| I-14 | 0.0359 | 0.1013 | 0.1835 |
| I-15 | 0.9339 | 6.9366 | |
| I-16 | 0.0924 | 0.1679 | 0.3753 |
| I-17 | 0.0499 | 0.2071 | 0.1933 |
| I-18 | 0.0020 | 0.0789 | 0.1253 |
| I-19 | 0.1168 | 0.5184 | |
| I-20 | 0.0300 | 0.3382 | 0.5064 |
| I-21 | 1.9017 | 4.8011 | >50 |
| I-22 | 0.0251 | 0.0797 | 1.3414 |
| I-23 | 0.1166 | 3.6170 | 0.6298 |
| I-24 | 0.0059 | 0.0933 | 0.4185 |
| I-25 | 0.0712 | 0.2133 | 0.4333 |
| I-26 | 0.0056 | 0.2162 | |
| I-27 | 0.0188 | 0.2232 | 0.6311 |
| I-28 | 0.1208 | 0.8062 | |
| I-29 | 0.2275 | 0.6417 | |
| I-30 | 0.0975 | 0.2777 | 0.2677 |
| I-31 | 0.0178 | 0.2508 | |
| I-32 | 0.0437 | 0.2750 | 1.1399 |
| I-33 | 0.1674 | 0.7908 | 1.4596 |
| I-34 | 1.0674 | 2.1666 | 5.1197 |
| I-35 | 2.9354 | | |
| I-36 | 0.2507 | 1.2481 | 8.2994 |
| I-37 | 0.0048 | 0.0377 | |
| I-38 | 0.6400 | 14.8785 | |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:
1. A compound of Formula I:

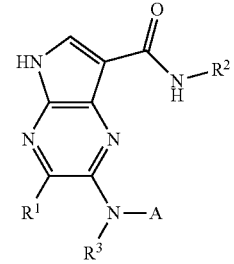

wherein:
$R^1$ is H, halo, or lower alkyl;
$R^2$ is lower alkyl;
$R^3$ is H or lower alkyl;
A is monocyclic or bicyclic heteroaryl or phenyl, optionally substituted with one or more A'; and
each A' is independently lower alkyl, halo, lower alkyl sulfonyl, amido, lower hydroxyalkyl, lower alkoxy, amino lower alkyl, or deuterium;
or a pharmaceutically acceptable salt thereof.

2. The compound of claim 1, wherein $R^3$ is lower alkyl.
3. The compound of claim 1, wherein $R^3$ is H.
4. The compound of claim 1, wherein $R^1$ is H.
5. The compound according to claim 1, wherein A is pyridinyl, pyrimidyl, pyrazolyl, isoxazolyl, thiadiazolyl, thiazolyl, pyrazinyl or phenyl, optionally substituted with one or more A'.
6. The compound according to claim 1, wherein each A' is independently lower alkyl, halo, lower alkyl sulfonyl, lower hydroxyalkyl, lower alkoxy, amino lower alkyl, or deuterium.

7. The compound according to claim 1, wherein A is monocyclic heteroaryl optionally substituted with one or more A'.

8. The compound according to claim 1, wherein A' is lower alkyl.

9. The compound according to claim 1, wherein A' is lower alkyl sulfonyl.

10. The compound according to claim 1, wherein A is phenyl optionally substituted with one or more A'.

11. The compound according to claim 1, wherein A' is lower alkyl or lower alkyl sulfonyl.

12. The compound according to claim 1, wherein A is bicyclic heteroaryl optionally substituted with one or more A'.

13. The compound according to claim 1, selected from the group consisting of:
- N-tert-butyl-2-(5-methylpyridin-2-ylamino)-5H-pyrrolo[2,3-b]pyrazine-7-carboxamide;
- N-tert-butyl-2-(1-methyl-1H-pyrazol-3-ylamino)-5H-pyrrolo[2,3-b]pyrazine-7-carboxamide;
- N-isopropyl-2-(5-methylpyridin-2-ylamino)-5H-pyrrolo[2,3-b]pyrazine-7-carboxamide;
- N-tert-butyl-2-(1-methyl-1H-pyrazol-4-ylamino)-5H-pyrrolo[2,3-b]pyrazine-7-carboxamide;
- N-tert-butyl-2-(6-methylpyridin-3-ylamino)-5H-pyrrolo[2,3-b]pyrazine-7-carboxamide;
- N-tert-butyl-2-(2-methylpyrimidin-5-ylamino)-5H-pyrrolo[2,3-b]pyrazine-7-carboxamide;
- N-tert-butyl-2-(5-methylpyrazin-2-ylamino)-5H-pyrrolo[2,3-b]pyrazine-7-carboxamide;
- N-tert-butyl-2-(3-methyl-1H-pyrazol-5-ylamino)-5H-pyrrolo[2,3-b]pyrazine-7-carboxamide;
- N-tert-butyl-2-(pyridin-3-ylamino)-5H-pyrrolo[2,3-b]pyrazine-7-carboxamide;
- N-tert-butyl-2-(2-fluoro-4-methylphenylamino)-5H-pyrrolo[2,3-b]pyrazine-7-carboxamide;
- N-tert-butyl-2-(p-tolylamino)-5H-pyrrolo[2,3-b]pyrazine-7-carboxamide;
- N-tert-butyl-2-(3-(methylsulfonyl)phenylamino)-5H-pyrrolo[2,3-b]pyrazine-7-carboxamide;
- N-tert-butyl-2-(1-ethyl-1H-pyrazol-4-ylamino)-5H-pyrrolo[2,3-b]pyrazine-7-carboxamide;
- N-tert-butyl-2-(2-(dimethylcarbamoyl)phenylamino)-5H-pyrrolo[2,3-b]pyrazine-7-carboxamide;
- N-tert-butyl-2-(1,5-dimethyl-1H-pyrazol-4-ylamino)-5H-pyrrolo[2,3-b]pyrazine-7-carboxamide;
- N-tert-butyl-2-(3-methylisothiazol-5-ylamino)-5H-pyrrolo[2,3-b]pyrazine-7-carboxamide;
- N-tert-butyl-2-(2,4-dimethylphenylamino)-5H-pyrrolo[2,3-b]pyrazine-7-carboxamide;
- N-tert-butyl-2-(4-(methylsulfonyl)phenylamino)-5H-pyrrolo[2,3-b]pyrazine-7-carboxamide;
- N-tert-butyl-2-(methyl(pyridin-3-yl)amino)-5H-pyrrolo[2,3-b]pyrazine-7-carboxamide;
- N-tert-butyl-2-(3-methylisoxazol-5-ylamino)-5H-pyrrolo[2,3-b]pyrazine-7-carboxamide;
- N-tert-butyl-2-(6-(methylsulfonyl)pyridin-3-ylamino)-5H-pyrrolo[2,3-b]pyrazine-7-carboxamide;
- N-tert-butyl-2-(3-(1-hydroxyethyl)phenylamino)-5H-pyrrolo[2,3-b]pyrazine-7-carboxamide;
- N-tert-butyl-2-(2-methoxypyrimidin-5-ylamino)-5H-pyrrolo[2,3-b]pyrazine-7-carboxamide;
- 2-(3-(1-aminoethyl)phenylamino)-N-tert-butyl-5H-pyrrolo[2,3-b]pyrazine-7-carboxamide;
- N-tert-butyl-2-(2-(methylsulfonyl)pyridin-4-ylamino)-5H-pyrrolo[2,3-b]pyrazine-7-carboxamide;
- N-tert-butyl-2-(5-(methylsulfonyl)pyridin-3-ylamino)-5H-pyrrolo[2,3-b]pyrazine-7-carboxamide;
- N-tert-butyl-2-(1,3-dimethyl-1H-pyrazol-4-ylamino)-5H-pyrrolo[2,3-b]pyrazine-7-carboxamide;
- N-tert-butyl-2-(3-methyl-1,2,4-thiadiazol-5-ylamino)-5H-pyrrolo[2,3-b]pyrazine-7-carboxamide;
- 3-Methyl-2-(1-methyl-1H-pyrazol-4-ylamino)-5H-pyrrolo[2,3-b]pyrazine-7-carboxylic acid tert-butylamide;
- 2-(3-Methanesulfonyl-phenylamino)-3-methyl-5H-pyrrolo[2,3-b]pyrazine-7-carboxylic acid tert-butylamide;
- 3-Methyl-2-(3-methyl-isothiazol-5-ylamino)-5H-pyrrolo[2,3-b]pyrazine-7-carboxylic acid tert-butylamide;
- 2-Phenylamino(D5)-5H-pyrrolo[2,3-b]pyrazine-7-carboxylic acid tert-butylamide; and
- N-tert-butyl-3-chloro-2-(3-methylisothiazol-5-ylamino)-5H-pyrrolo[2,3-b]pyrazine-7-carboxamide.

14. A method for treating rheumatoid arthritis comprising administering to a patient in need thereof a therapeutically effective amount of the compound according to claim 1.

15. A pharmaceutical composition comprising a therapeutically effective amount of the compound according to claim 1, admixed with at least one pharmaceutically acceptable carrier, excipient or diluent.

16. The pharmaceutical composition of claim 15, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

* * * * *